US008329316B2

(12) United States Patent
Kim et al.

(10) Patent No.: US 8,329,316 B2
(45) Date of Patent: Dec. 11, 2012

(54) TETRAPHENYLNAPHALENE DERIVATIVES AND ORGANIC LIGHT EMITTING DIODE USING THE SAME

(75) Inventors: Yeon-Hwan Kim, Goyang-si (KR); Dong-Hoon Lee, Seoul (KR); Hye-Young Jang, Daejeon Metropolitan (KR); Sung-Kil Hong, Daejeon Metropolitan (KR); Sung-Jin Yeo, Daejeon Metropolitan (KR); Kong-Kyeom Kim, Daejeon Metropolitan (KR); Dong-Seob Jeong, Seoul (KR); So-Yeon Choi, legal representative, Daejeon (KR)

(73) Assignee: LG Chem, Ltd., Seoul (KR)

( * ) Notice: Subject to any disclaimer, the term of this patent is extended or adjusted under 35 U.S.C. 154(b) by 233 days.

(21) Appl. No.: 12/224,877

(22) PCT Filed: Mar. 9, 2007

(86) PCT No.: PCT/KR2007/001174
§ 371 (c)(1),
(2), (4) Date: Nov. 12, 2008

(87) PCT Pub. No.: WO2007/105884
PCT Pub. Date: Sep. 20, 2007

(65) Prior Publication Data
US 2009/0174312 A1    Jul. 9, 2009

(30) Foreign Application Priority Data

Mar. 10, 2006  (KR) .................. 10-2006-0022845

(51) Int. Cl.
*H01L 51/54* (2006.01)
*C09K 11/06* (2006.01)
(52) U.S. Cl. .......... 428/690; 428/917; 313/504; 585/26; 568/3; 556/432; 548/310.7; 548/314.4; 548/440; 549/1
(58) Field of Classification Search .................. None
See application file for complete search history.

(56) References Cited

U.S. PATENT DOCUMENTS

| 5,077,142 | A * | 12/1991 | Sakon et al. ................ 428/690 |
| 2003/0039858 | A1 * | 2/2003 | Igarashi et al. ............. 428/690 |
| 2004/0232409 | A1 * | 11/2004 | Igarashi et al. ............. 257/40 |
| 2005/0019604 | A1 | 1/2005 | Thompson et al. |
| 2005/0025993 | A1 | 2/2005 | Thompson et al. |
| 2007/0252511 | A1 | 11/2007 | Funahashi |

FOREIGN PATENT DOCUMENTS

| EP | 926216 A1 * | 6/1999 |
| JP | 10255985 A2 | 9/1998 |
| JP | 2003-027048 | 1/2003 |
| JP | 2004-256420 | 9/2004 |
| JP | 2005-302657 | 10/2005 |
| WO | WO 2004113412 A2 * | 12/2004 |
| WO | WO 2005/108348 A1 | 11/2005 |

OTHER PUBLICATIONS

Beringer, F. Marshall, et al: Diaryliodonium salts. XX. "Rearrangement and cleavage of 2-aryliodoniobenzoates, Trapping agents for benzyne", Journal of Organic Chemistry, 1964, 29(2), 445-8, ISSN: 0022-3263; See compounds(RN: 97734-47-9 & 97828-32-5 CAPLUS); STN International, Fil Caplus, AN. 1964:45482, DN. 60:45482.

Miao, Q., Chi, X., et al.; "Organization of Acenes with a Cruciform Assembly Motif" Journal of the American Chemical Society, Jan. 11, 2006, 128(4), 1340-1345, ISSN: 0002-7863; See a compound in supporting Informaiton (RN: 874438-77-4 CAPLUS); STN International, File Caplus, AN. 2006-20533, DN. 144:170642,.

Morikawa, A., Hatakeyama, T.: "Synthesis and characterization of novel aromatic polyamides from 1, 4-bis(4-aminophenyl)-2,3-diphenylnaphthalene and aromatic dicarboxylic acids" Polymer Journal (Tokyo), 1999, 31(1), 66-69, ISSN: 0032-3896; See a compound(RN: 220916-93-8 CAPLUS); STN International, File CAPLUS, AN. 1999:67388, DN. 130:210043.

Morikawa, A., Hatakeyama, T.: "Synthesis and characterization of novel aromatic polyamides from 1, 4-bis(4-aminophenyl)-2,3-diphenylnaphthalene and Aromatic Tetracarboylic Dianhydrides" Polymer Journal (Tokyo), 1999, 31(1), 76-80, ISSN: 0032-3896; See a compound(RN: 220916-93-8 CAPLUS); STN International, File CAPLUS, AN. 1999:67388, DN. 130:210043.

Baigrie, B., et al.: "Simple, Convenient, and direct conversion of anilines and anilides into arynes" Journal of the Chemical Society, Perkin Transactions 1, 1972, (20), 2563-7, ISSN: 0300-922X; See Componds(RN. 38382-46-6, 38382-51-3 & 38382-52-4 CAPLUS); STN International, File Caplus, AN. 1972:551541, DN. 77:151541.

Rees, C.W., West, D.E.; Reactive intermediates. XI.; "Generation and some reactions of benzynequinone" Journal of the Chemical Society [Section} C: Organic, 1970, (4) 583-9 ISSN: 0022-4952; See a compound (RN. 26002-78-8 CAPLUS); STN International, file CAPLUS, AN. 1970:100225, DN. 72:100225.

Neumann, W.P., Schriewer, M.,: 7-Germanordbornadienes and their thermal cycloeliminations, Tetrahedron Letters, 1980, 21(34), 3273-6, ISSN: 0040-4039; See compounds 4-8 in Table 1; STN International, File CAPLUS, AN. 1981:15826, DN. 94: 15826.

Harrington, Cameron R., et al.; "Time-resolved spectroscopic studies of the photochemistry of some diphenylgermylene ($Ph_2Ge$:) precursors1"; received Mar. 9, 2005; published on the NRC Research Press Web site at http:/canjchem.nrc.ca on Oct. 22, 2005; Can. J. Chem. 83: 1324-1338 (2005).

Zhou, Xin, et al.: "Novel Synthetic Route to Octasubstituted Naphthalenes from Four Alkynes and One Olefin Unit via Zirconacyclopentadienes and 1,2-Diiodo-3,4,5,6-tetraalkylbenzene"; J. Org. Chem. 2004, 69, 4559-4562; published on Web May 29, 2004.

Zhang, Jiajia, et al.; "Synthesis of an Extremely Crowded Naphthalene via a Stable Norbornadienone"; J. A.m. Chem. Soc. 2001, 123, 10919-10926; received Jun. 13, 2001; published on Web Oct. 12, 2001.

(Continued)

*Primary Examiner* — Lynda Salvatore
*Assistant Examiner* — Andrew K Bohaty
(74) *Attorney, Agent, or Firm* — McKenna Long & Aldridge LLP

(57) ABSTRACT

The present invention provides a novel tetraphenylnaphthalene derivative, and an organic light emitting device using the same.

7 Claims, 2 Drawing Sheets

OTHER PUBLICATIONS

Pascal, Robert A., et al.; "Giant Cyclophanes Built from Polyphenyl Aromatic Substructures"; The Journal of Organic Chemistry, vol. 65, received Nov. 17, 2000; published on Web Sep. 16, 2000.

Qiao, Xiaqxin, et al.; "Synthesis and Steroochemistry of Ortho-Methylated Octaphenylnaphthalense"; Department of Chemistry, Princeton University, Princeton, New Jersey; Chirality 10:154-158; published Feb. 5, 1997.

Mondal, S., et al.; "Polycyclic Aromatic compounds; Part VIII—A New Synthesis of Polycyclics Containing Phenanthrene Nucleus"; Department of Chemistry, Burdwan University, Burdwan 713 104; Indian Journal of Chemistry; vol. 22B, May 1983, pp. 448-452; published Dec. 23, 1981.

Mazur, Stephen, et al.: "Chemistry of Polymer-Bound o-Benzyne. Frequency of Encounter between Substituents on Cross-Linked polystyrenes"; Contribution from the Department of Chemistry, The University of Chicago, Chicago, Illinois 60637; received Jul. 11, 1978, J. Cas., 1979.

Brydon, D. L., et al.; "Acylarylnitrosamines. Part IV.[1] Aryne participation in decompositions of N-Nitrosoacetanilide and its m- and p-t-Butyl-, -0, m-, and p-Chloro-Derivatives in Benzene †"; Department s of Chemistry, University of Edinburgh, West Mains Road, Edinburgh EH93JJ, and University of St. Andrews, The Purdie Building, St. Andrews, Scotland; J. Chem. Soc., (B), 1971, pp. 1996-2006.

Cadogan, J. I. G., et al.; "Acylarylnitrosamines. Part II[1] The Formation of Arynes in the Anomalous Decompositions of 0-t-Butyl- and 2,5-Di-t-butyl-N-nitrosoacet-anilide"; University of St. Andrews, St. Andres and University of Edinburgh, Edinburgh, Scotland; J. Chemical Society, 1971, pp. 595-601.

Harrision, R., et al.; "Aryne Chemstry-XI[1]—Trapping Agents for Arynes Produced from Grignard and Organolithium Reagents"; Department of Chemistry, Loughborough University of Technology, Loughborough, Leicestershire; School of Chemistry, The University of Bradford, 7, Yorks; received in the UK Nov. 27, 1967; published Feb. 3, 1968.

Jeff B. Debad et al.: "Electrogenerated Chemiluminescence 60. Spectroscopic Properties and Electrogenerated Chemiluminescence of Decaphenylanthracene and Octaphenylnaphthalene", Acta Chemica Scandinavia, vol. 52, 1988, pp. 45-50, XP002601134.

Ling Tong et al.: "The Albatrossenes: Large, Cleft-Containing, Polyphenyl Polycyclic Aromatic Hydrocarbons", Journal of the American Chemical Society, vol. 119, 1997, pp. 7291.7302, XP002601135.

J.R. Williamson, S.E. Mallakpour, "Synthesis and trapping of 3,4,3',4'-tetradehydrobiphenyl (bisbenzyne)", Iranian Journal of Chemistry & Chemical Engineering, 1991, vol. 10, No. 1, pp. 66-78.

Shadpour E. Mallakpour, Salar Hematy, "Reaction of 3,4,3',4'-tetradehydrobiphenyl (bisbenzyne) with tetracyclone and acecyclone", Indian Journal of Chemistry, Section B: Organic Chemistry Including Medical Chemistry, 2000, vol. 39B, No. 3, pp. 173-176.

Tsugio Kitamura et al., "A New and Efficient Hypervalent Iodine-Benzyne Precursor, (Phenyl)[o-(trimethylsilyl)phenyl]iodonium Triflate: Generation, Trapping Reaction, and Nature of Benzyne", Journal of the American Chemical Society, 1999, vol. 121, No. 50, pp. 11674-11679.

Michel Pfeffer et al., "Novel carbon-carbon bond formation induced by depalladation of organometallic compounds", Journal of Organometallic Chemistry, 1989, vol. 371, No. 1, pp. C21-C25.

* cited by examiner

TETRAPHENYLNAPHALENE DERIVATIVES AND ORGANIC LIGHT EMITTING DIODE USING THE SAME

This application is a 371 national stage entry of International Application No. PCT/KR2007/001174, filed on Mar. 9, 2007 that claims priority to Korean Patent Application No. 10-2006-0022845, filed on Mar. 10, 2006, both of which are hereby incorporated by reference in their entirety.

TECHNICAL FIELD

The present invention relates to a novel structure of a tetraphenylnaphthalene derivative, and an organic light emitting device using the same. This application claims priority from Korean Patent Application No. 10-2006-0022845 filed on Mar. 10, 2006 in the Korean Intellectual Property Office, the disclosure of which is incorporated herein by reference in its entirety.

BACKGROUND ART

In general, the term "organic light emitting phenomenon" refers to a phenomenon in which electric energy is converted to light energy by means of an organic material. The organic light emitting device using the organic light emitting phenomenon has a structure usually comprising an anode, a cathode and an organic material layer interposed therebetween. Herein, the organic material layer may be mostly formed in a multilayer structure comprising layers of different materials, for example, a hole injecting layer, a hole transporting layer, a light emitting layer, an electron transporting layer, an electron injecting layer and the like, in order to improve efficiency and stability of the organic light emitting device. In the organic light emitting device having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such the organic light emitting device is known to have characteristics such as self-luminescence, high brightness, high efficiency, low drive voltage, wide viewing angle, high contrast and high-speed response.

The materials used for the organic material layer of the organic light emitting device can be classified into a light emitting material and a charge transporting material, for example, a hole injecting material, a hole transporting material, an electron transporting material and an electron injecting material, according to their functions. The light emitting material can be classified into a high molecular weight type and a low molecular weight type, according to their molecular weight, and divided into a fluorescent material from singlet excited states and a phosphorescent material from triplet excited states according to their light emitting mechanism. Further, the light emitting material can be classified into a blue, green or red light emitting material and a yellow or orange light emitting material required for giving more natural color, according to a light emitting color.

On the other hand, an efficiency of a device is lowered owing to maximum luminescence wavelength moved to a longer wavelength due to the interaction between the molecules, the deterioration of color purity and the reduction in light emitting efficiency when only one material is used for the light emitting material, and therefore a host/dopant system can be used as the light emitting material for the purpose of enhancing the color purity and the light emitting efficiency through energy transfer. It is based on the principle that if a small amount of a dopant having a smaller energy band gap than a host which forms a light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according to the kind of the dopant.

In order to allow the organic light emitting device to fully exhibit the above-mentioned excellent characteristics, a material constituting the organic material layer in the device, for example, a hole injecting material, a hole transporting material, a light emitting material, an electron transporting material and an electron injecting material should be essentially composed of a stable and efficient material. However, the development of a stable and efficient organic material layer material for the organic light emitting device has not yet been fully realized. Accordingly, the development of new materials is continuously desired.

DISCLOSURE OF INVENTION

Technical Problem

The present inventors have found a novel structure of a tetraphenylnaphthalene derivative. Further, they have found that upon applying the compound in the organic light emitting device, it can greatly improve the optical efficiency, the stability, the life time of the devices.

Therefore, it is an object of the present invention to provide a novel structure of a tetraphenylnaphthalene derivative, and an organic light emitting device using the same.

Technical Solution

The present invention provides a compound of the following Formula 1.

[Formula 1]

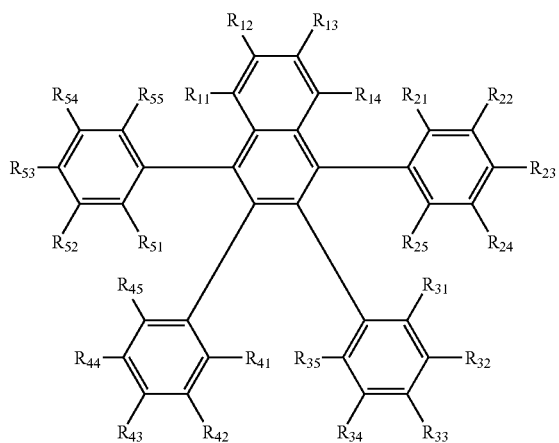

wherein
$R^{11}$ to $R^{14}$, $R^{21}$ to $R^{25}$, $R^{31}$ to $R^{35}$, $R^{41}$ to $R^{45}$, and $R^{51}$ to $R^{55}$ are the same or different from each other, and independently selected from the group consisting of a hydrogen atom, a substituted or unsubstituted straight or branched chain aliphatic hydrocarbon group, a substituted or unsubstituted arylalkyl group, a substituted or unsubstituted arylalkenyl group, a substituted or unsubstituted arylalkynyl group, a substituted or un-substituted aliphatic cyclic group, a substituted or unsubstituted heterocyclic group, a substituted or unsubstituted aromatic cyclic group, a substituted or unsubstituted heteroaromatic cyclic group, a condensed ring group formed by two or more rings selected from the above rings, —BR'R", —NR'R", —OR', —PR'R", —SR' and SiR'R"R''', wherein R', R" and R''' are each independently selected from the group consisting of a hydrogen atom, a substituted or unsubstituted straight or branched chain aliphatic hydrocarbon group, a substituted or unsubstituted arylalkyl group, a substituted or un-substituted arylalkenyl group, a substituted or unsubstituted arylalkynyl group, a substituted or unsubstituted aliphatic cyclic group, a substituted or unsubstituted heterocyclic group, a substituted or unsubstituted aromatic cyclic group, a substituted or unsubstituted heteroaromatic cyclic group and a condensed ring group formed by two or more rings selected from the above rings, provided that $R^{11}$ to $R^{14}$, $R^{21}$ to $R^{25}$, $R^{31}$ to $R^{35}$, $R^{41}$ to $R^{45}$, and $R^{51}$ to $R^{55}$ are not hydrogen at the same time.

Further, the invention provides an organic light emitting device comprising a configuration of depositing a first electrode, at least one organic material layer, and a second electrode sequentially, in which the at least one organic material layer comprises a compound represented by Formula 1.

Advantageous Effects

The compound of the present invention is a novel compound, which can satisfy the requirements for use in an organic light emitting device, such as suitable energy levels by introducing various substituents to the core structure. Thus, the compound of the present invention can play various roles in the organic light emitting device. Further, upon applying the compound in the organic light emitting device, it can lower a drive voltage, and improve the optical efficiency, and enhance the life characteristics of the devices.

BEST MODE FOR CARRYING OUT THE INVENTION

Figure 1:
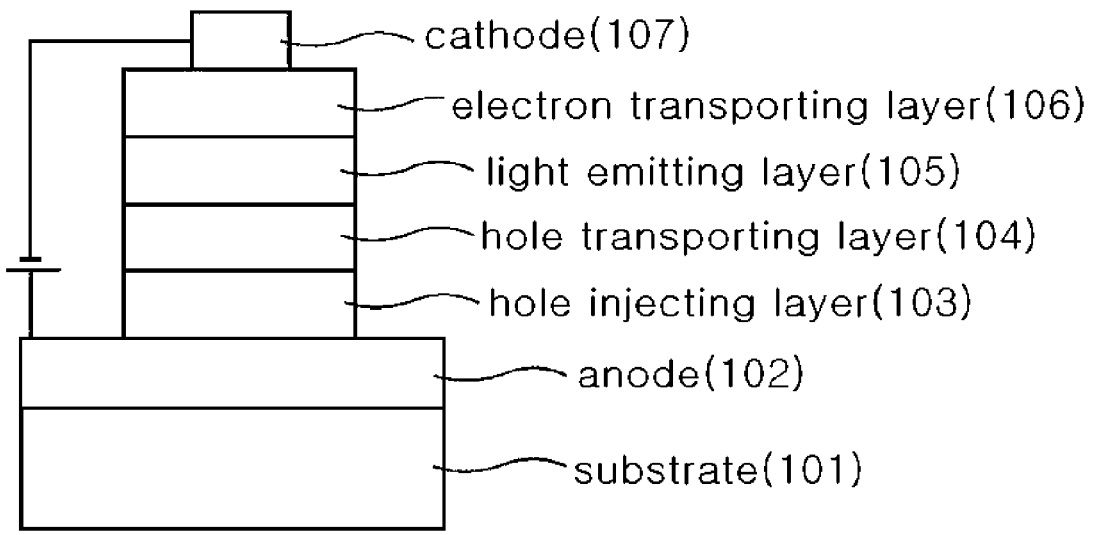
FIGS. 1 to 5 illustrate an example of the organic light emitting device, to which a novel compound of the present invention can be applied.

Hereinafter, the present invention will be described in more detail.

The present invention provides a compound of Formula 1. A detailed description will be given of the substituent groups of Formula 1.

The substituents of Formula 1 are preferably an aliphatic hydrocarbon group having 1 to 20 carbon atoms, for example, a straight or branched chain alkyl group, an alkenyl group or an alkynyl group.

The substituents of Formula 1 are preferably an aliphatic cyclic group having 5 to 20 carbon atoms, and may be a single ring or condensed ring.

The substituents of Formula 1 may be a heterocyclic group having B, N, O, P, S or Si, and may be a single ring or condensed ring.

The substituents of Formula 1 are preferably an aromatic cyclic group having 5 to 20 carbon atoms, and may be a single ring or condensed ring. Examples thereof include benzene, naphthalene, biphenyl, and anthracene, but are not limited thereto.

The substituents of Formula 1 may be a heteroaromatic cyclic group having B, N, O, P, S or Si, and may be a single ring or condensed ring. Examples thereof include an imidazole group, a thiazole group, and an oxazol group, but are not limited thereto.

An arylalkyl group, an arylalkenyl group and an arylalkynyl group among the substituents of Formula 1 are preferably an alkyl group, an alkenyl group and an alkynyl group having 1 to 20 carbon atoms substituted with an aromatic cyclic group having 5 to 20 carbon atoms, respectively.

The aliphatic hydrocarbon group, the arylalkyl group, the arylalkenyl group, the arylalkynyl group, the aliphatic cyclic group, the heterocyclic group, the aromatic cyclic group or the heteroaromatic cyclic group may be substituted or unsubstituted, respectively. In the case of being substituted, the substituents are selected from the group consisting of a substituted or unsubstituted aliphatic hydrocarbon group, a substituted or unsubstituted aliphatic cyclic group, a substituted or unsubstituted heterocyclic group, a substituted or unsubstituted aromatic cyclic group, a substituted or unsubstituted heteroaromatic cyclic group, —BR'R", —NR'R", —OR', —PR'R", —SR' and SiR'R"R''', wherein R', R" and R''' can be each independently selected from a hydrogen atom, a substituted or unsubstituted straight or branched chain aliphatic hydrocarbon group, a substituted or unsubstituted aliphatic cyclic group, a substituted or unsubstituted heterocyclic group, a substituted or unsubstituted aromatic cyclic group, a substituted or unsubstituted heteroaromatic cyclic group and a condensed ring formed by two or more rings selected from the rings, but are limited thereto.

The aliphatic hydrocarbon group, the arylalkyl group, the arylalkenyl group, the arylalkynyl group, the aliphatic cyclic group, the heterocyclic group, the aromatic cyclic group, the heteroaromatic cyclic group, —BR'R", —NR'R", —OR', —PR'R", —SR' and SiR'R"R''' comprise preferably 1 to 10 of at least one atom selected from B, N, O, P, S and Si. Specifically, $R^{11}$ to $R^{14}$, $R^{21}$ to $R^{25}$, $R^{31}$ to $R^{35}$, $R^{41}$ to $R^{45}$, and $R^{51}$ to $R^{55}$ of Formula 1 are more preferably a carbazolyl group, an arylamine group, an arylamine group substituted with an arylamine group, an arylamine group substituted with an arylalkenyl group, an arylalkenyl group substituted with an arylamine group, a bithienyl group substituted with an aryl group, a thienyl group substituted with an aryl group, an imidazolyl group substituted with an aryl group, an aryl group substituted with an imidazolyl group, a benzimidazolyl group substituted with an aryl group, an aryl group substituted with a benzimidazolyl group, a silane group substituted with an aryl group, a boron group substituted with an alkylaryl group, a heterocyclic group containing Si substituted with an aryl group or an alkyl group, or an anthracenyl group substituted with a phenyl group or a naphthyl group.

In the present invention, in the case where $R^{11}$ to $R^{14}$, $R^{21}$ to $R^{25}$, $R^{31}$ to $R^{35}$, $R^{41}$ to $R^{45}$, and $R^{51}$ to $R^{55}$ of Formula 1 are a hydrogen atom at the same time, since a functional group capable of transporting a hole or an electron, for example, an aliphatic or aromatic derivative containing a hetero atom do not exist, they cannot be used as a material for the organic material layer of an organic light emitting device.

The compound of Formula 1 may be the compounds of the following Formulae 11 to 17.

[Formula 11]
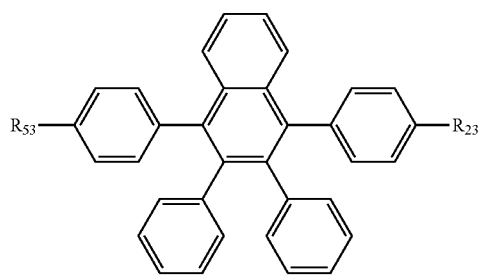
[Formula 12]
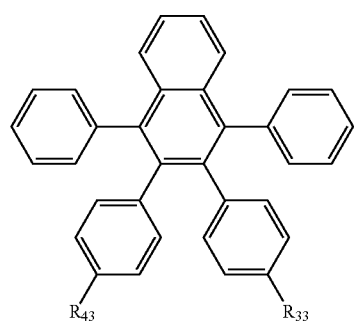
[Formula 13]
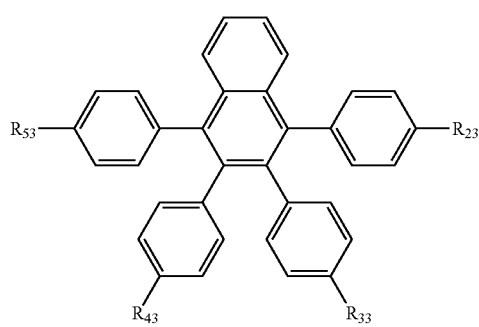
[Formula 14]
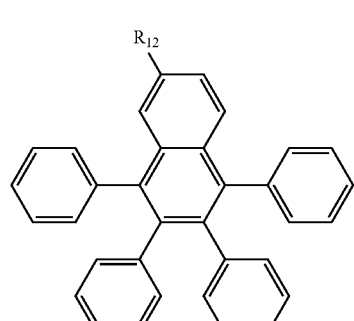
[Formula 15]
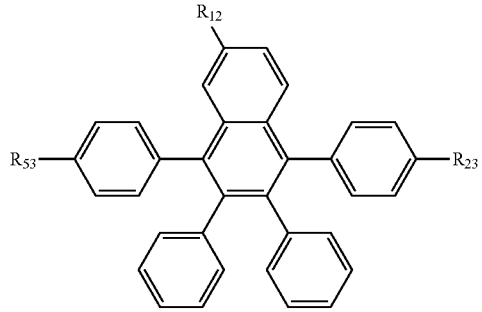
[Formula 16]
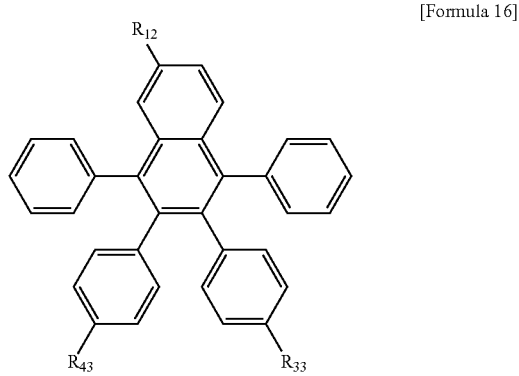
[Formula 17]
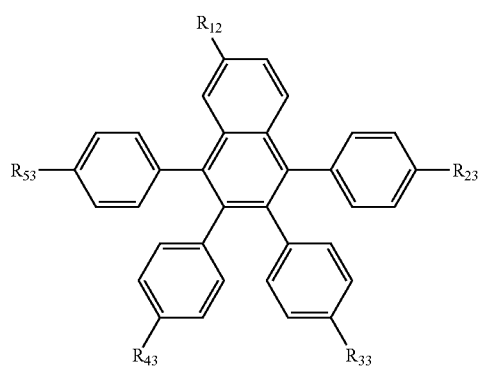
wherein $R_{12}$, $R_{23}$, $R_{33}$, $R_{43}$ and $R_{53}$ are the same as defined in Formula 1, provided that $R_{12}$, $R_{23}$, $R_{33}$, $R_{43}$ and $R_{53}$ are not substituted with hydrogen at the same time.
Specific examples according to the present invention include preferably the following compounds, but are not limited thereto.

[Formula 1-1]
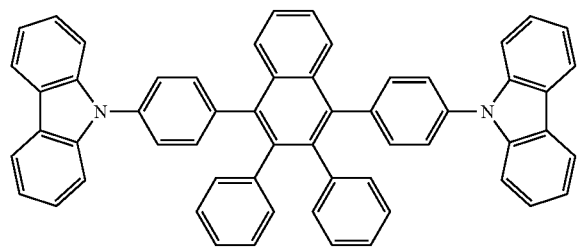
[Formula 1-2]
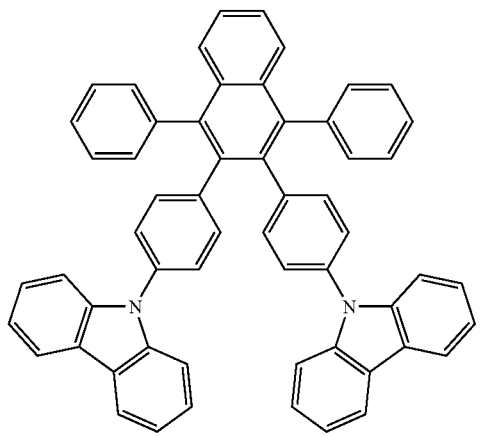
[Formula 1-3]
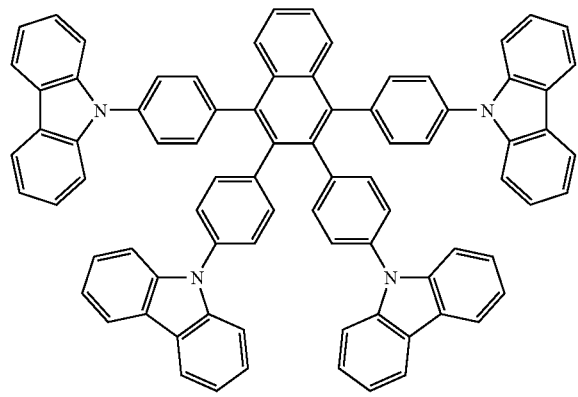
[Formula 1-4]
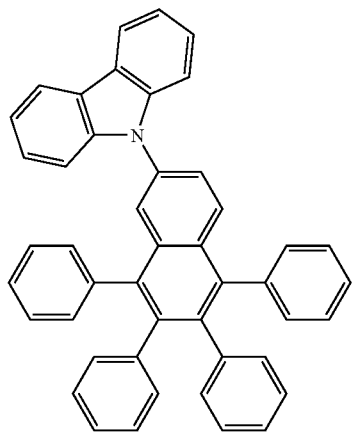
[Formula 1-5]
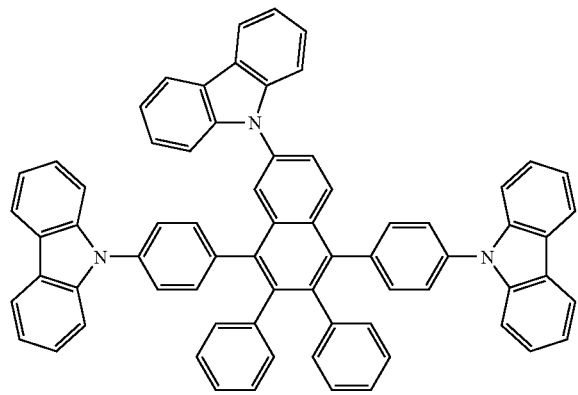
[Formula 1-6]
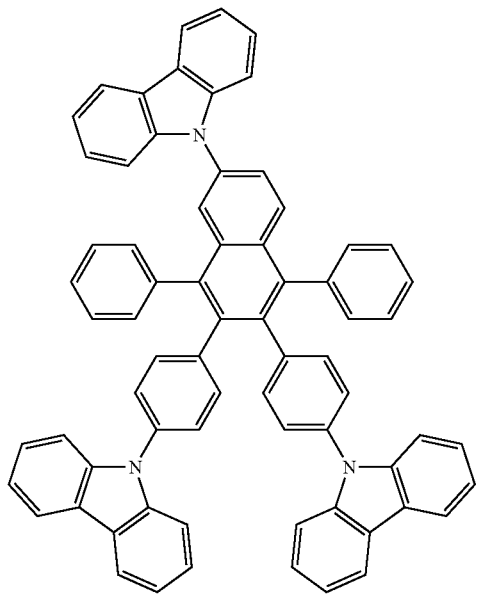

-continued
[Formula 1-7]
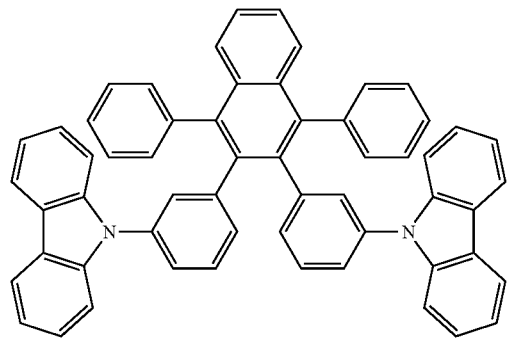
[Formula 1-8]
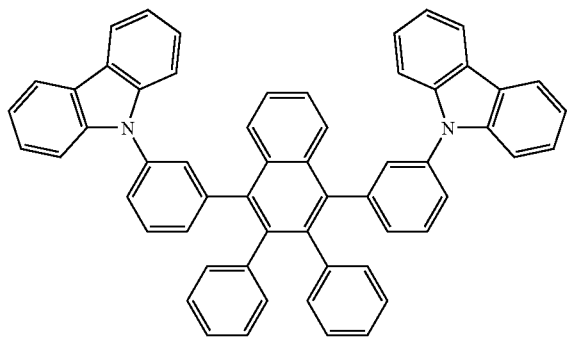
[Formula 2-1]
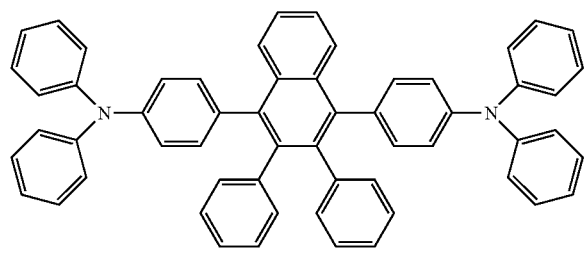
[Formula 2-2]
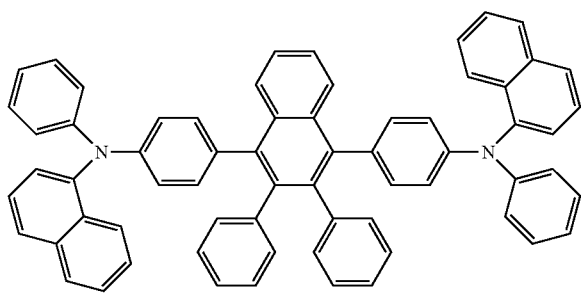
[Formula 2-3]
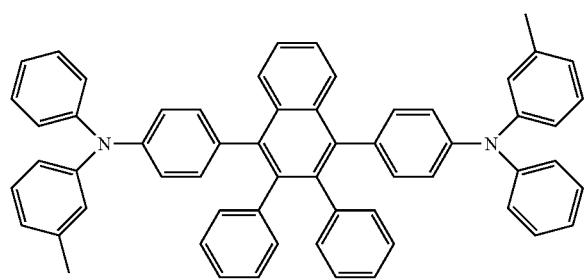
[Formula 2-4]
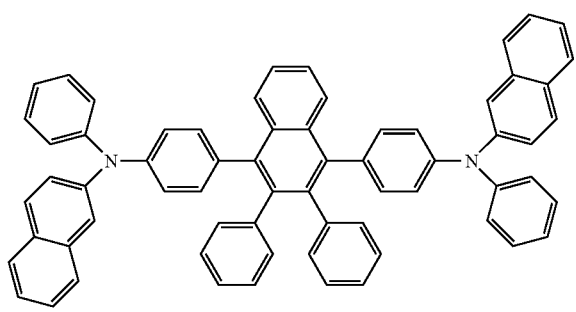
[Formula 2-5]
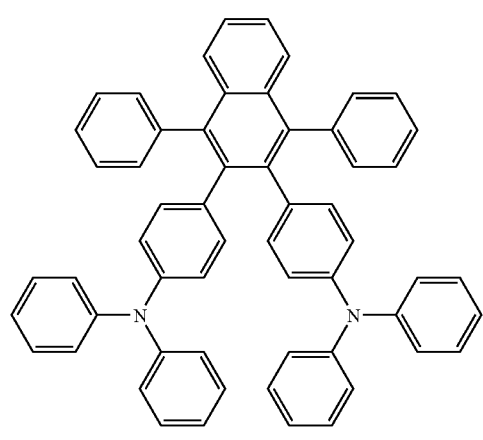
[Formula 2-6]
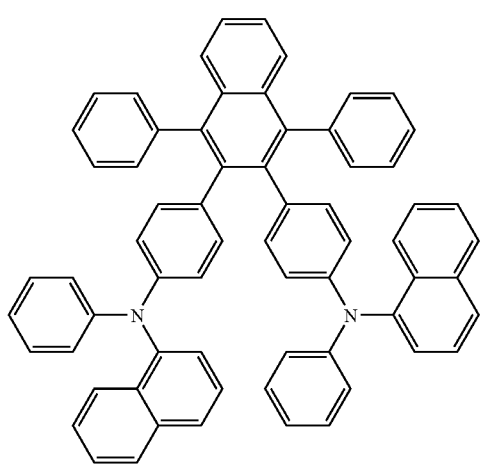

[Formula 2-7]
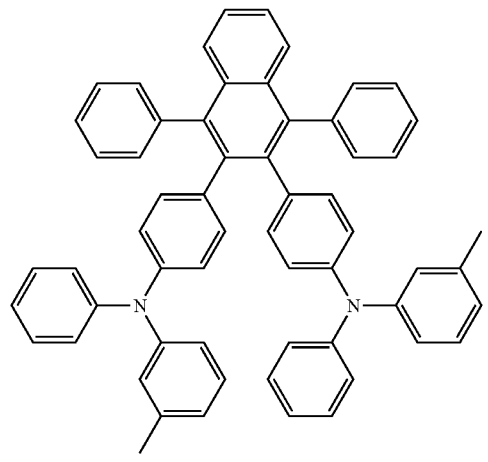
[Formula 2-8]
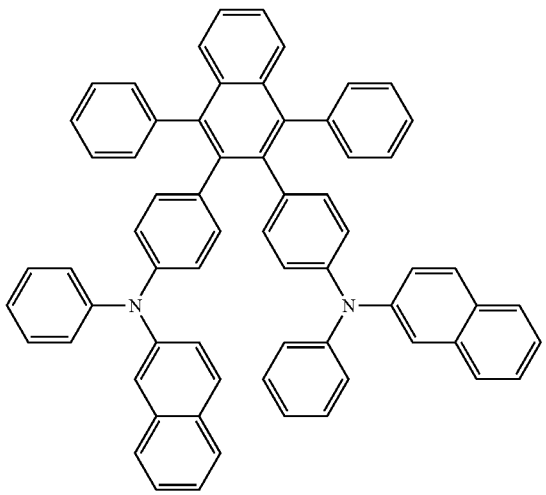
[Formula 2-9]
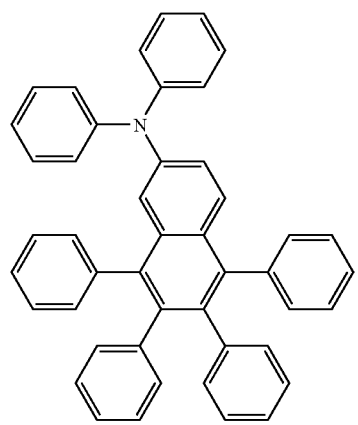
[Formula 2-10]
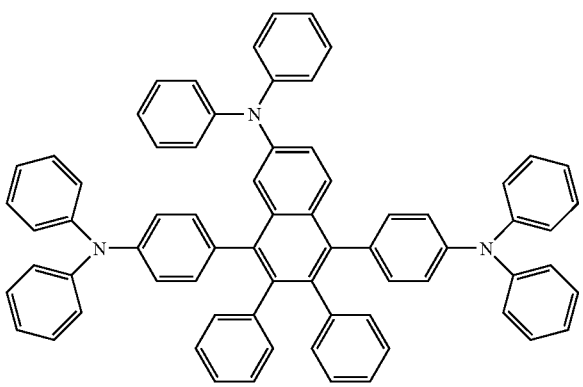
[Formula 2-11]
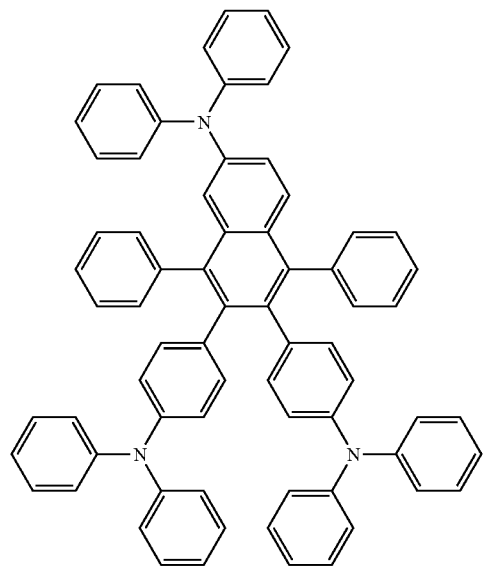
[Formula 2-12]
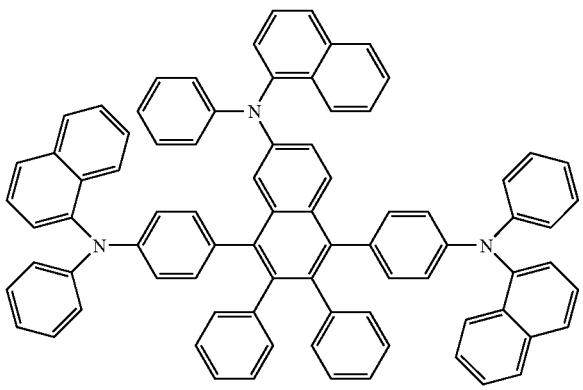

[Formula 2-13]
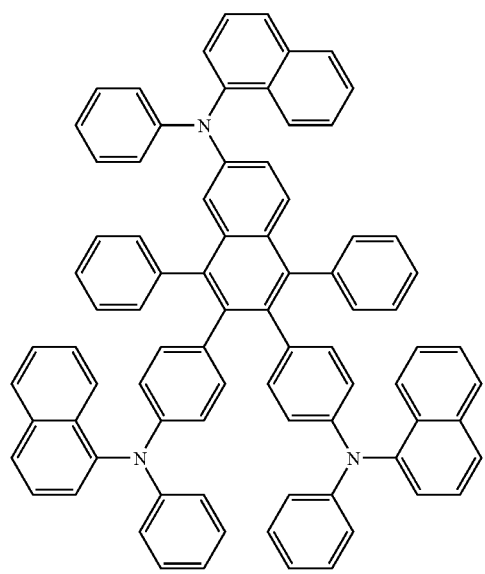
[Formula 2-14]
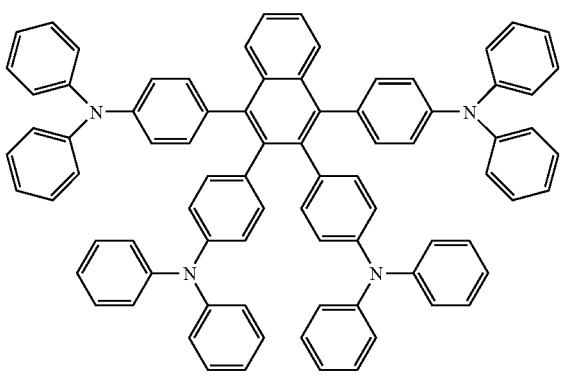
[Formula 2-15]
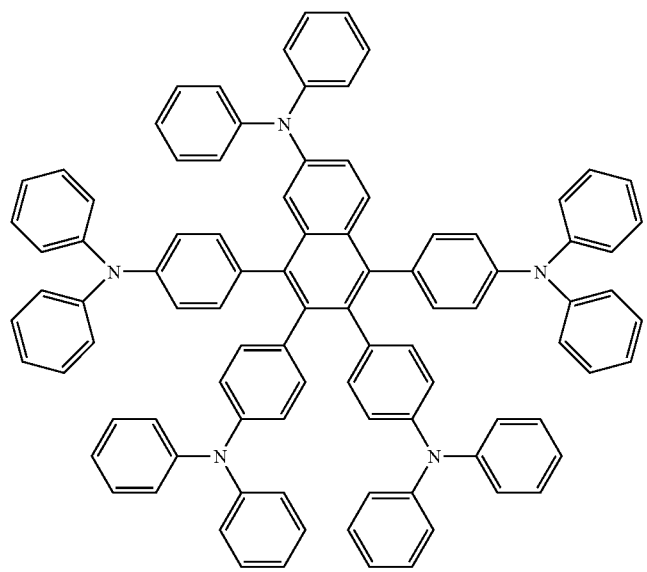
[Formula 2-16]
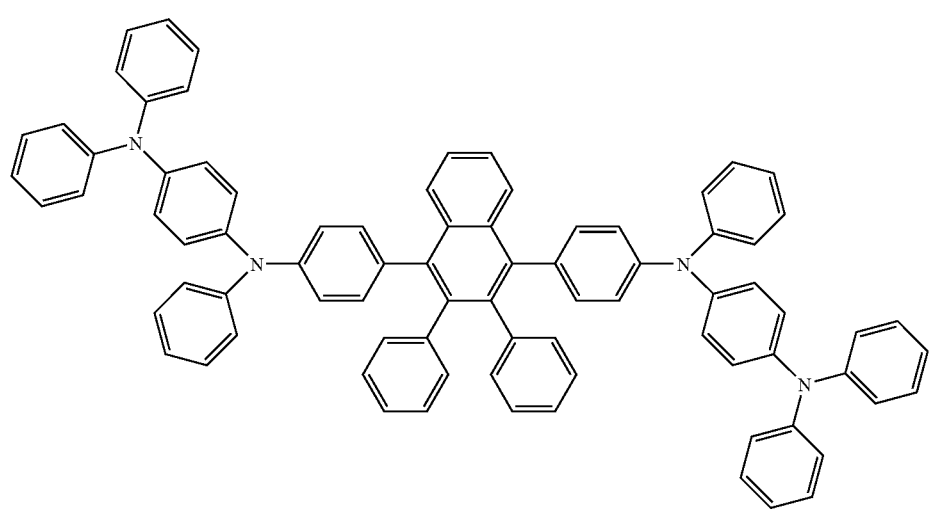

[Formula 2-17]
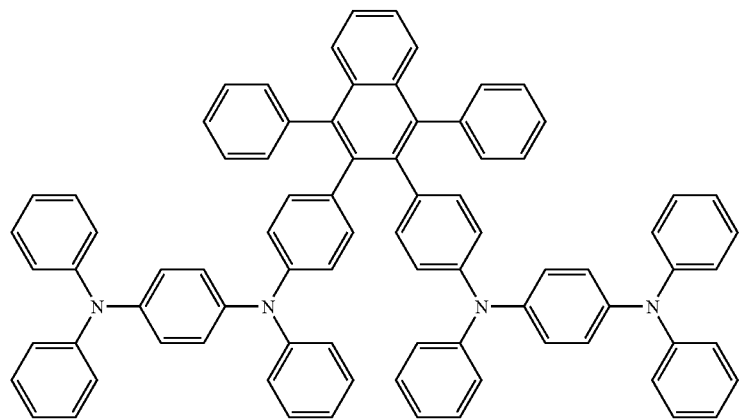
[Formula 2-18]
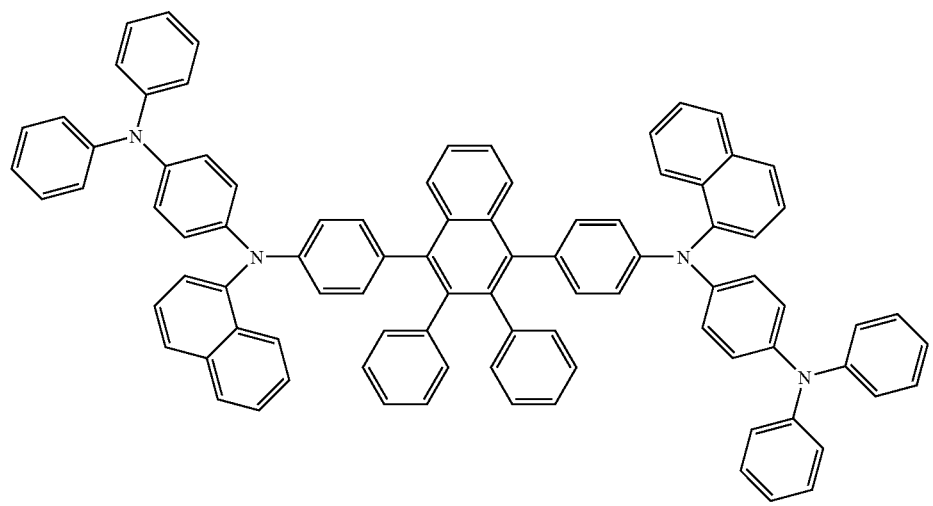
[Formula 2-19]
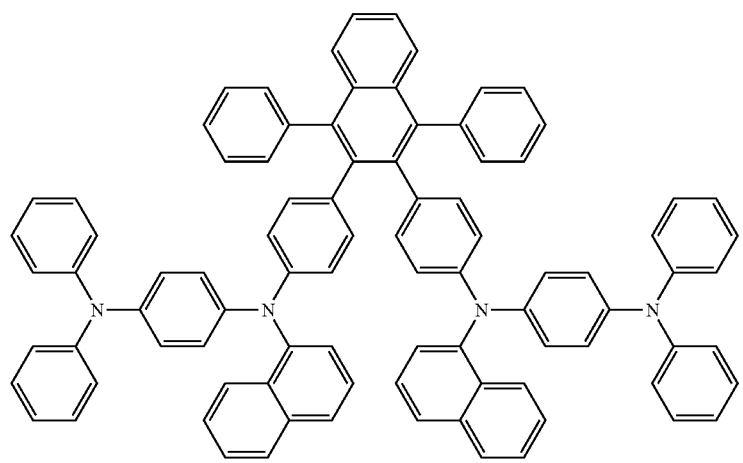

[Formula 2-20]
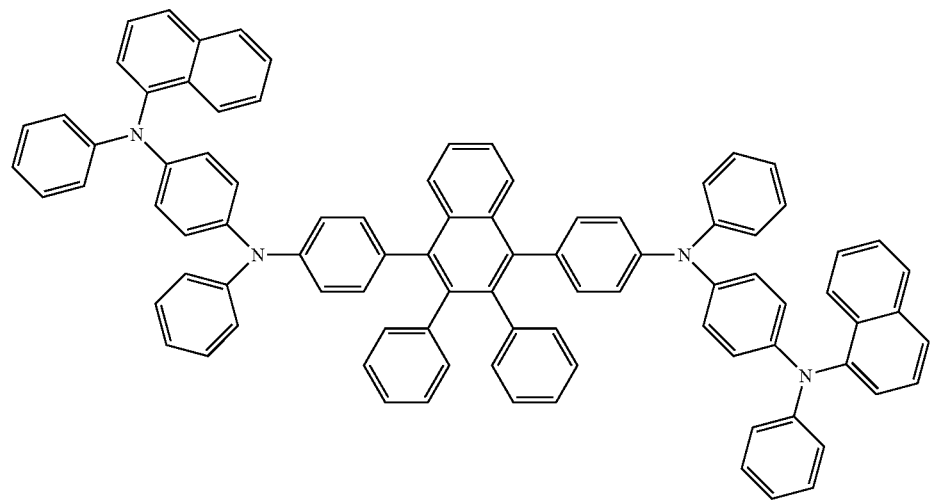
[Formula 2-21]
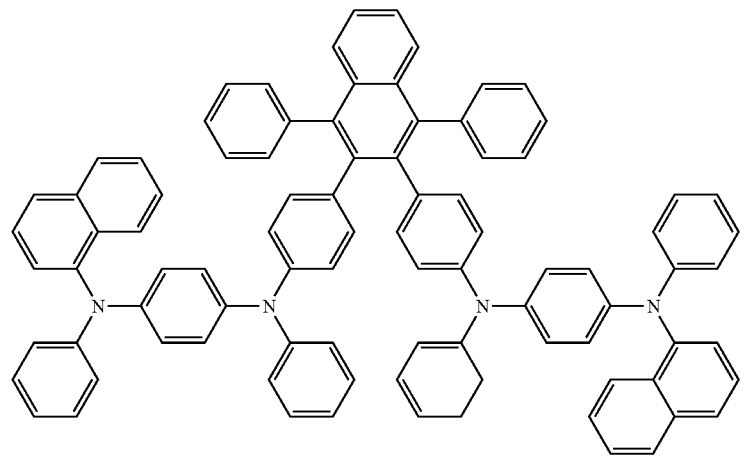
[Formula 2-22]
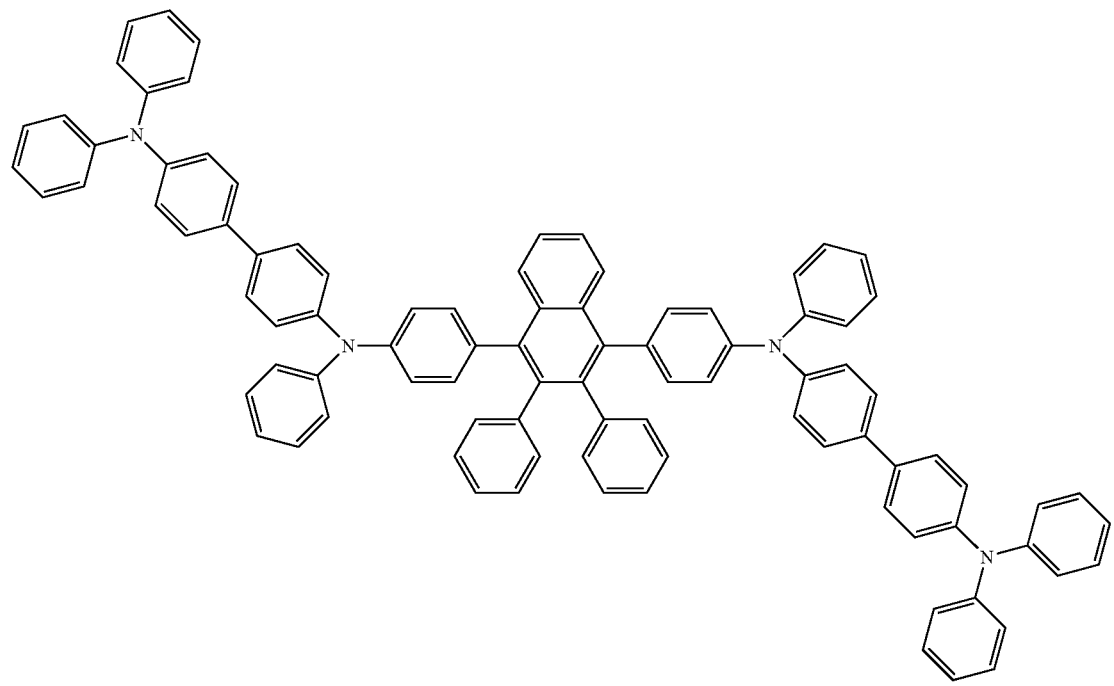

[Formula 2-23]
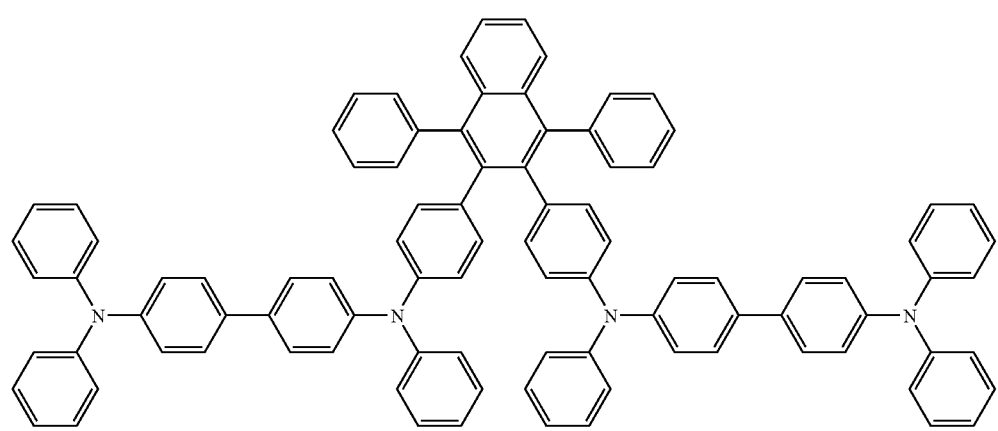
[Formula 2-24]
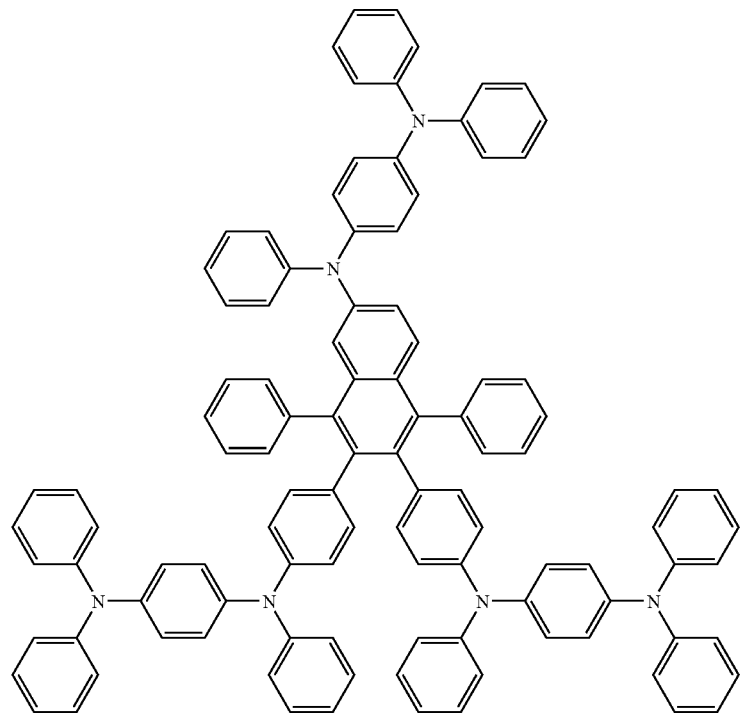
[Formula 3-1]
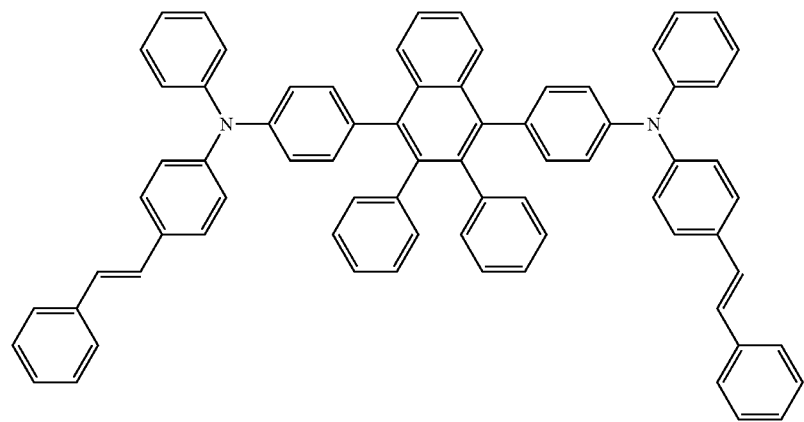

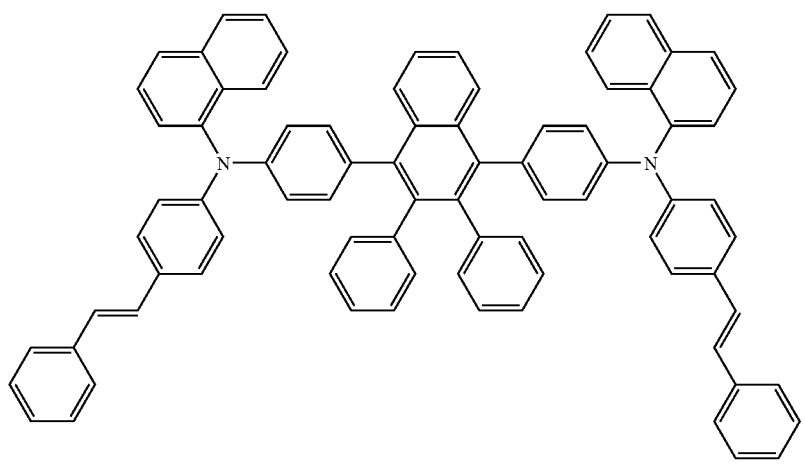
[Formula 3-2]
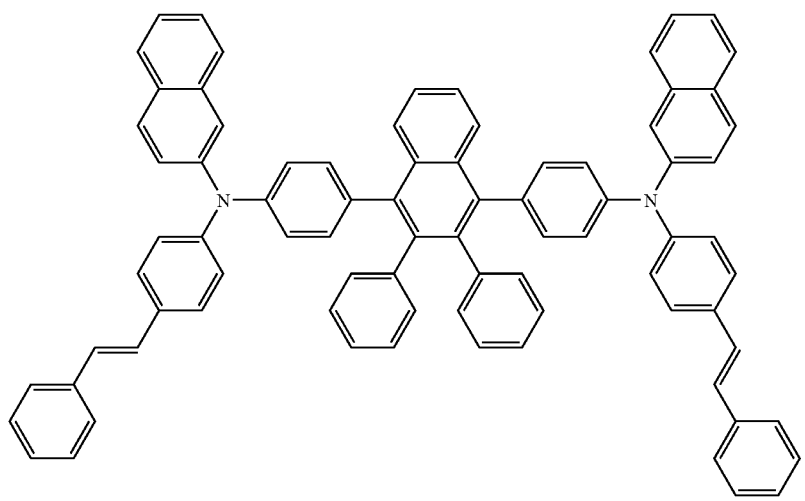
[Formula 3-3]
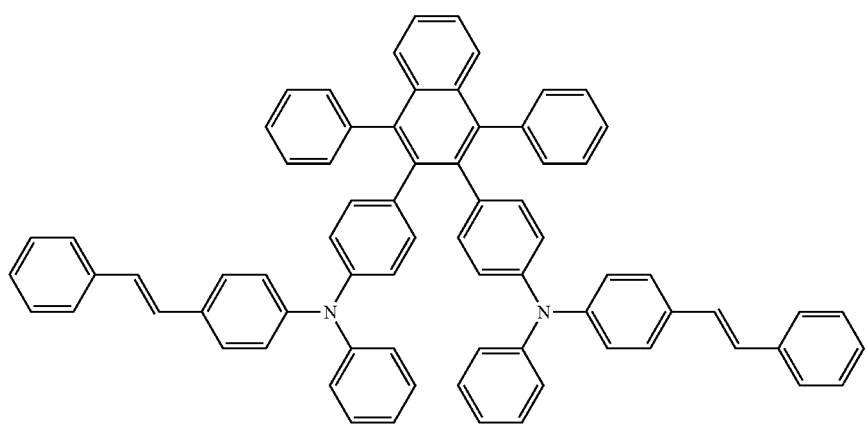
[Formula 3-4]

[Formula 3-5]
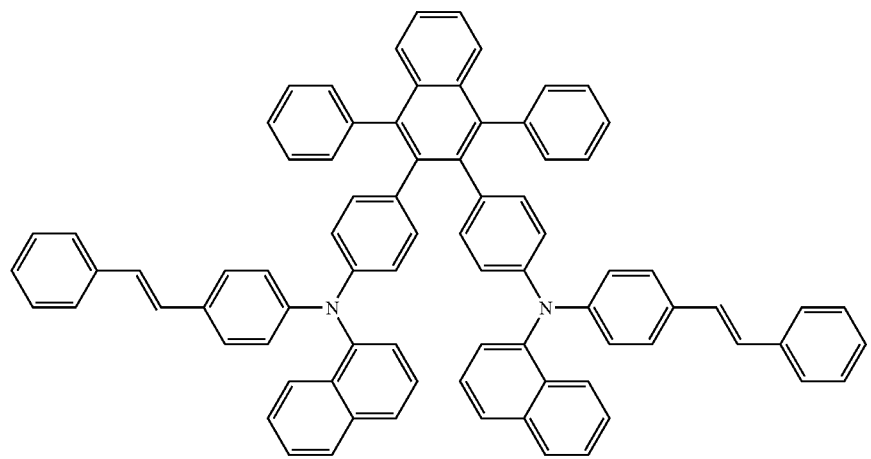
[Formula 3-6]
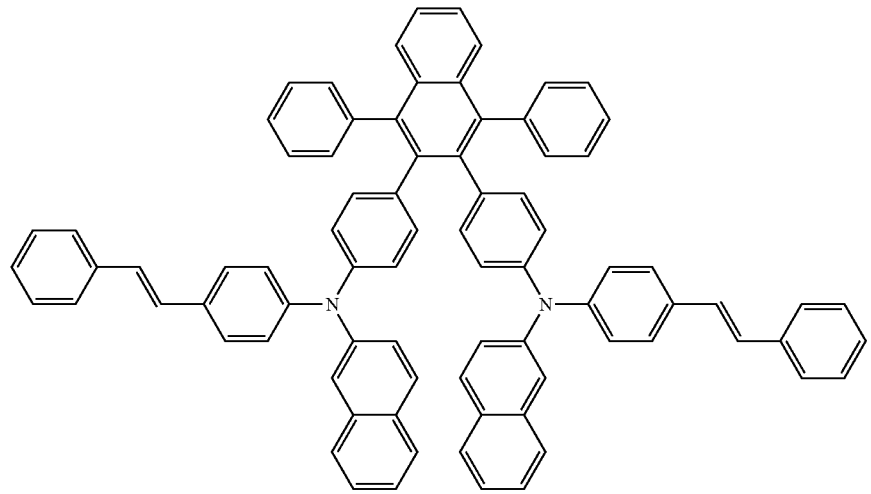
[Formula 3-7]
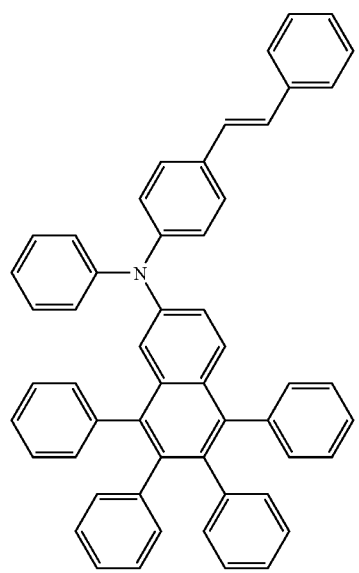

[Formula 3-8]
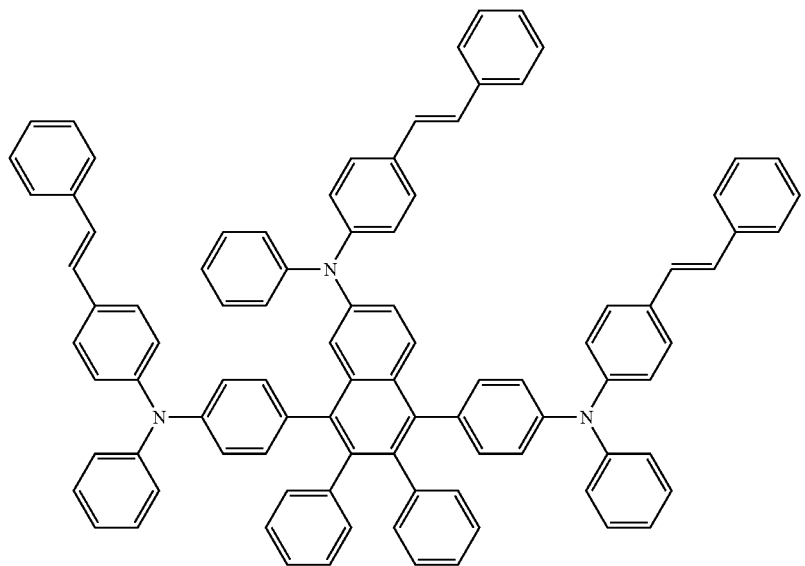
[Formula 3-9]
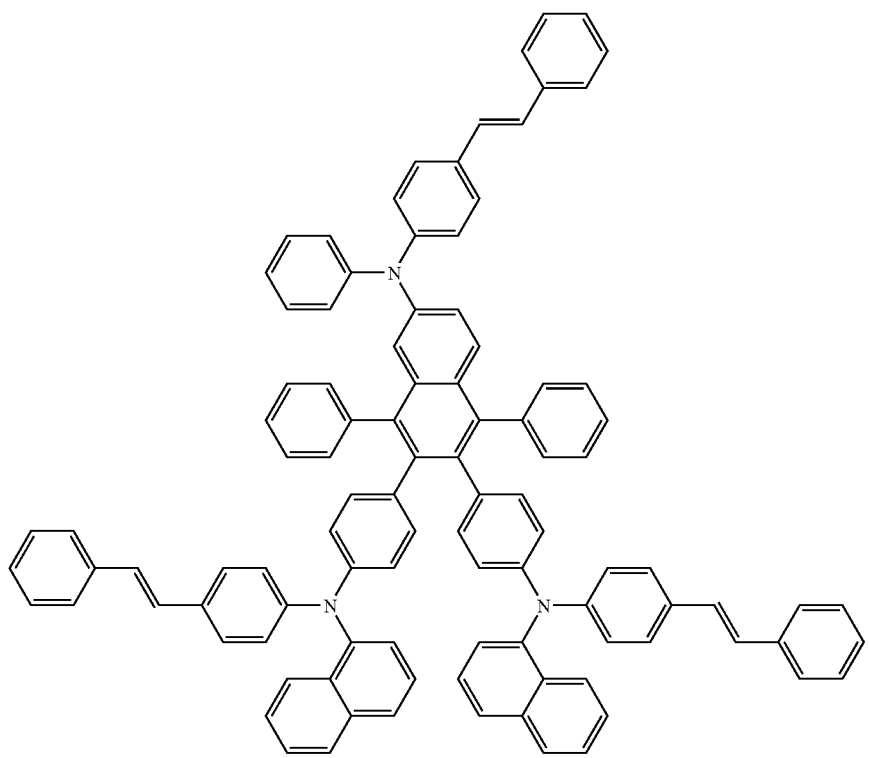
[Formula 3-10]
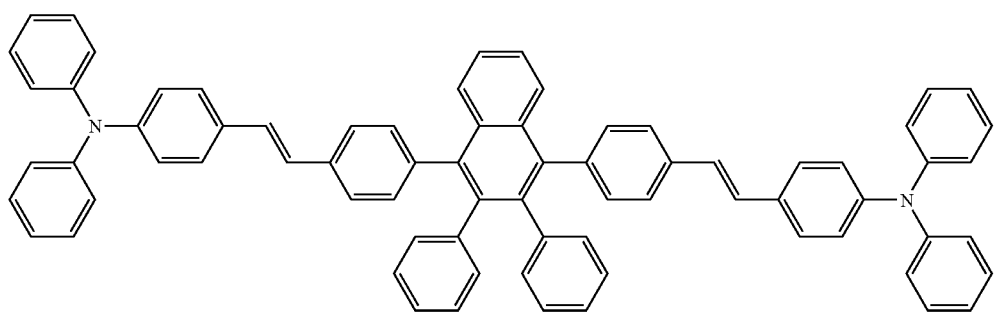

[Formula 3-11]
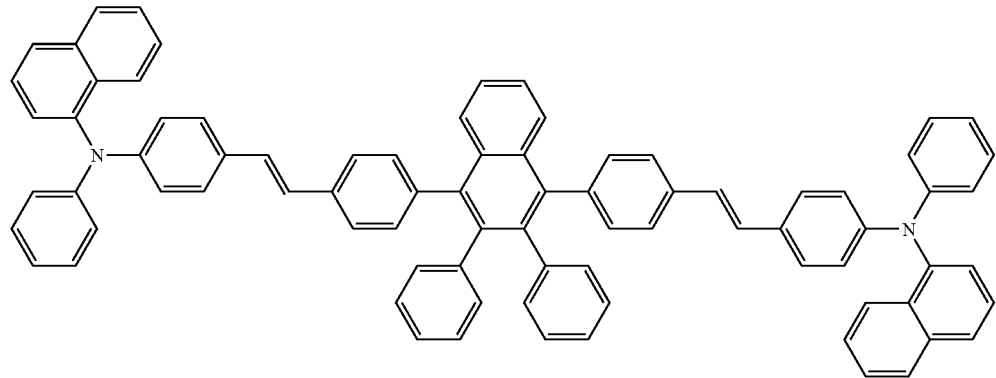
[Formula 3-12]
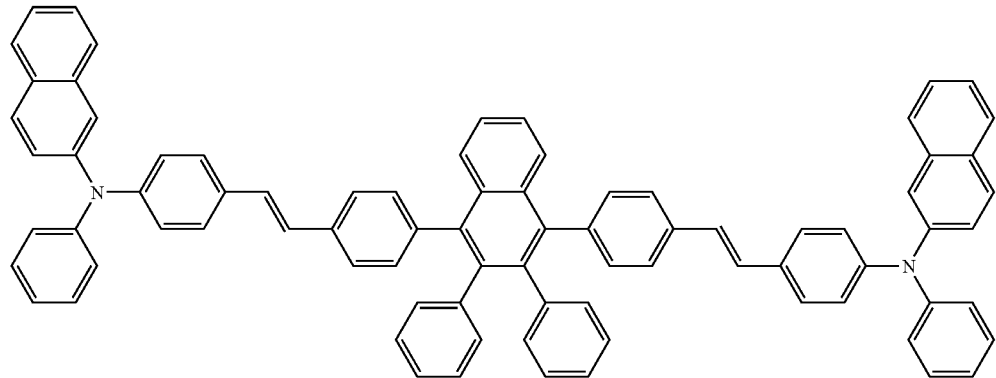
[Formula 3-13]
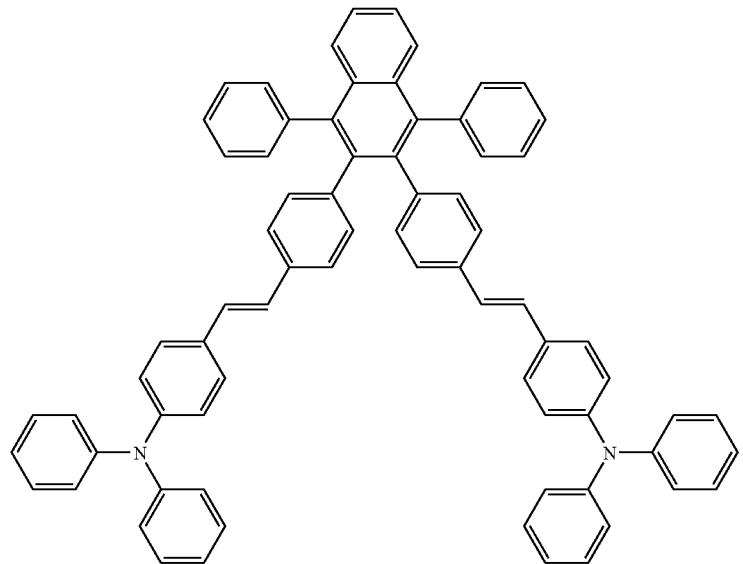

[Formula 3-14]
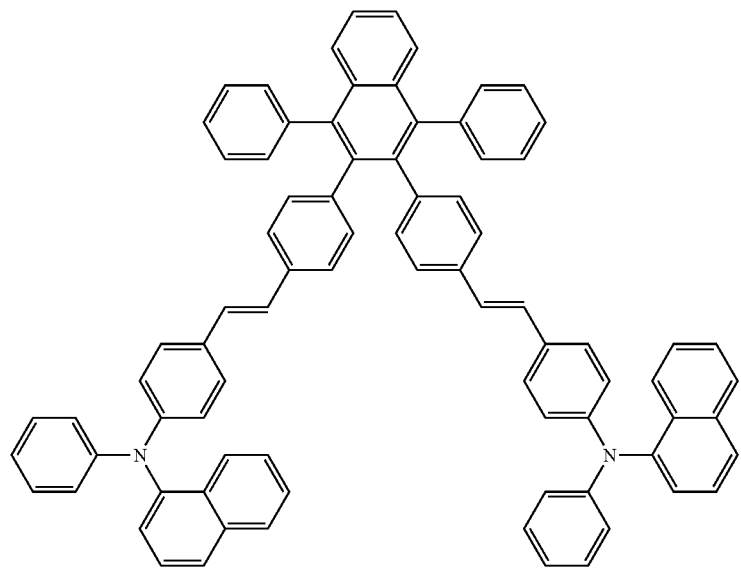
[Formula 3-15]
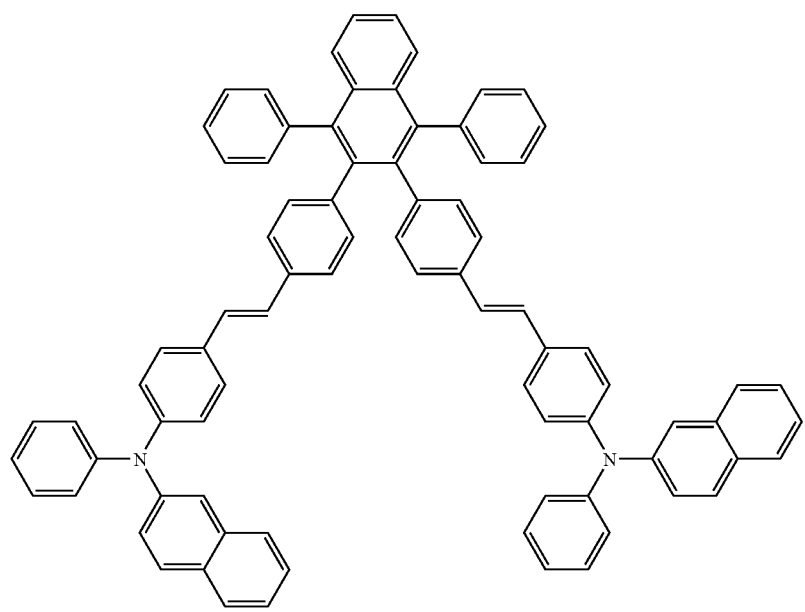
[Formula 4-1]
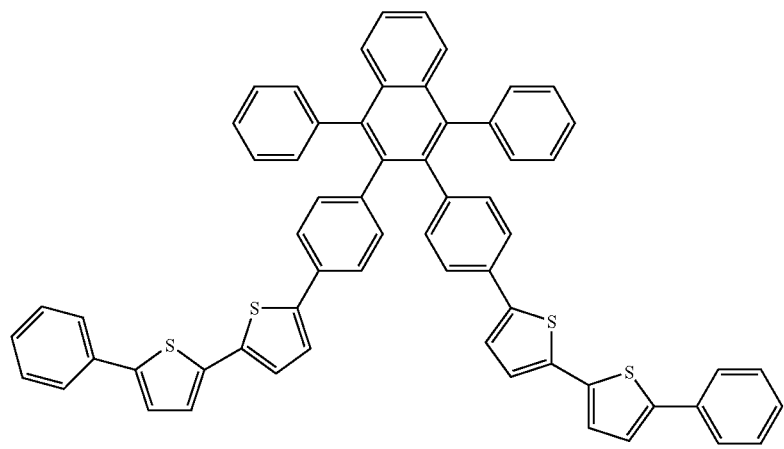

[Formula 4-2]
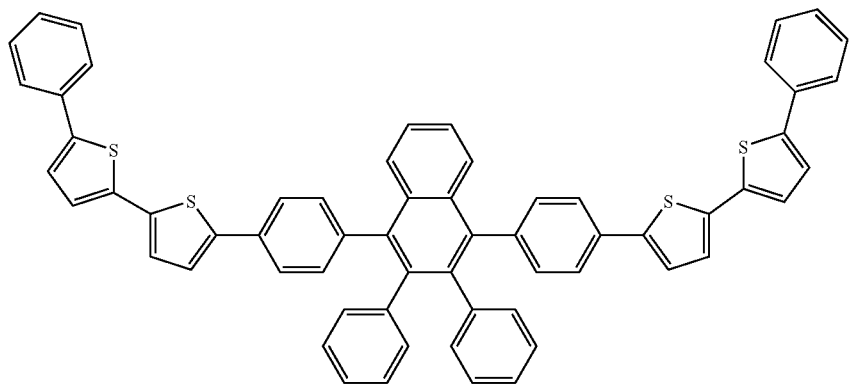
[Formula 4-3]
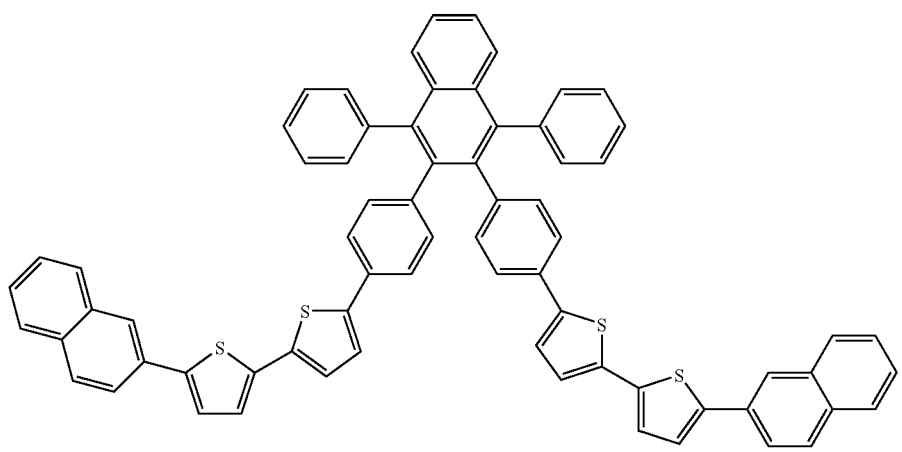
[Formula 4-4]
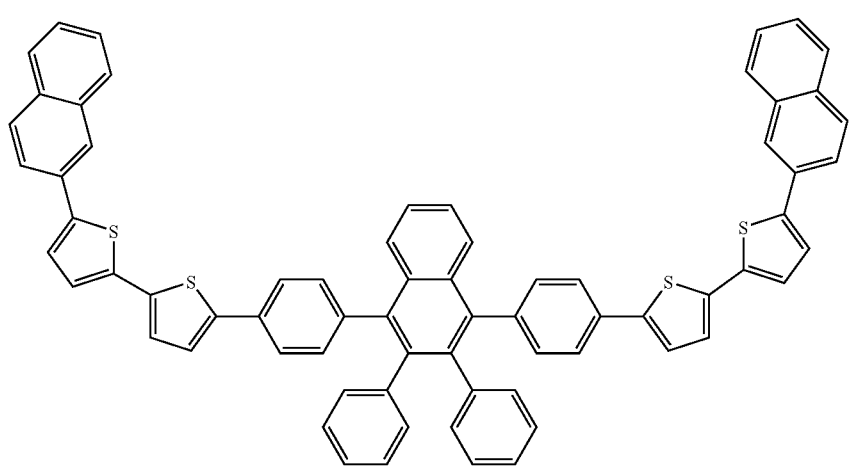

[Formula 4-5]
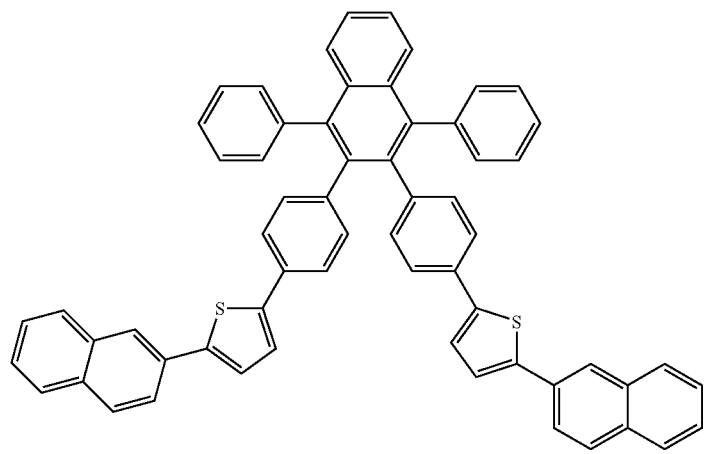
[Formula 4-6]
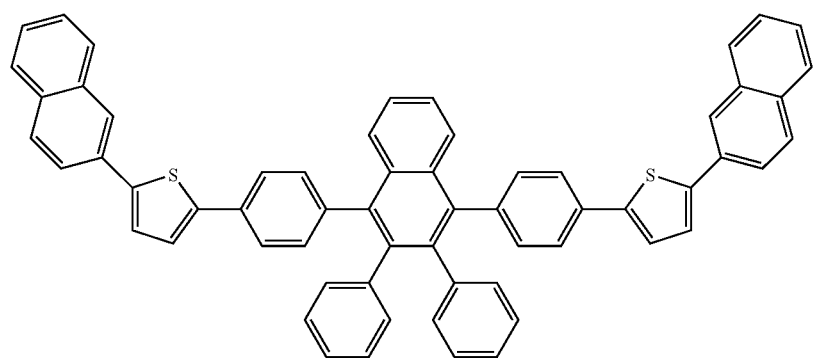
[Formula 4-7]
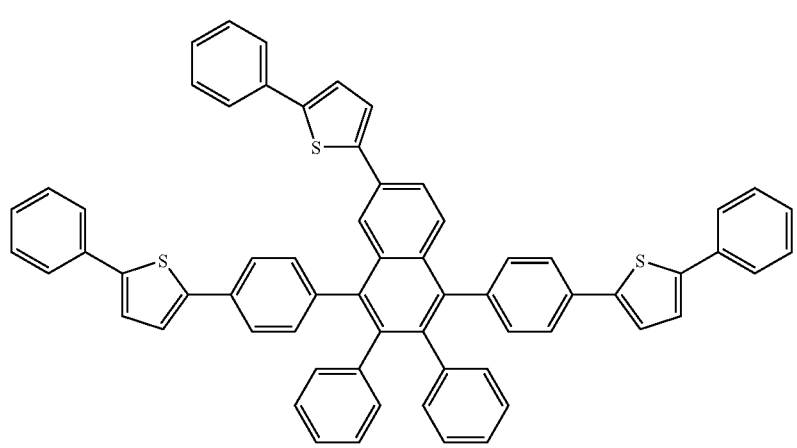

[Formula 4-8]
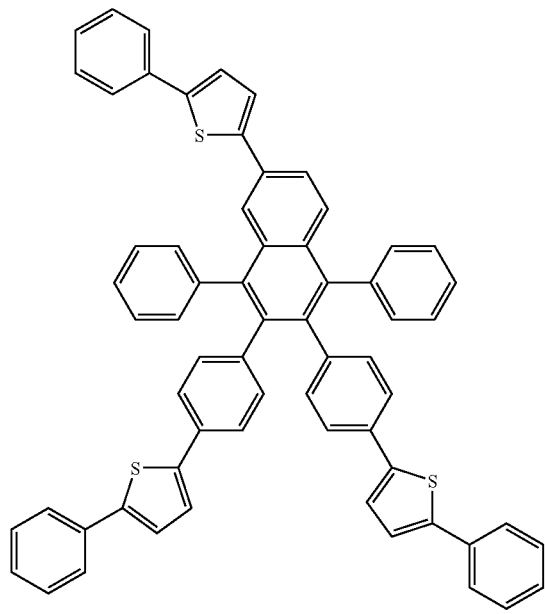
[Formula 4-9]
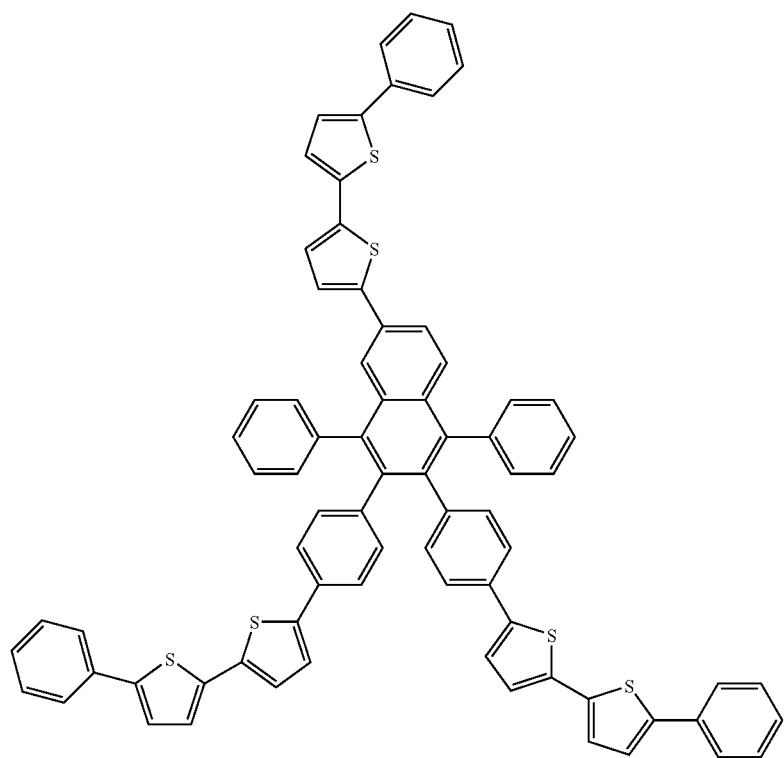

-continued
[Formula 5-1]
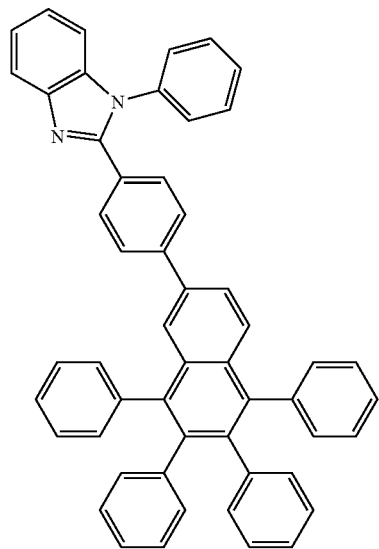
[Formula 5-2]
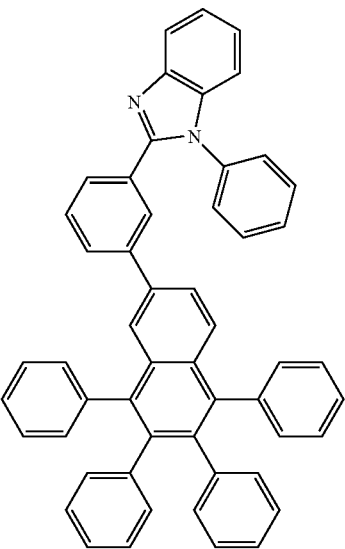
[Formula 5-3]
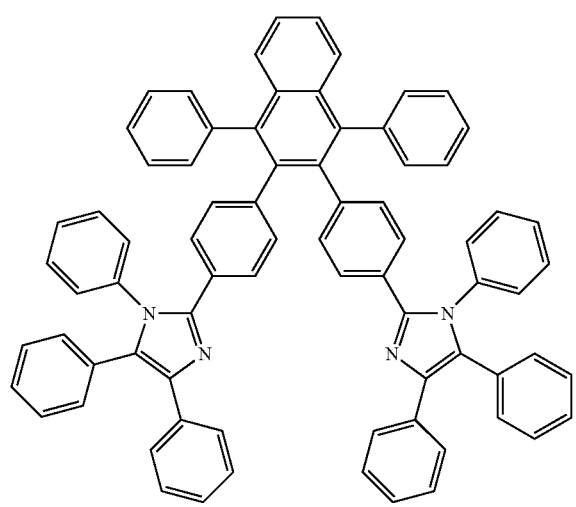
[Formula 5-4]
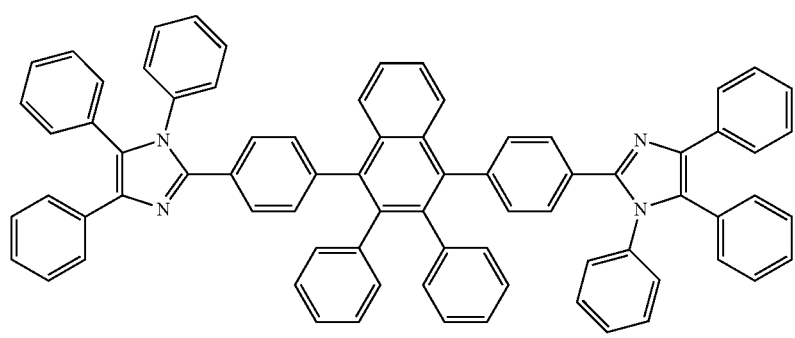

[Formula 5-5]
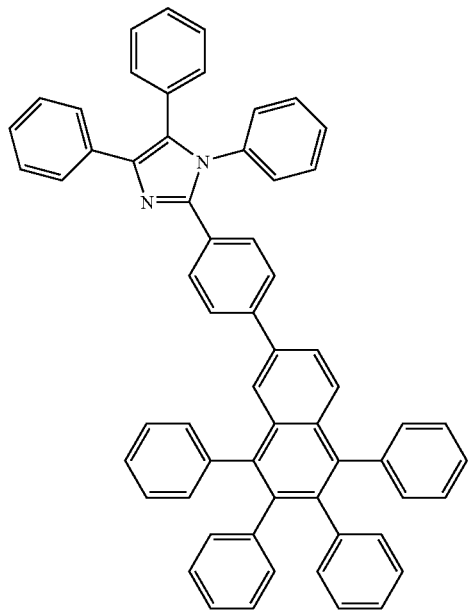
[Formula 5-6]
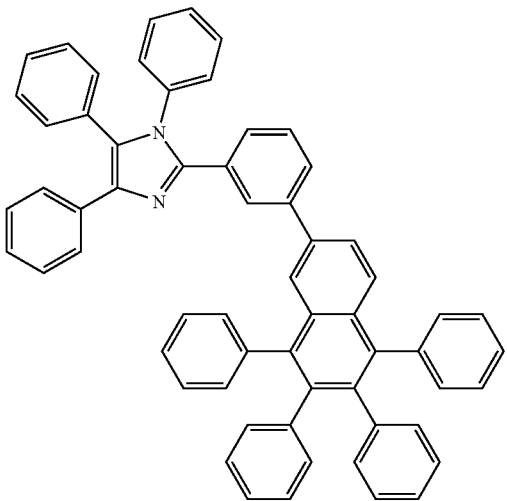
[Formula 5-7]
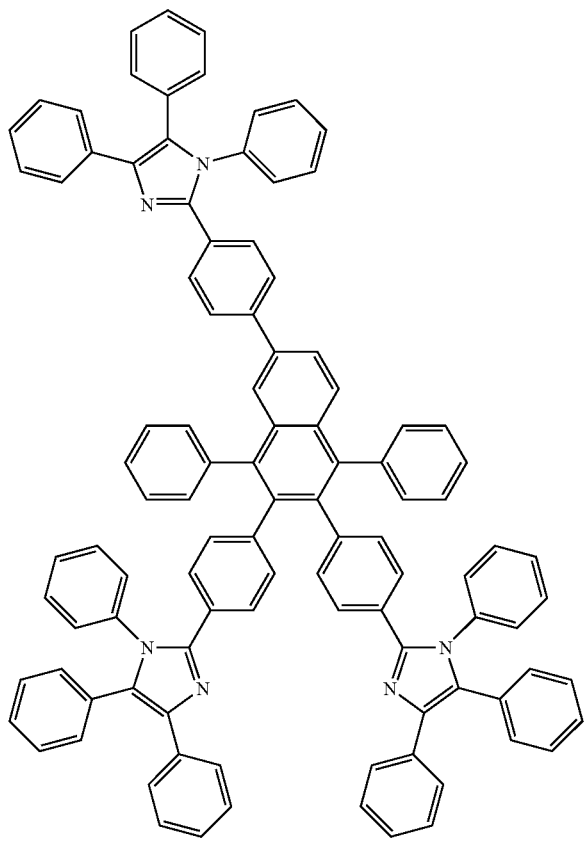

-continued
[Formula 5-8]
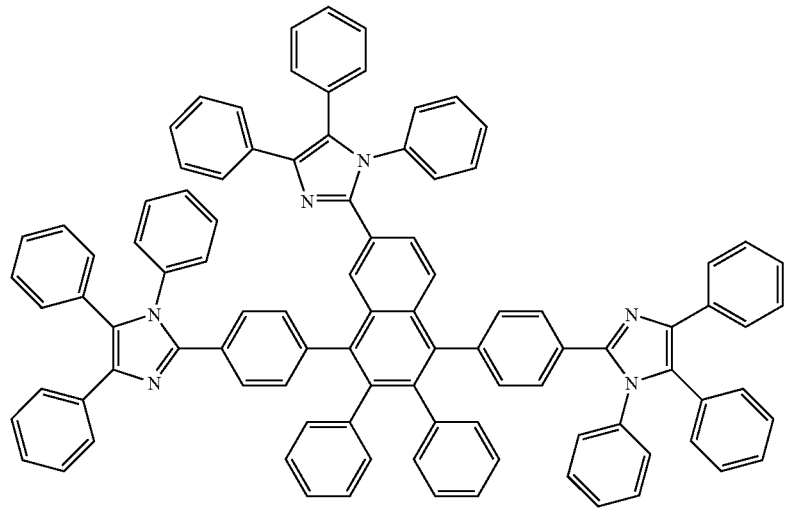
[Formula 5-9]
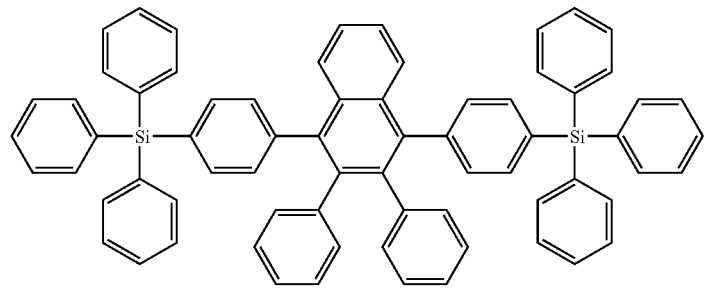
[Formula 5-10]
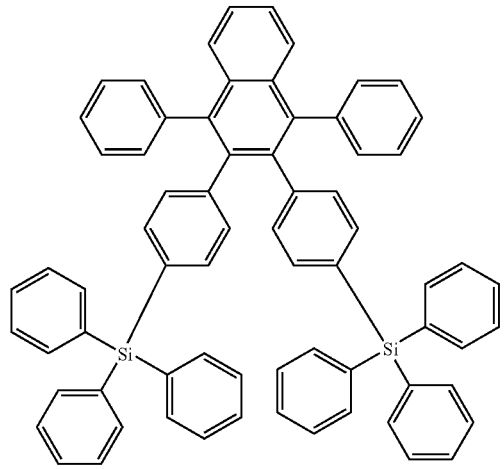
[Formula 5-11]
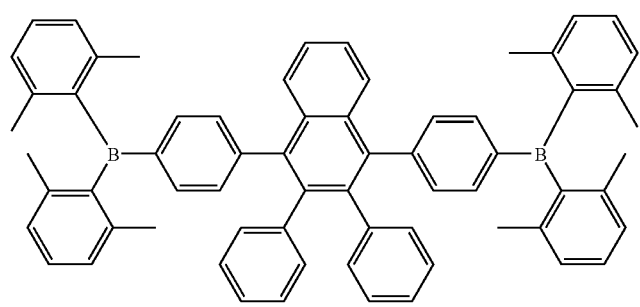

[Formula 5-12]
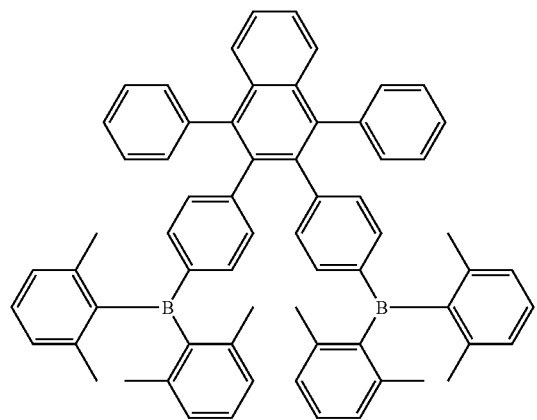
[Formula 5-13]
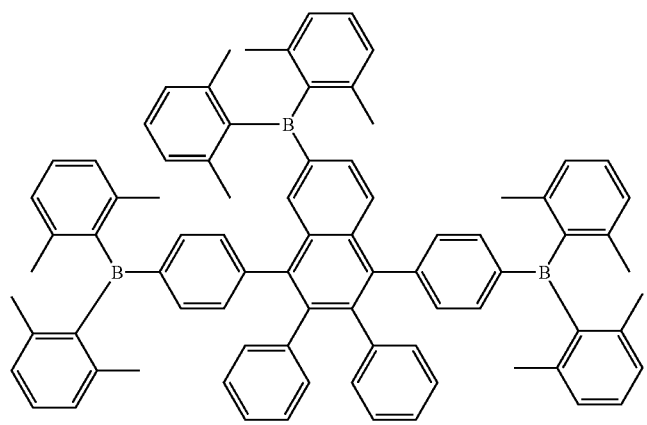
[Formula 5-14]
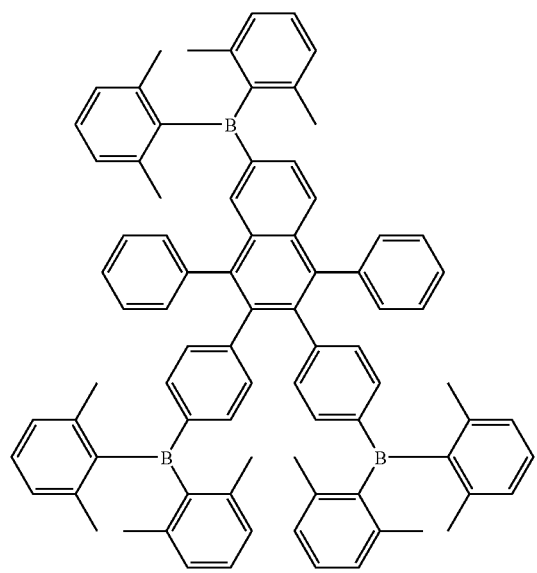

[Formula 5-15]
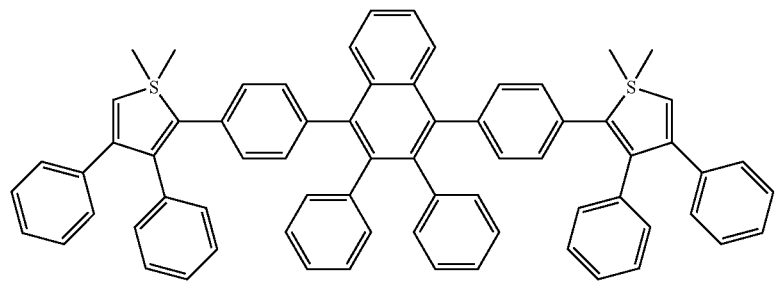
[Formula 5-16]
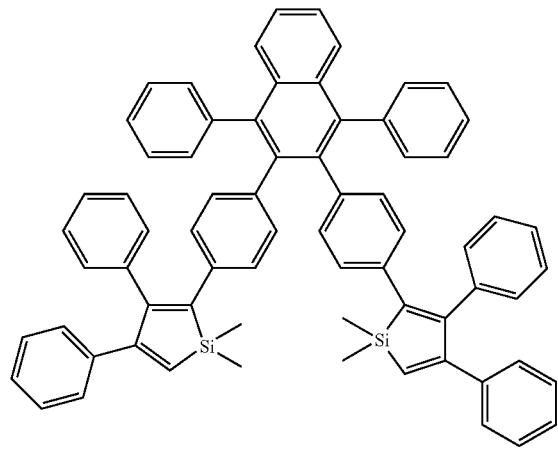
[Formula 5-17]
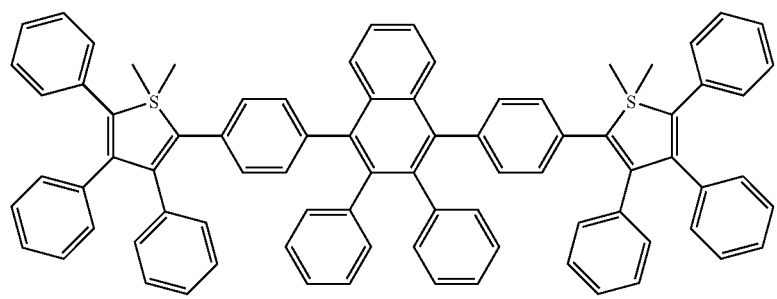
[Formula 5-18]
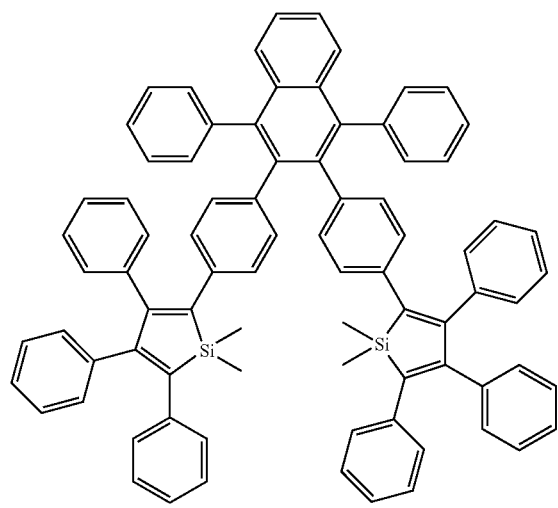
[Formula 6-1]
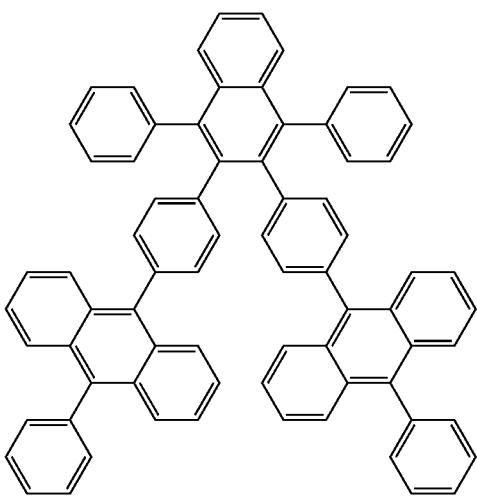

-continued

[Formula 6-2]

[Formula 6-3]

[Formula 6-4]

[Formula 6-5]

-continued
[Formula 6-6]
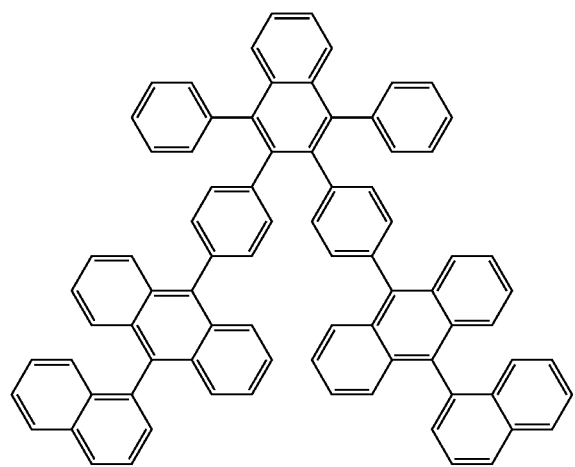
[Formula 6-7]
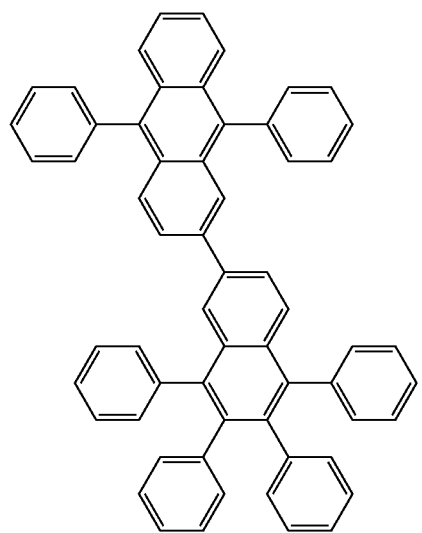
[Formula 6-8]
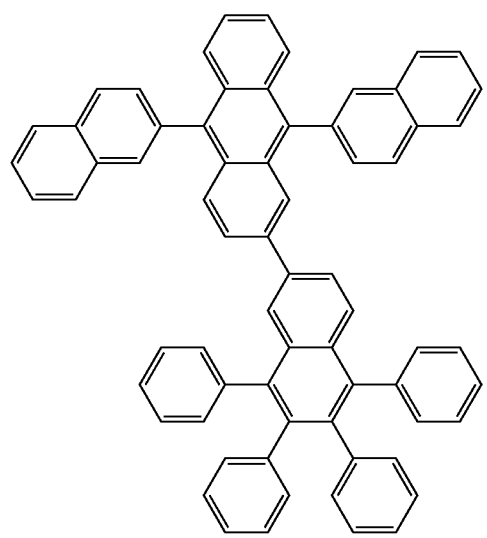
[Formula 6-9]
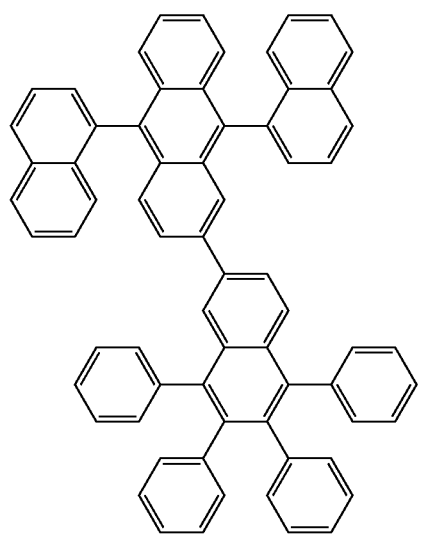
[Formula 6-10]
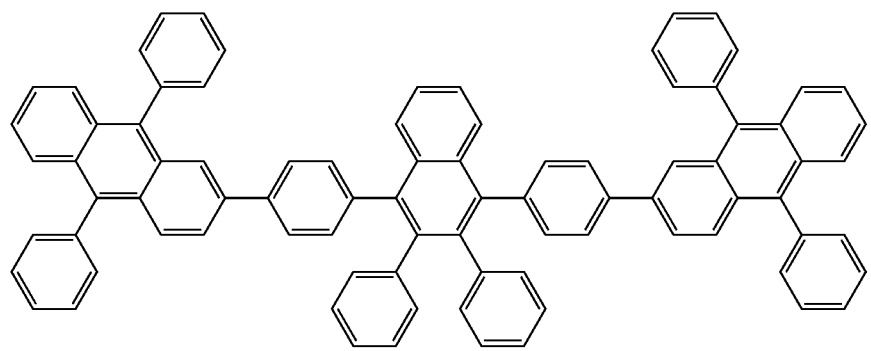

[Formula 6-11]
[Formula 6-12]
[Formula 6-13]
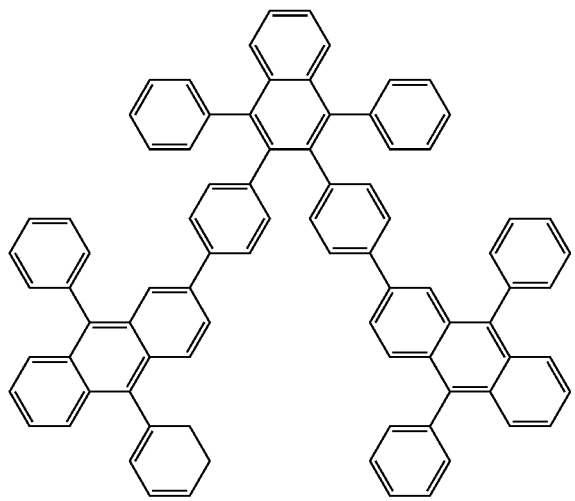

[Formula 6-14]
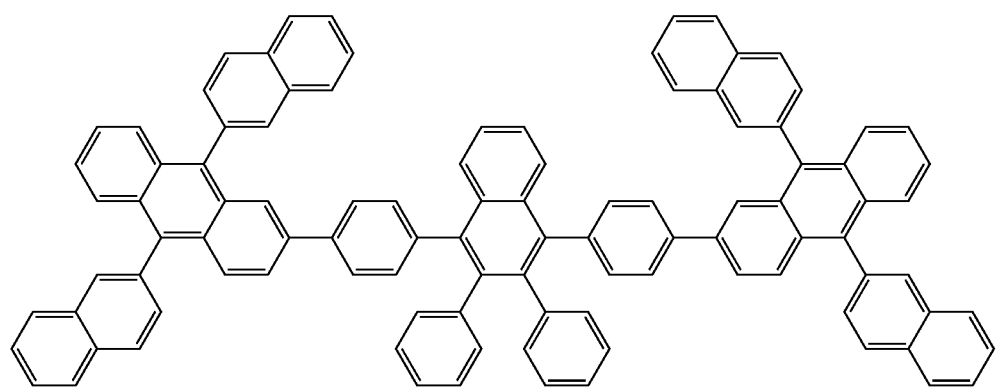
[Formula 6-15]
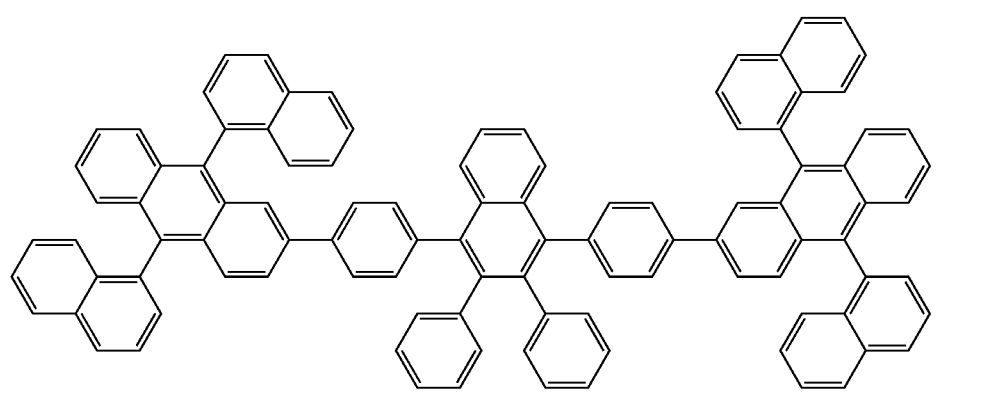
The compound of Formula 1 can be prepared, for example, as follows. Intermediate materials of Formulae a to g can be prepared using starting materials of Formulae h to k.
Intermediate Materials
[Formula a]
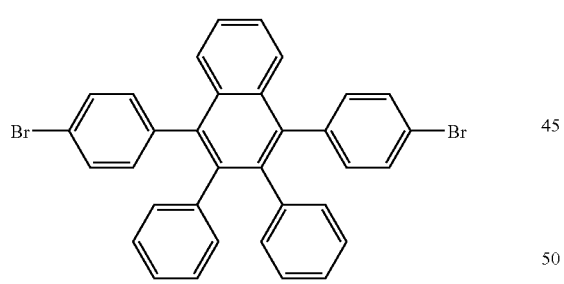
[Formula b]
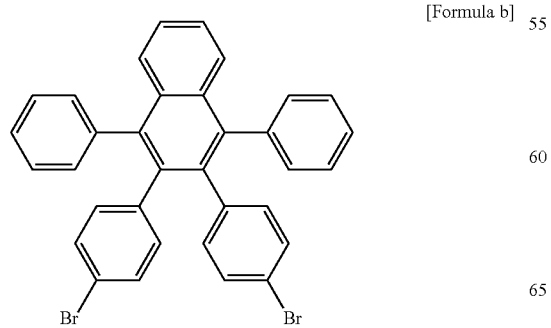
-continued
[Formula c]
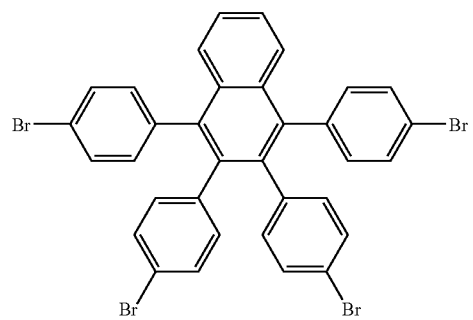
[Formula d]
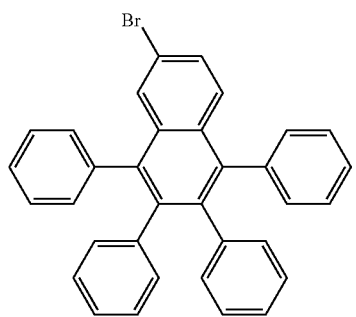

55
-continued

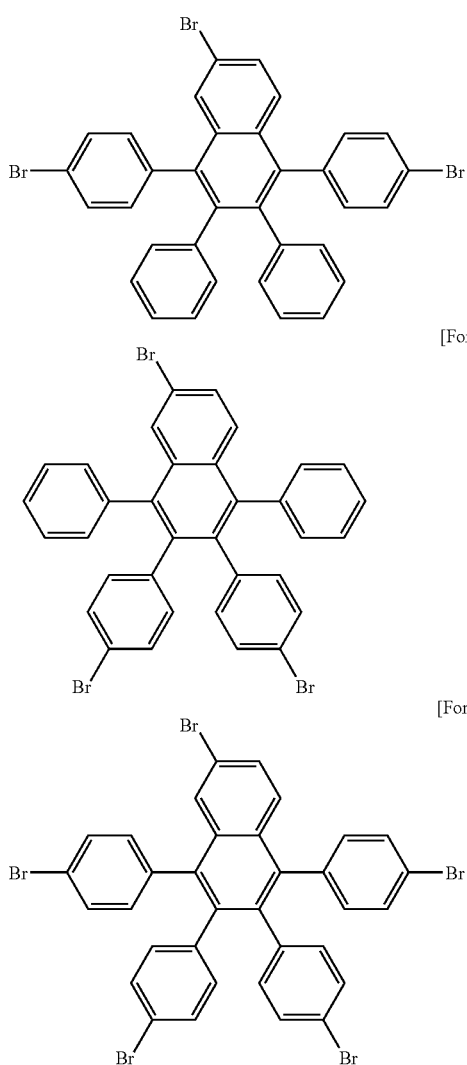

[Formula e]

[Formula f]

[Formula g]

Starting Material

56
-continued

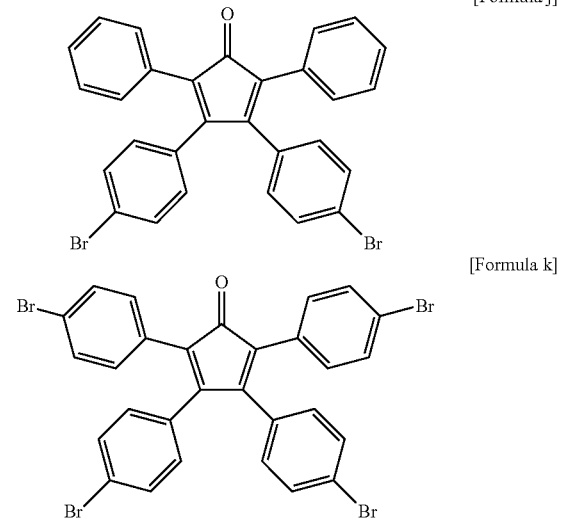

[Formula j]

[Formula k]

Specifically, according to one embodiment of the present invention, the starting materials of Formulae h to k and isoamyl nitrite are dissolved in dichloroethane, and refluxed under stirring. Anthranylic acid or 2-amino 5-bromobenzoic acid dissolved in dichloroethane are added dropwise thereto to prepare intermediate materials of Formulae a to g.

Subsequently, the intermediate materials are added to toluene with a precursor of substituent to be substituted to the compound of Formula 1, sodium t-butoxide, Pd(dba)$_2$, and P(t-Bu)$_3$, and are subject to reaction. The mixture is added to a mixed solution of THF and H$_2$O. The organic layer is separated from the mixture, dried and concentrated. The residue was purified by column chromatography and then recrystallized from dichloromethane and ethanol to obtain a compound of Formula 1.

The compound of Formula 1 is a novel structure of a tetraphenylnaphthalene derivative, and can be used as various materials for an organic material layer in an organic light emitting device due to its structural properties. This will be described in detail, below.

The steric core structure of the compound of Formula 1, for convenience of explanation, can be divided into three portions, A, B, and C, as shown in the following Formula.

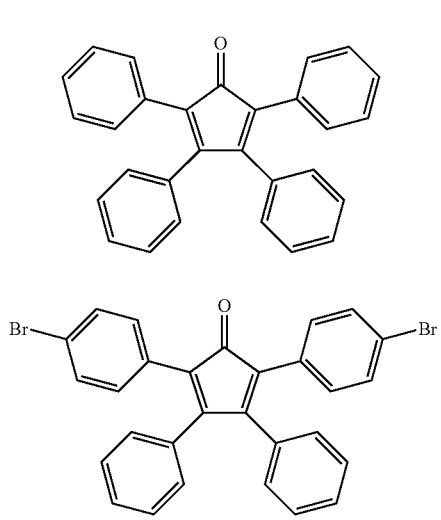

[Formula h]

[Formula i]

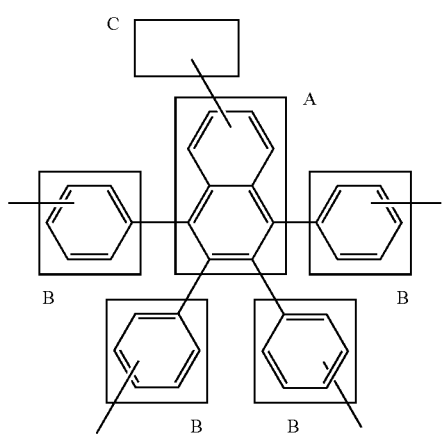

The compound of Formula 1 has the steric core structure in which a portion A, naphthalene bonds to portion B's, benzene rings with spiro bonding.

The three-dimensional structure of the organic material minimizes pi-pi interaction in the organic materials, thereby formation of excited excimers and or excited exciplex is prevented.

On the other hand, the conjugation length of the compound has a close relationship with an energy band gap. In detail, the energy band gap is reduced as the conjugation length of the compound increases. However, in the case where the conjugation length increases, even if the conjugated portions are not planar, the conjugations of the compound are reduced. As described above, since a conjugation structure between a portion A and a portion B is limited in the core structure of the compound of Formula 1, the core structure has a large energy band gap.

Various substituent groups are introduced to $R_{11}$ to $R_{55}$ positions of the core structure having the large energy band gap so as to produce compounds having various energy band gaps. Generally, it is easy to control the energy band gap by introducing substituent groups into a core structure having a large energy band gap, but it is difficult to significantly control the energy band gap by introducing substituent groups into a core structure having a small energy band gap.

Substituent groups are introduced into portion B's, benzene rings, so as to easily produce compounds having a large energy band gap due to the above-described steric structure. Such structural properties of the compound of Formula 1 are advantageous in that the compound of Formula 1 can be applied to a phosphorescent or fluorescent blue host or dopant, an electron injecting or transporting material, a hole injecting or transporting material. On the other hand, substituent groups are introduced into a portion C, the portion C has less steric structure than the portion B. Therefore, if various substituent groups are introduced into a portion C, it is easy to make a band gap small, whereby the compound of Formula 1 can be advantageously applied to a green or red host or dopant.

As described above, various substituent groups are introduced to a portion B and a portion C in the compound of Formula 1 so as to produce compounds having various band gaps. Accordingly, substituent groups are introduced into the core structure of the compound of Formula 1 so as to produce substances capable of satisfying requirements of each organic layer, such as hole injecting or transporting layer, light emitting layer, and electron injecting or transporting layer in the organic light emitting device. Further, in the present invention, the compound having the proper energy level is selected depending on the substituent group among the compounds represented by Formula 1 to be used in the organic light emitting device, thereby it is possible to realize a device having a low drive voltage and a high optical efficiency.

The present invention provides an organic electronic device comprising a first electrode, a second electrode, and organic material layers interposed therebetween, in which at least one layer of the organic material layers comprises the compound of Formula 1.

Figure 2:
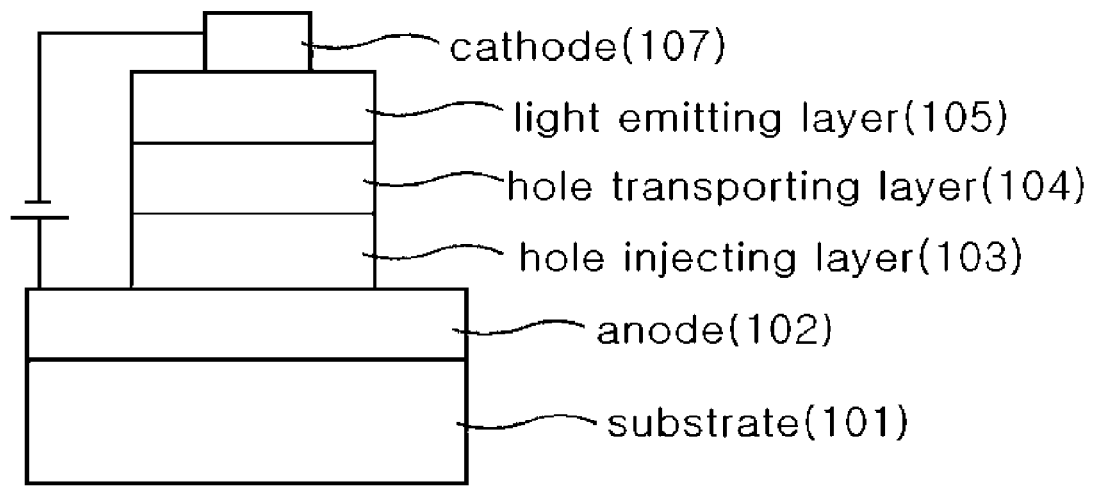
Figure 3:
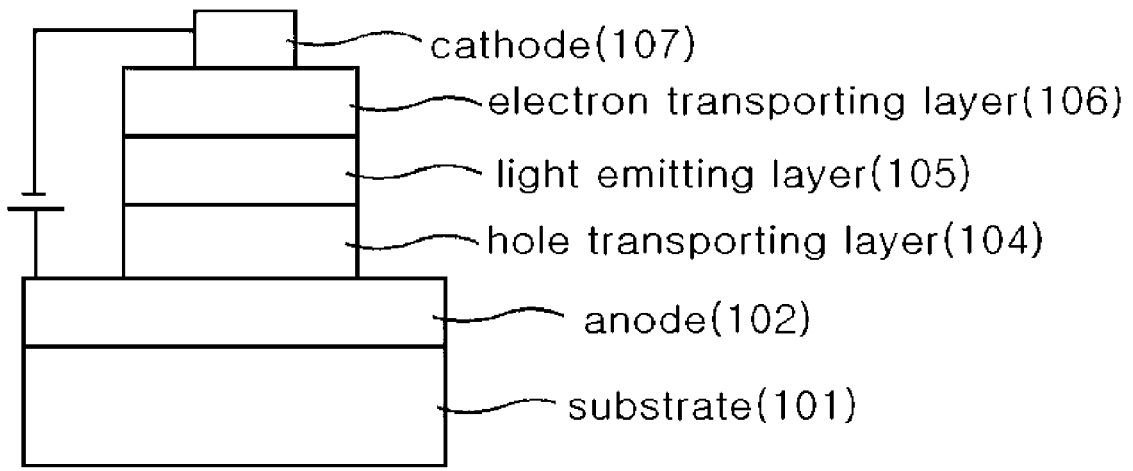
Figure 4:
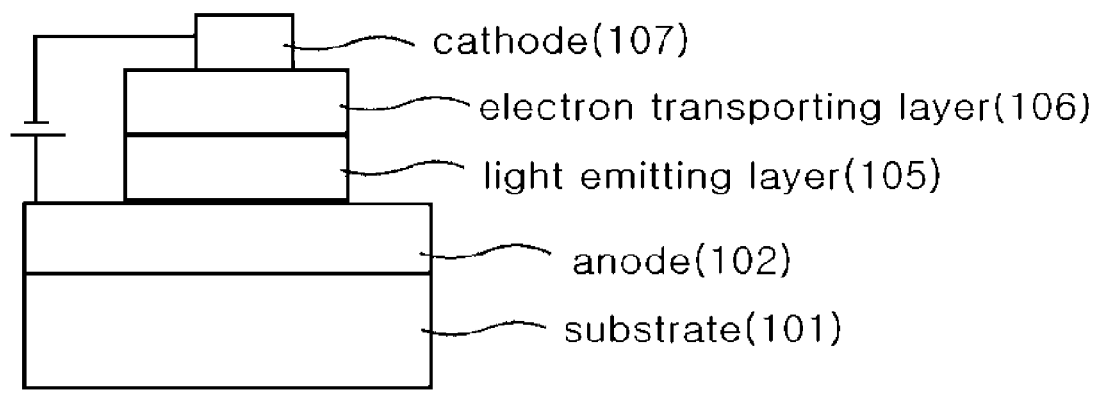
Figure 5:
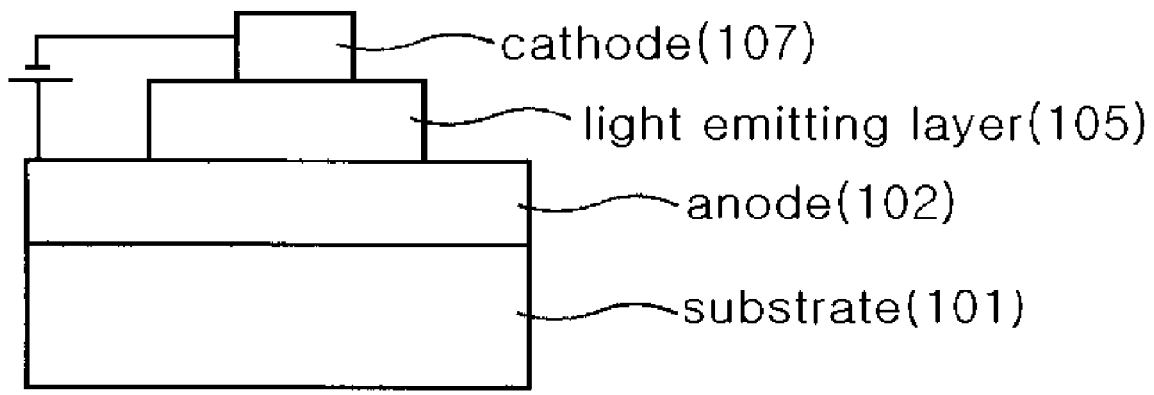

The organic light emitting device according to the present invention can be prepared as a general structure by usual methods and materials known in the art, except that the compound of Formula 1 are used to form at least one organic material layer. The structures of the organic light emitting device according to the present invention are illustrated in FIGS. 1 to 5, but are not limited thereto.

For example, the organic light emitting device according to the present invention can be prepared by depositing a metal, a metal oxide having conductivity or an alloy thereof on a substrate using a PVD (physical vapor deposition) process such as sputtering and e-beam evaporation to form an anode; forming an organic material layer comprising a hole injecting layer, a hole transporting layer, a light emitting layer, and an electron transporting layer on the anode; and depositing a material, which can be used as a cathode, thereon.

Alternatively, the organic light emitting device can be prepared by sequentially depositing a cathode material, an organic material layer, and an anode material on a substrate (see PCT Patent Application Publication WO 2003/012890). The organic material layer may be of a multilayer structure containing a hole injecting layer, a hole transporting layer, a light emitting layer, an electron transporting layer, and the like, but not limited thereto, and may be of a monolayer structure. Further, the organic material layer can be produced to have a fewer number of layers, by using a variety of polymeric materials, by means of a solvent process rather than a deposit process, such as spin coating, dip coating, doctor blading, screen printing, ink jet printing, and heat transfer processes.

The anode material is preferably a material having a large work function to facilitate hole injection usually to an organic material layer. Specific examples of the anode material which can be used in the present invention include metals such as vanadium, chromium, copper, zinc and gold, or an alloy thereof; metal oxides such as zinc oxide, indium oxide, indium-tin oxide (ITO), and indium zinc oxide (IZO); a combination of a metal and an oxide such as ZnO:Al and $SnO_2$:Sb; conductive polymers such as poly(3-methylthiophene), poly[3,4-(ethylene-1,2-dioxy)thiophene] (PEDT), polypyrrole and polyaniline, but not limited thereto.

The cathode material is preferably a material having a small work function to facilitate electron injection usually to an organic material layer. Specific examples of the cathode material include metals such as magnesium, calcium, sodium, potassium, titanium, indium, yttrium, lithium, gadolinium, aluminum, silver, tin and lead, or an alloy thereof; multilayer structure materials such as LiF/Al and $LiO/Al_2$, but not limited thereto.

The hole injecting material is a material facilitating hole injection from an anode at low voltage. The HOMO (highest occupied molecular orbital) level of the hole injecting material is preferably located between the work function of the anode materials and the HOMO level of its neighboring organic material layer. Specific examples of the hole injecting material include organic materials of metal porphyrin, oligothiophene and arylamine series, organic materials of hexanitrile hexaazatriphenylene and quinacridone series, organic materials of perylene series, and conductive polymers of anthraquinone, polyaniline, and polythiophene series, but are not limited thereto.

The hole transporting material is preferably a material having high hole mobility, which can transfer holes from the anode or the hole injecting layer toward the light emitting layer. Specific examples thereof include organic materials of arylamine series, conductive polymers and block copolymers having both conjugated portions and non-conjugated portions, but are not limited thereto.

The light emitting material are a material capable of emitting visible light by accepting and recombining holes from the hole transporting layer and electrons from the electron transporting layer, preferably a material having high quantum efficiency for fluorescence and phosphorescence. Specific examples thereof include 8-hydroxyquinoline aluminum complex ($Alq_3$); compounds of carbazole series; dimerized styryl compounds; BAlq; 10-hydroxybenzoquinoline-metal compounds; compounds of benzoxazole, benzthiazole and benzimidazole series; polymers of poly(p-phenylenevinylene) (PPV) series; spiro compounds; and compounds of polyfluorene and rubrene series, but are not limited thereto.

The electron transporting material is suitably a material having high electron mobility, which can transfer electrons from the cathode to the light emitting layer. Specific examples thereof include 8-hydroxyquinoline aluminum complex ($Alq_3$); complexes including $Alq_3$; organic radical compounds; and hydroxyflavone-metal complexes, but are not limited thereto.

The organic light emitting device according to the invention may be of a front-side, backside or double-sided light emission according to the materials used.

Mode for the Invention

Hereinafter, the present invention will be described in detail in the following Preparative Examples and Experimental Examples. However, the following Preparative Examples and Experimental Examples are set forth to illustrate, but are not to be construed to limit the present invention.

PREPARATIVE EXAMPLE

Preparation of Starting Material

Preparation of Starting Material Represented by Formula h

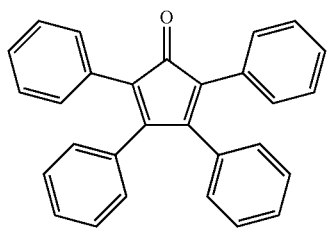

[Formula h]

After benzyl (8.4 g, 40 mmol) and diphenylacetone (8.4 g, 40 mmol) were dissolved in 250 mL of ethanol and heated, the mixture was refluxed under stirring for 1 hour. KOH (2.2 g, 40 mmol) dissolved in 20 mL of ethanol was slowly added dropwise thereto, and then refluxed under stirring for 30 minutes. The resultant was slowly cooled to give a dark red solid powder. The obtained dark red solid powder was filtered under reduced pressure, and then dried under vacuum to obtain a starting material represented by Formula h (4.5 g, 30%).

MS [M+H] 385

Preparation of starting material represented by Formula i

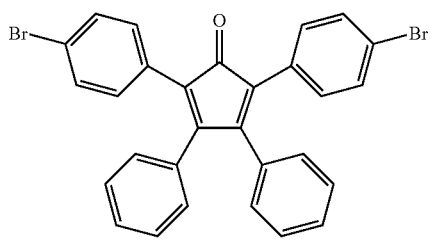

[Formula i]

After benzyl (1.14 g, 5.4 mmol) and di(4-bromophenyl)acetone (2.0 g, 5.4 mmol) were dissolved in 40 mL of ethanol and heated, the mixture was refluxed under stirring for 1 hour. KOH (0.3 g, 5.4 mmol) dissolved in 10 mL of ethanol was slowly added dropwise thereto, and then refluxed under stirring for 30 minutes. The resultant was slowly cooled to give a dark red solid powder. The obtained dark red solid powder was filtered under reduced pressure, and then dried under vacuum to obtain a starting material represented by Formula i.

(2.0 g, 68%); $^1$H NMR (400 MHz, DMSO-$d_6$) 7.50-7.48 (d, 4H), 7.30-7.23 (m, 6H), 7.11-7.09 (d, 4H), 6.98-6.96 (d, 4H); MS [M+H] 540, 542, 544

Preparation of Starting Material Represented by Formula j

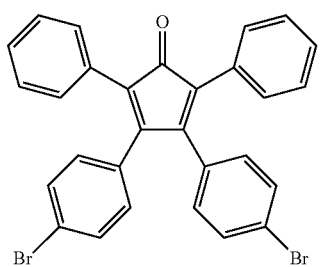

[Formula j]

After 4,4'-dibromobenzyl (9.8 g, 27 mmol) and diphenylacetone (6.2 g, 30 mmol) were dissolved in 250 mL of ethanol and heated, the mixture was refluxed under stirring for 1 hour. KOH (1.64 g, 30 mmol) dissolved in 20 mL of ethanol was slowly added dropwise thereto, and then refluxed under stirring for 30 minutes. The resultant was slowly cooled to give a dark red solid powder. The obtained dark red solid powder was filtered under reduced pressure, and then dried under vacuum to obtain a starting material represented by Formula j.

(9.0 g, 62%); $^1$H NMR (400 MHz, DMSO-$d_6$) 7.50-7.47 (d, 4H), 7.33-7.27 (m, 6H), 7.17-7.15 (d, 4H), 6.94-6.92 (d, 4H); MS [M+H] 540, 542, 544

Preparation of Starting Material Represented by Formula k

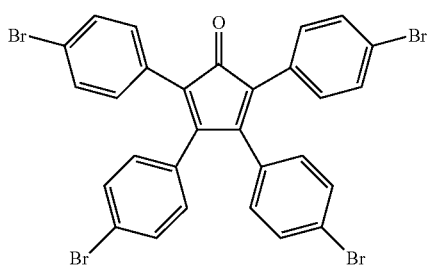

[Formula k]

Alter 4,4'-(dibromobenzyl (9.8 g, 27 mmol) and di(4-bromophenyl)acetone (2.0 g, 5.4 mmol) were dissolved in 40 mL of ethanol and heated, the mixture was refluxed under stirring for 1 hour. KOH (0.3 g, 5.4 mmol) dissolved in 10 mL of ethanol was slowly added dropwise thereto, and then refluxed under stirring for 30 minutes. The resultant was slowly cooled to give a dark red solid powder. The obtained dark red solid powder was filtered under reduced pressure, and then dried under vacuum to obtain a starting material represented by Formula k.

MS [M+H] 700

Preparation of Intermediate Material

Preparation of Intermediate Material Represented by Formula a

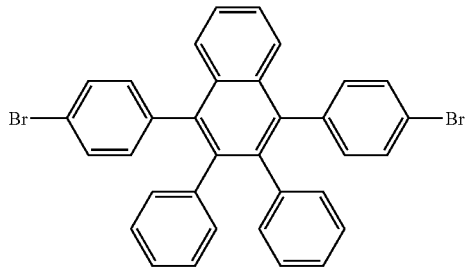

[Formula a]

A starting material represented by Formula i (2.0 g, 3.7 mmol) and isoamyl nitrite (0.54 mL, 4.1 mmol) were added to 50 mL of dichloroethane and heated to dissolve completely. While the mixture was refluxed under stirring, anthranylic acid (0.51 g, 3.7 mmol) completely dissolved in 25 mL of dichloroethane was slowly added dropwise thereto. After the color of the reaction mixture disappeared, the mixture was slowly cooled. The solvent was removed using a vacuum distillation system. The obtained solid was recrystallized from dichloromethane and ethanol to give a white solid powder. The obtained white solid powder was filtered under reduced pressure, and then dried under vacuum to obtain an intermediate material represented by Formula a.

(2.0 g, 93%); $^1$H NMR (400 MHz, DMSO-$d_6$) 7.48 (s, 4H), 7.45-7.43 (d, 4H), 7.17-7.15 (d, 4H), 6.92-6.91 (d, 4H), 6.92-6.88 (m, 6H); MS [M+H] 588, 590, 592

Preparation of Intermediate Material Represented by Formula b

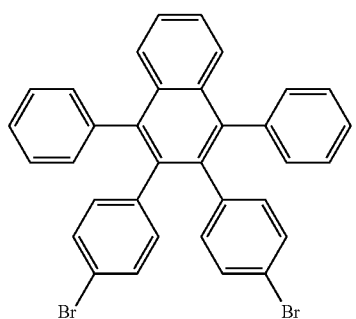

[Formula b]

A starting material represented by Formula j (5.72 g, 10.5 mmol) and isoamyl nitrite (1.54 mL, 11.6 mmol) were added to 50 mL of dichloroethane and heated to dissolve completely. While the mixture was refluxed under stirring, anthranylic acid (1.44 g, 10.5 mmol) dissolved in 50 mL of dichloroethane was slowly added dropwise thereto. After the color of the reaction mixture disappeared, the mixture was slowly cooled. The solvent was removed using a vacuum distillation system. The obtained solid was recrystallized from dichloromethane and ethanol to give a white solid powder. The obtained white solid powder was filtered under reduced pressure, and then dried under vacuum to obtain an intermediate material represented by Formula b.

(4.9 g, 79%); $^1$H NMR (400 MHz, DMSO-$d_6$) 7.50-7.43 (m, 4H), 7.33-7.20 (m, 10H), 7.13-7.11 (d, 4H), 6.89-6.87 (d, 4H); MS [M+H] 588, 590, 592

Preparation of Intermediate Material Represented by Formula c

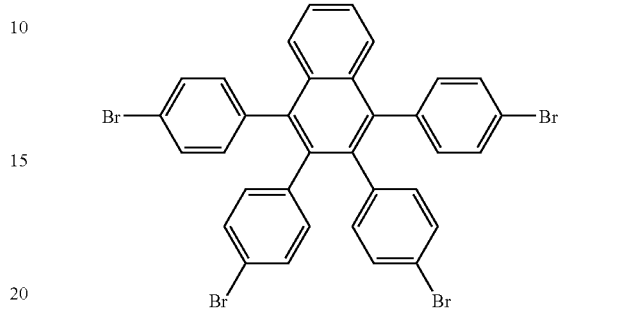

[Formula c]

A starting material represented by Formula k (3.50 g, 5 mmol) and isoamyl nitrite (0.73 mL, 11.6 mmol) were added to 50 mL of dichloroethane and heated to dissolve completely. While the mixture was refluxed under stirring, anthranylic acid (0.754 g, 5.5 mmol) dissolved in 50 mL of dichloroethane was slowly added dropwise thereto. After the color of the reaction mixture disappeared, the mixture was slowly cooled. The solvent was removed using a vacuum distillation system. The obtained solid was recrystallized from dichloromethane and ethanol to give a white solid powder. The obtained white solid powder was filtered under reduced pressure, and then dried under vacuum to obtain an intermediate material represented by Formula c.

(2.43 g, 65%); $^1$H NMR (400 MHz, DMSO-$d_6$) 7.32-7.37 (m, 10H), 7.45-7.49 (d, 8H), 7.67 (m, 2H); MS [M+H] 700

Preparation of Intermediate Material Represented by Formula d

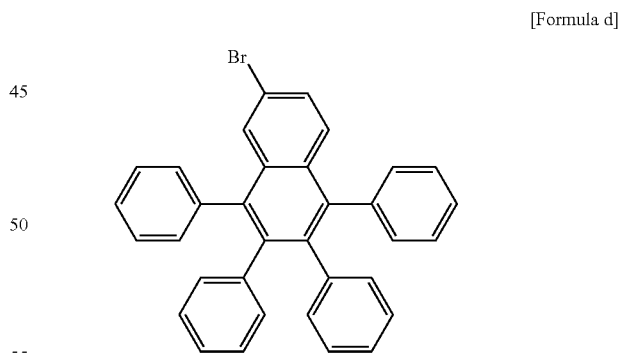

[Formula d]

A starting material represented by Formula h (4.03 g, 10.5 mmol) and isoamyl nitrite (1.54 mL, 11.6 mmol) were added to 50 mL of dichloroethane and heated to dissolve completely. While the mixture was refluxed under stirring, 2-amino 5-bromobenzoic acid (2.27 g, 10.5 mmol) dissolved in 50 mL of dichloroethane was slowly added dropwise thereto. After the color of the reaction mixture disappeared, the mixture was slowly cooled. The solvent was removed using a vacuum distillation system. The obtained solid was recrystallized from dichloromethane and ethanol to give a white solid powder. The obtained white solid powder was filtered under reduced pressure, and then dried under vacuum to obtain an intermediate material represented by Formula d.

(3.75 g, 70%); $^1$H NMR (400 MHz, CDCl$_3$) 7.20-7.32 (m, 12H), 7.43-7.48 (m, 9H), 7.58 (d, 1H), 7.88 (d, 1H); MS [M+H] 512

Preparation of Intermediate Material Represented by Formula e

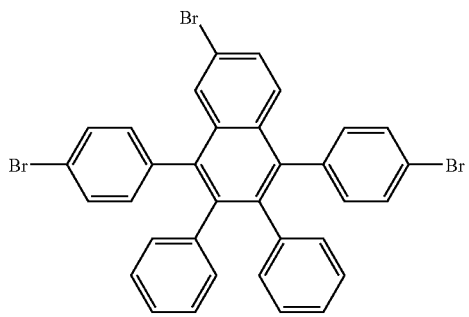

[Formula e]

A starting material represented by Formula i (6.4 g, 11.8 mmol) and isoamyl nitrite (1.73 mL, 13 mmol) were added to 300 μL of dichloroethane and heated to dissolve completely. While the mixture was refluxed under stirring, 2-amino-5-bromobenzoic acid (2.80 g, 13 mmol) dissolved in 100 mL of dichloroethane was slowly added dropwise thereto. After the color of the reaction mixture disappeared, the mixture was slowly cooled. The solvent was removed using a vacuum distillation system. The obtained solid was recrystallized from dichloromethane and ethanol to give a white solid powder. The obtained white solid powder was filtered under reduced pressure, and then dried under vacuum to obtain an intermediate material represented by Formula e.

(6.8 g, 86%); $^1$H NMR (500 MHz, DMSO-d$_6$) 7.67-7.65 (dd, 1H), 7.53-7.52 (d, 1H), 7.50-7.46 (dt, 4H), 7.40-7.38 (d, 1H), 7.20-7.16 (dt, 4H), 6.94-6.86 (m, 10H); MS [M+H] 665, 666, 667, 668, 669, 670, 671

Preparation of Intermediate Material Represented by Formula f

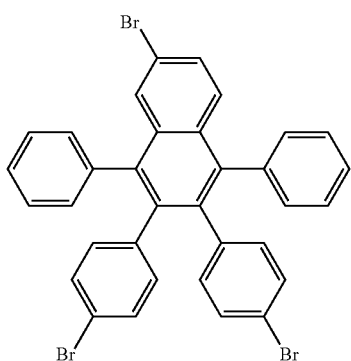

[Formula f]

A starting material represented by Formula j (5.72 g, 10.5 mmol) and isoamyl nitrite (1.54 mL, 11.6 mmol) were added to 50 mL of dichloroethane and heated to dissolve completely. While the mixture was refluxed under sting, 2-amino-5-bromobenzoic acid (2.27 g, 10.5 mmol) dissolved in 50 mL of dichloroethane was slowly added dropwise thereto. After the color of the reaction mixture disappeared, the mixture was slowly cooled. The solvent was removed using a vacuum distillation system. The obtained solid was recrystallized from dichloromethane and ethanol to give a white solid powder. The obtained white solid powder was filtered under reduced pressure, and then dried under vacuum to obtain an intermediate material represented by Formula f.

(5.62 g, 80%); $^1$H NMR (400 MHz, DMSO-d$_6$) 7.19-7.25 (m, 2H), 7.29-7.39 (m, 8H), 7.44-7.52 (m, 9H), 7.60 (d, 1H), 7.90 (s, 1H); MS [M+H] 670

Preparation of Intermediate Material Represented by Formula g

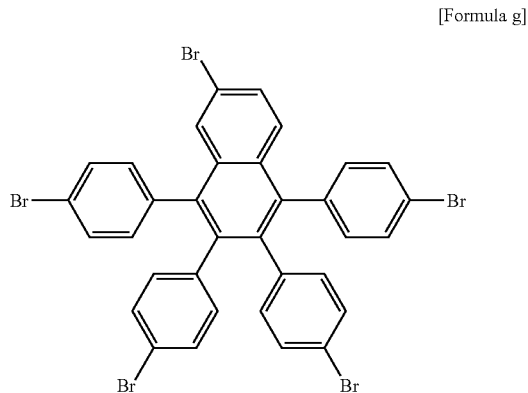

[Formula g]

An intermediate material of Formula g was obtained in the same manner as in the method for preparing the compound of Formula f, except that as a starting material, the compound of Formula k was used instead of the compound of Formula j.

MS [M+H] 827

Preparative Example 1

Preparation of Compound Represented by Formula 1-1

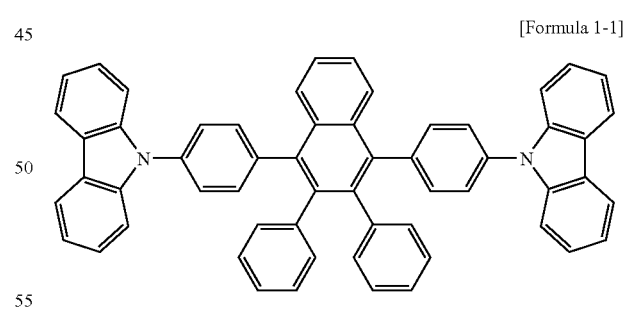

[Formula 1-1]

Formula a (4.9 g, 8.3 mmol), carbazole (3.2 g, 19.1 mmol), sodium t-butoxide (2.0 g, 21 mmol), Pd(dba)$_2$ (0.24 g, 0.4 mmol) and P(t-Bu)$_3$ (0.09 g, 0.4 mmol) were added to toluene (80 mL), and then was refluxed under stirring for about 12 hours. After completing the reaction, the mixture was cooled to room temperature and added to a mixed solution of THF and H$_2$O. The organic layer was separated from the mixture, dried over MgSO$_4$ and concentrated. The residue was purified by column chromatography, and then recrystallized from dichloromethane and ethanol to obtain a compound of Formula 1-1 (2.38 g, 38%).

$^1$H NMR (400 MHz, DMSO-d$_6$) 8.16-8.14 (d, 4H), 7.69-7.68 (q, 2H), 7.56-7.53 (q, 2H), 7.69-7.68 (dd, 2H), 7.42-7.31 (m, 14H), 7.21-7.17 (m, 12H), 6.98-6.96 (dd, 4H); MS [M+H] 763

Preparative Example 2

Preparation of Compound Represented by Formula 1-2

[Formula 1-2]

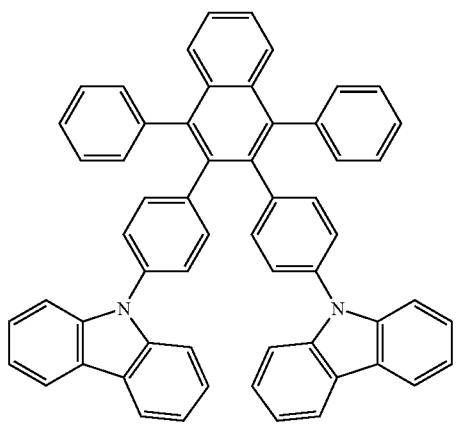

The compound of Formula b (2.0 g, 3.4 mmol), carbazole (1.3 g, 7.8 mmol), sodium t-butoxide (0.81 g, 8.5 mmol), Pd(dba)$_2$ (0.1 g, 0.2 mmol) and P(t-Bu)$_3$ (0.04 g, 0.2 mmol) were added to toluene (40 mL), and then was refluxed under stirring for about 5 hours. After completing the reaction, the mixture was cooled to room temperature and added to a mixed solution of THF and H$_2$O. The organic layer was separated from the mixture, dried over MgSO$_4$ and concentrated. The residue was purified by column chromatography, and then recrystallized from dichloromethane and ethanol to obtain a compound of Formula 1-2 (1.34 g, 52%).

$^1$H NMR (400 MHz, DMSO-d$_6$) 8.26-8.24 (d, 4H), 7.83-7.81 (q, 2H), 7.67-7.65 (q, 2H), 7.55-7.44 (m, 12H), 7.32-7.24 (m, 8H), 7.06-6.97 (m, 10H); MS [M+H] 763

Preparative Example 3

Preparation of Compound Represented by Formula 2-2

[Formula 2-2]

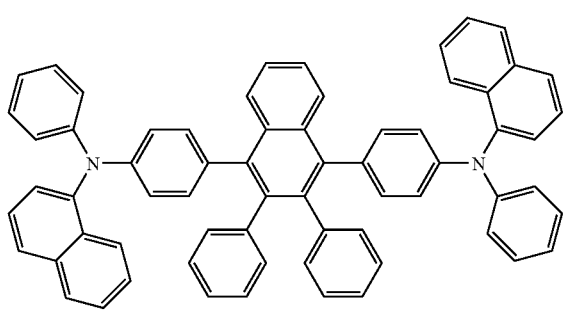

The compound of Formula a (1.3 g, 2.2 mmol), naphthylphenylamine (1.1 g, 5.1 mmol), sodium t-butoxide (0.63 g, 6.6 mmol), Pd(dba)$_2$ (0.06 g, 0.1 mmol) and P(t-Bu)$_3$ (0.03 g, 0.1 mmol) were added to toluene (20 mL), and then the mixture was refluxed under stirring for about 2 hours. After completing the reaction, the mixture was cooled to room temperature and added to a mixed solution of THF and H$_2$O. The organic layer was separated from the mixture, dried over MgSO$_4$ and concentrated. The residue was purified by column chromatography, and then recrystallized from dichloromethane and ethanol to obtain a compound of Formula 2-2 (0.2 g, 11%).

$^1$H NMR (400 MHz, DMSO-d$_6$) 8.00-7.98 (d, 2H), 7.88-7.87 (d, 2H), 7.76-7.74 (d, 2H), 7.63-7.60 (q, 2H), 7.57-7.48 (m, 6H), 7.44-7.40 (t, 2H), 7.26-7.19 (m, 6H), 7.03-7.01 (d, 8H), 6.94-6.90 (m, 8H), 6.86-6.77 (m, 12H); MS [M+H] 867

Preparative Example 4

Preparation of Compound Represented by Formula 2-3

[Formula 2-3]

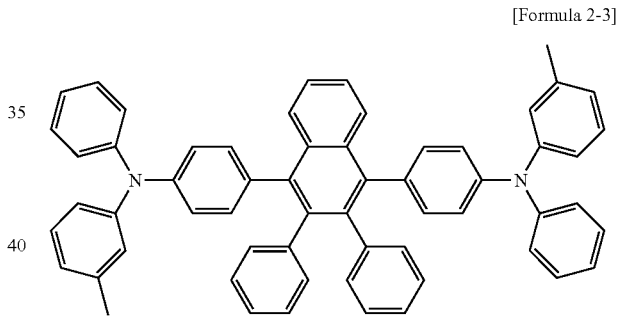

The compound of Formula a (1.3 g, 2.2 mmol), 3-tolylphenylamine (0.87 mL, 5.1 mmol), sodium t-butoxide (0.63 g, 6.6 mmol), Pd(dba)$_2$ (0.06 g, 0.1 mmol) and P(t-Bu)$_3$ (0.03 g, 0.1 mmol) were added to toluene (20 mL), and then was refluxed under stirring for about 2 hours. After completing the reaction, the mixture was cooled to room temperature and added to a mixed solution of THF and H$_2$O. The organic layer was separated from the mixture, dried over MgSO$_4$ and concentrated. The residue was purified by column chromatography, and then recrystallized from dichloromethane and ethanol to obtain a compound of Formula 2-3 (1.3 g, 74%).

$^1$H NMR (400 MHz, DMSO-d$_6$) 7.71-7.69 (q, 2H), 7.56-7.54 (q, 2H), 7.29-7.25 (t, 4H), 7.18-7.15 (t, 2H), 7.10-7.08 (d, 4H), 7.02-6.98 (t, 2H), 6.96-6.95 (m, 6H), 6.91-6.88 (m, 8H), 6.85-6.82 (m, 6H), 6.72-6.70 (d, 4H), 2.22 (s, 6H); MS [M+H] 795

Preparative Example 5

Preparation of Compound Represented by Formula 2-5

[Formula 2-5]

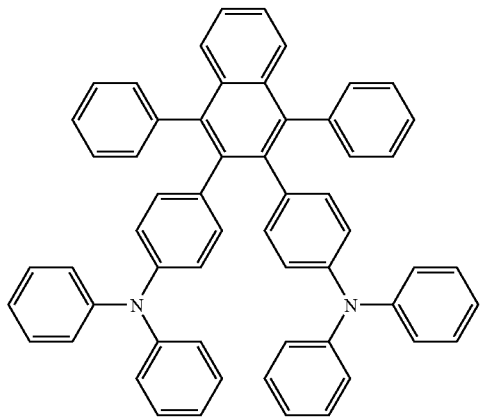

The compound of Formula b (0.83 g, 1.4 mmol), diphenylamine (0.50 g, 3.0 mmol), sodium t-butoxide (0.34 g, 3.5 mmol), Pd(dba)$_2$ (0.03 g, 0.04 mmol) and P(t-Bu)$_3$ (0.02 g, 0.04 mmol) were added to toluene (14 mL), and then was refluxed under stirring for about 1 hour. After completing the reaction, the mixture was cooled to room temperature and added to a mixed solution of THF and H$_2$O. The organic layer was separated from the mixture, dried over MgSO$_4$ and concentrated. The residue was purified by column chromatography, and then recrystallized from dichloromethane and ethanol to obtain a compound of Formula 2-5 (0.25 g, 23%).

MS [M+H] 767

Preparative Example 6

Preparation of Compound Represented by Formula 2-6

[Formula 2-6]

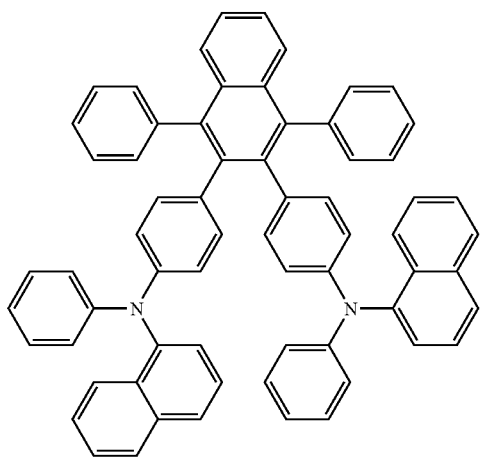

The compound of Formula b (1.5 g, 2.54 mmol), naphthylphenylamine (1.1 g, 5.1 mmol), sodium t-butoxide (0.73 g, 5.8 mmol), Pd(dba)$_2$ (0.07 g, 0.13 mmol) and P(t-Bu)$_3$ (0.03 g, 0.13 mmol) were added to toluene (25 mL), and then was refluxed under stirring for about 2 hours. After completing the reaction, the mixture was cooled to room temperature and added to a mixed solution of THF and H$_2$O. The organic layer was separated from the mixture, dried over MgSO$_4$ and concentrated. The residue was purified by column chromatography, and then recrystallized from dichloromethane and ethanol to obtain a compound of Formula 2-6 (0.85 g, 38%).

$^1$H NMR (400 MHz, DMSO-d$_6$) 7.58-7.54 (m, 2H), 7.49-7.47 (m, 2H), 7.37-7.29 (t, 6H), 7.25-7.23 (d, 4H), 7.18-7.14 (t, 4H), 7.08-7.04 (t, 2H), 6.94-6.90 (t, 2H), 6.84-6.82 (d, 4H), 6.76-6.72 (t, 6H), 6.59-6.57 (d, 6H), 6.53 (s, 2H); MS [M+H] 867

Preparative Example 7

Preparation of Compound Represented by Formula 2-7

[Formula 2-7]

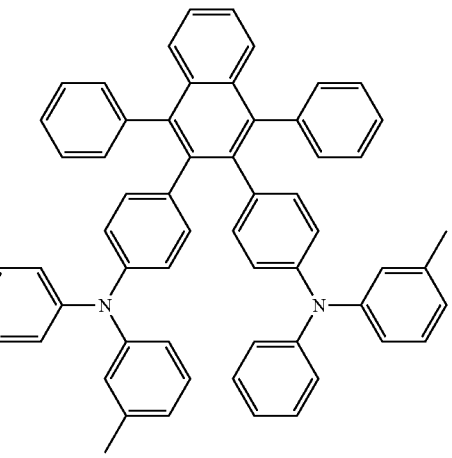

Formula b (1.5 g, 2.54 mmol), 3-tolylphenylamine (1.01 mL, 5.1 mmol), sodium t-butoxide (0.73 g, 5.8 mmol), Pd(dba)$_2$ (0.07 g, 0.13 mmol) and P(t-Bu)$_3$ (0.03 g, 0.13 mmol) were added to toluene (25 mL), and then was refluxed under stirring for about 2 hours. After completing the reaction, the mixture was cooled to room temperature and added to a mixed solution of THF and H$_2$O. The organic layer was separated from the mixture, dried over MgSO$_4$ and concentrated. The residue was purified by column chromatography, and then recrystallized from dichloromethane and ethanol to obtain a compound of Formula 2-7 (0.72 g, 36%).

$^1$H NMR (400 MHz, DMSO-d$_6$) 7.94-7.92 (d, 2H), 7.81-7.79 (d, 2H), 7.60-7.58 (d, 2H), 7.52-7.49 (q, 2H), 7.45-7.40

(m, 6H), 7.33-7.30 (m, 6H), 7.23-7.12 (m, 10H), 7.08-7.06 (d, 2H), 6.91-6.87 (t, 2H), 6.72-6.65 (dd, 8H), 6.52-6.49 (d, 4H), 2.11 (s, 6H); MS [M+H] 795

Preparative Example 8

Preparation of Compound Represented by Formula 2-9

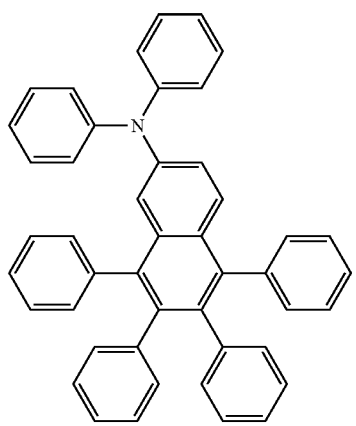

[Formula 2-9]

The compound of Formula d (1.06 g, 2.07 mmol), diphenylamine (0.39 g, 2.3 mmol), sodium t-butoxide (0.24 g, 2.5 mmol), Pd(dba)$_2$ (0.024 g, 0.04 mmol) and P(t-Bu)$_3$ (0.01 g, 0.04 mmol) were added to toluene (20 mL), and then was refluxed under stirring for about 1 hour. After completing the reaction, the mixture was cooled to room temperature and added to a mixed solution of THF and H$_2$O. The organic layer was separated from the mixture, dried over MgSO$_4$ and concentrated. The residue was purified by column chromatography, and then recrystallized from dichloromethane and ethanol to obtain a compound of Formula 2-9 (0.9 g, 73%).

$^1$H NMR (400 MHz, DMSO-d$_6$) 7.35-7.32 (d, 1H), 7.27-7.17 (m, 9H), 7.13-7.11 (d, 1H), 7.04-7.02 (m, 6H), 7.01-6.97 (m, 6H), 6.86-6.84 (m, 8H), 6.82-6.78 (m, 2H); MS [M+H] 600

Preparative Example 9

Preparation of Compound Represented by Formula 2-10

[Formula 2-10]

The compound of Formula e (0.51 g, 0.76 mmol), diphenylamine (0.41 g, 2.4 mmol), sodium t-butoxide (0.26 g, 2.7 mmol), Pd(dba)$_2$ (0.022 g, 0.04 mmol) and P(t-Bu)$_3$ (0.01 g, 0.04 mmol) were added to toluene (40 mL), and then was refluxed under stirring for about 12 hours. After completing the reaction, the mixture was cooled to room temperature and added to a mixed solution of THF and H$_2$O. The organic layer was separated from the mixture, dried over MgSO$_4$ and concentrated. The residue was purified by column chromatography, and then recrystallized from dichloromethane and ethanol to obtain a compound of Formula 2-10 (0.45 g, 65%).

$^1$H NMR (400 MHz, DMSO-d$_6$) 7.35-7.32 (d, 1H), 7.27-7.17 (m, 9H), 7.13-7.11 (d, 1H), 7.04-7.02 (m, 6H), 7.01-6.97 (m, 6H), 6.86-6.84 (m, 8H), 6.82-6.78 (m, 2H); MS [M+H] 934

Preparative Example 10

Preparation of Compound Represented by Formula 3-1

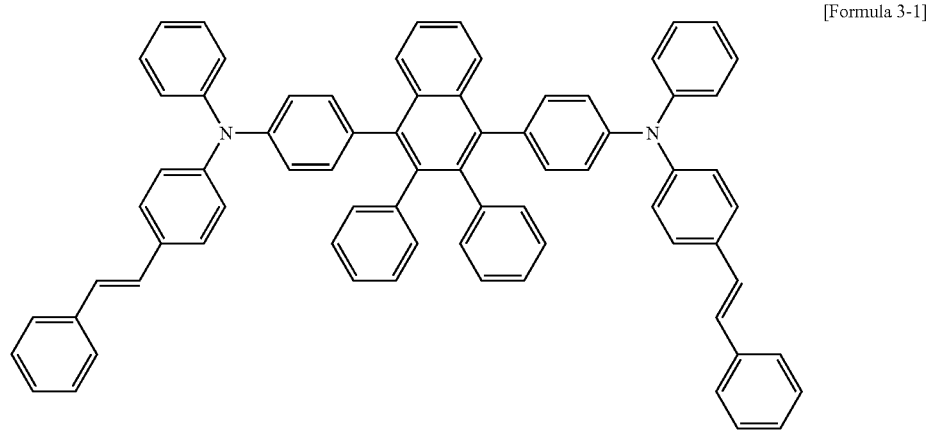

[Formula 3-1]

The compound of Formula a (0.50 g, 0.85 mmol), 4-phenylaminostilbene (0.48 g, 1.8 mmol), sodium t-butoxide (0.20 g, 2.1 mmol), Pd(dba)$_2$ (0.03 g, 0.05 mmol) and P(t-Bu)$_3$ (0.01 g, 0.05 mmol) were added to toluene (40 mL), and then was refluxed under stirring for about 1 hour. After completing the reaction, the mixture was cooled to room temperature and added to a mixed solution of THF and H$_2$O. The organic layer was separated from the mixture, dried over MgSO$_4$ and concentrated. The residue was purified by column chromatography, and then recrystallized from dichloromethane and ethanol to obtain a compound of Formula 3-1 (0.2 g, 24%).

$^1$H NMR (400 MHz, DMSO-d$_6$) 7.74-7.72 (q, 2H), 7.58-7.56 (d, 6H), 7.52-7.49 (d, 4H), 7.38-7.29 (m, 8H), 7.26-7.23 (t, 2H), 7.19-7.05 (m, 10H), 7.00-6.95 (m, 10H), 6.92-6.86 (m, 12H); MS [M+H] 971

Preparative Example 11

Preparation of Compound Represented by Formula 3-4

The compound of Formula b (0.50 g, 0.85 mmol), 4-phenylaminostilbene (0.48 g, 1.8 mmol), sodium t-butoxide (0.20 g, 2.1 mmol), Pd(dba)$_2$ (0.01 g, 0.02 mmol) and P(t-Bu)$_3$ (0.005 g, 0.02 mmol) were added to toluene (20 mL), and then was refluxed under stirring for about 3 hours. After completing the reaction, the mixture was cooled to room temperature and added to a mixed solution of THF and H$_2$O. The organic layer was separated from the mixture, dried over MgSO$_4$ and concentrated. The residue was purified by column chromatography, and then recrystallized from dichloromethane and ethanol to obtain a compound of Formula 3-4 (0.57 g, 69%).

$^1$H NMR (400 MHz, DMSO-d$_6$) 7.61-7.59 (q, 2H), 7.50-7.48 (d, 4H), 7.46-7.44 (q, 2H), 7.39-7.31 (m, 14H), 7.27-7.20 (m, 10H), 7.09-6.98 (m, 6H), 6.90-6.85 (m, 8H), 6.80-6.78 (d, 4H), 6.68-6.66 (d, 4H); MS [M+H] 971

[Formula 3-4]

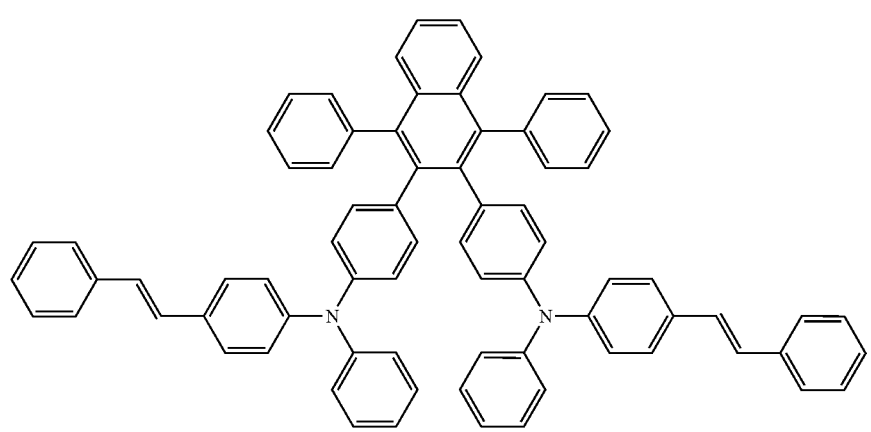

Preparative Example 12

Preparation of Compound Represented by Formula 3-7

[Formula 3-7]

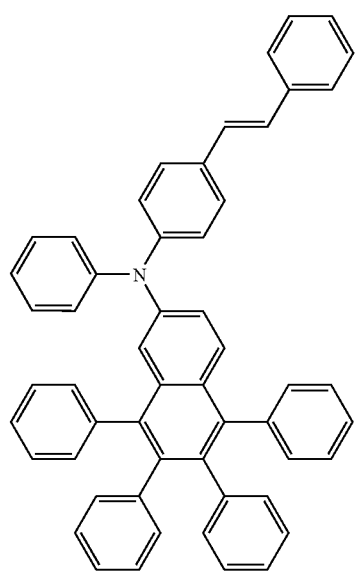

The compound of Formula d (0.49 g, 0.96 mmol), 4-phenylaminostilbene (0.28 g, 1.1 mmol), sodium t-butoxide (0.12 g, 2.9 mmol), Pd(dba)$_2$ (0.006 g, 0.01 mmol) and P(t-Bu)$_3$ (0.003 g, 0.01 mmol) were added to toluene (10 mL), and then was refluxed under stirring for about 2 hours. After completing the reaction, the mixture was cooled to room temperature and added to a mixed solution of THF and H$_2$O. The organic layer was separated from the mixture, dried over MgSO$_4$ and concentrated. The residue was purified by column chromatography, and then recrystallized from dichloromethane and ethanol to obtain a compound of Formula 3-7 (0.99 g, 73%).

$^1$H NMR (400 MHz, DMSO-d$_6$) 7.58-7.56 (d, 2H), 7.49-7.47 (d, 2H), 7.38-7.36 (m, 3H), 7.30-7.14 (m, 11H), 7.09-7.6.96 (m, 11H), 6.87-6.78 (m, 10H); MS [M+H] 702

Preparative Example 13

Preparation of Compound Represented by Formula 3-8

[Formula 3-8]

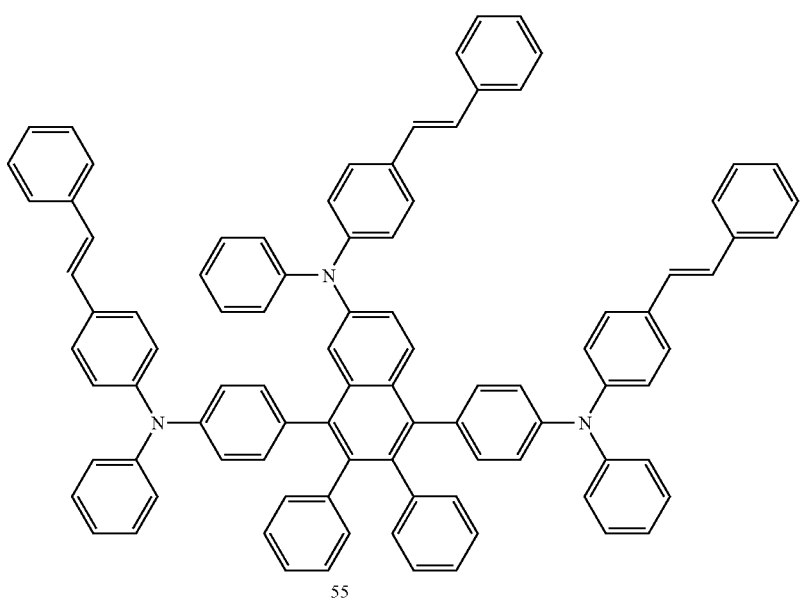

The compound of Formula e (0.50 g, 0.75 mmol), 4-phenylaminostilbene (0.63 g, 2.3 mmol), sodium t-butoxide (0.25 g, 2.6 mmol), Pd(dba)$_2$ (0.01 g, 0.015 mmol) and P(t-Bu)$_3$ (0.003 g, 0.015 mmol) were added to toluene (20 mL), and then was refluxed under stirring for about 3 hours. After completing the reaction, the mixture was cooled to room temperature and added to a mixed solution of THF and H$_2$O. The organic layer was separated from the mixture, dried over MgSO$_4$ and concentrated. The residue was purified by column chromatography, and then recrystallized from dichloromethane and ethanol to obtain a compound of Formula 3-8 (0.87 g, 93%).

¹H NMR (400 MHz, DMSO-d₆) 7.61-7.59 (d, 1H), 7.52-7.45 (m, 10H), 7.41-7.20 (m, 19H), 7.14-7.04 (m, 14H), 6.98-6.90 (m, 19H), 6.84-6.82 (d, 2H), 6.77-6.73 (t, 4H); MS [M+H] 1240

Preparative Example 14

Preparation of Compound Represented by Formula 5-1

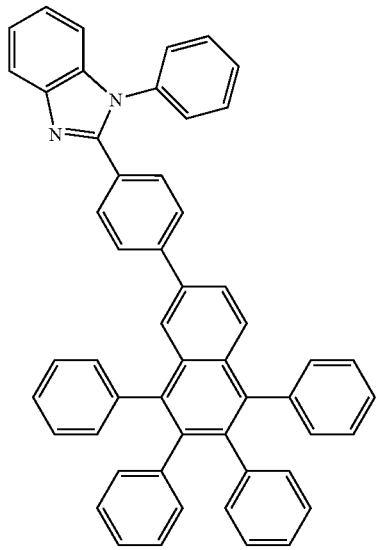

[Formula 5-1]

The compound of Formula d (3 g, 5.8 mmol), 4-formyl-benzeneboronic acid (0.97 g, 6.4 mmol), Pd(PPh₃)₄ (0.02 g, 0.017 mmol) were added to toluene (30 mL), and then 4M K₂CO₃ solution (15 ml) was added thereto. The mixture was refluxed under stirring for about 3 hours. After completing the reaction, the mixture was cooled to room temperature. The toluene layer was separated from the mixture, and the aqueous layer was extracted with CH₂Cl₂ (30 ml). The organic layer was separated, dried over MgSO₄ and concentrated. The residue was purified by column chromatography, and then re-crystallized from dichloromethane and ethanol to obtain a white compound (2.2 g, 70%). The compound was dissolved in 5 ml of acetic acid, and then N-phenylbenzene 1,2-diamine (0.75 g, 4 mmol) was added thereto. The mixture was refluxed under stirring for about 3 hours, and then cooled to room temperature. The obtained solid was filtered and the filtrate was washed with ethanol and water to obtain a compound of Formula 5-1 (2.29 g, 80%).

¹H NMR (400 MHz, DMSO-d₆) 7.20-7.34 (m, 19H), 7.43-7.50 (m, 8H), 7.52-7.56 (m, 5H), 7.69-7.74 (m, 3H), 7.90 (s, 1H); MS [M+H] 700

Preparative Example 15

Preparation of Compound Represented by Formula 5-2

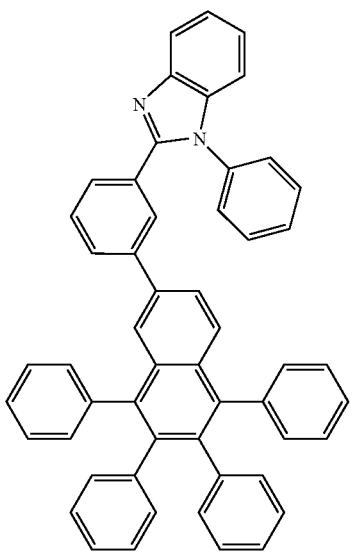

[Formula 5-2]

The compound of Formula d (3 g, 5.8 mmol), 4-formyl-benzeneboronic acid (0.97 g, 6.4 mmol), Pd(PPh₃)₄ (0.02 g, 0.017 mmol) were added to toluene (30 mL), and then 4M K₂CO₃ solution (15 ml) was added thereto. The mixture was refluxed under stirring for about 3 hours. After completing the reaction, the mixture was cooled to room temperature. The toluene layer was separated from the mixture, and the aqueous layer was extracted with CH₂Cl₂ (30 ml). The organic layer was separated, dried over MgSO₄ and concentrated. The residue was purified by column chromatography, and then re-crystallized from dichloromethane and ethanol to obtain a white compound (1.9 g, 60%). The compound was dissolved in 5 ml of acetic acid, and then N-phenylbenzene 1,2-diamine (0.65 g, 3.5 mmol) was added thereto. The mixture was refluxed under stirring for about 3 hours, and then cooled to room temperature. The obtained solid was filtered and the filtrate was washed with ethanol and water to obtain a compound of Formula 5-2 (1.98 g, 80%).

$^1$H NMR (400 MHz, DMSO-d$_6$) 7.20-7.36 (m, 20H), 7.43-7.56 (m, 11H), 7.69-7.74 (m, 4H), 7.90 (s, 1H); MS [M+H] 701

Preparative Example 16

Preparation of Compound Represented by Formula 6-1

[Formula 6-1]

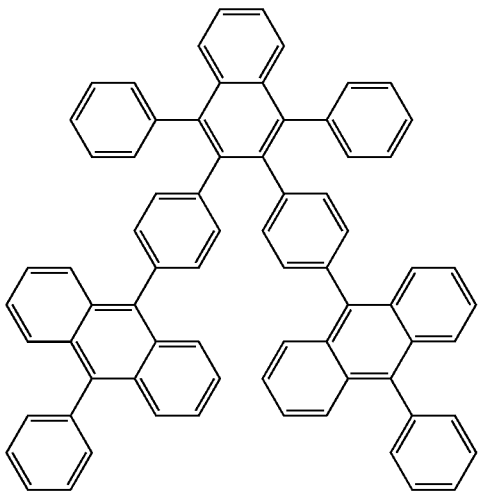

The compound of Formula b (0.89 g, 1.5 mmol), 9-phenyl-10-anthraceneboronic acid (2.2 g, 7.5 mmol), Pd(PPh$_3$)$_4$ (0.3 g, 0.3 mmol) were added to 2M K$_2$CO$_3$ solution (200 ml) and THF (200 ml). The mixture was refluxed under stirring for about 24 hours. After completing the reaction, the mixture was cooled to room temperature. The organic layer was separated, and filtered to obtain a solid. The solid was dissolved in THF, purified by column chromatography, and recrystallized from THF and ethanol to obtain a compound of Formula 6-1 (1.0 g, 71%).
$^1$H NMR (400 MHz, DMSO-d$_6$) 7.92-7.90 (q, 2H), 7.69-7.67 (q, 2H), 7.62-7.41 (m, 26H), 7.36-7.33 (q, 4H), 7.28-7.26 (d, 6H), 7.15-7.11 (m, 6H), 6.84-6.80 (t, 2H); MS [M+H] 937

Preparative Example 17

Preparation of Compound Represented by Formula 6-2

A compound of Formula 6-2 was obtained in the same manner as in Preparative Example 16, except that the compound of Formula a was used instead of the compound of Formula b.
$^1$H NMR (400 MHz, DMSO-d$_6$) 8.13-8.11 (m, 2H), 7.97-7.95 (m, 2H), 7.20-7.71 (m, 44H); MS [M+H] 937

Preparative Example 18

Preparation of Compound Represented by Formula 5-9

[Formula 5-9]

The compound of Formula a (1.0 g, 1.6 mmol) was added to anhydrous THF (50 mL), and cooled to −78° C. under stirring. nBuLi (2.5 M in hexane, 3.2 mmol, 1.28 ml) was slowly added thereto, and stirred for about 1 hour. The mixture was stirred for another 1 hour at room temperature. Triphenylsilylchloride (0.77 g, 2.6 mmol) was slowly added thereto with a syringe, and then stirred for 2 hours. After the reaction was completely finished with a small amount of water, the reaction mixture was added to a mixed solution of THF and H$_2$O. The organic layer was separated, dried over MgSO$_4$ and concentrated. The residue was purified by column chromatography, and then re-crystallized from dichloromethane and ethanol to obtain a compound of Formula 5-9 (0.5 g, 33%).
MS [M+H] 949

[Formula 6-2]

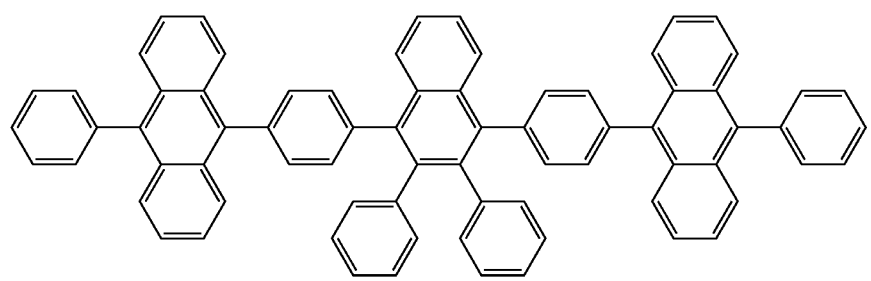

Preparative Example 19

Preparation of Compound Represented by Formula 5-10

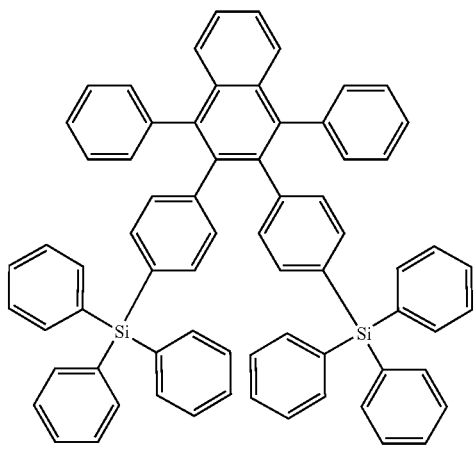

[Formula 5-10]

The compound of Formula b (1.0 g, 1.6 mmol) was added to anhydrous THF (50 mL), and cooled to −78° C. under stirring. nBuLi (2.5 M in hexane, 3.2 mmol, 1.28 ml) was slowly added thereto, and stirred for about 1 hour. The mixture was stirred for another 1 hour at room temperature. Triphenylsilylchloride (0.77 g, 2.6 mmol) was slowly added thereto with a syringe, and then stirred for 2 hours. After the reaction was completely finished with a small amount of water, the reaction mixture was added to a mixed solution of THF and $H_2O$. The organic layer was separated, dried over $MgSO_4$ and concentrated. The residue was purified by column chromatography, and then re-crystallized from dichloromethane and ethanol to obtain a compound of Formula 5-10 (0.6 g, 40%).

MS [M+H] 949

Preparative Example 20

Preparation of Compound Represented by Formula 5-12

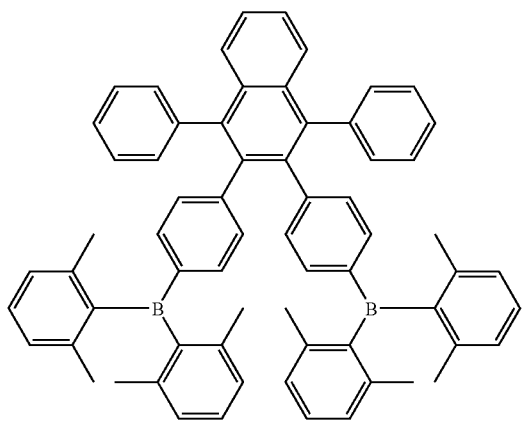

[Formula 5-12]

The compound of Formula b (1.0 g, 1.6 mmol) was added to anhydrous THF (50 mL), and cooled to −78° C. under stirring. nBuLi (2.5 M in hexane, 3.2 mmol, 1.28 ml) was slowly added thereto, and stirred for about 1 hour. Dimesitylboronfluoride (0.8 g, 3.0 mmol) was added, and then stirred for 2 hours. The mixture was stirred for another 12 hour at room temperature. After the reaction was completely finished with a small amount of water, the reaction mixture was added to a mixed solution of THF and $H_2O$. The organic layer was separated, dried over $MgSO_4$ and concentrated. The residue was purified by column chromatography, and then recrystallized from dichloromethane and ethanol to obtain a compound of Formula 5-12 (0.5 g, 36%).

MS [M+H] 873

EXPERIMENTAL EXAMPLES

Experimental Example 1

A glass substrate (Corning 7059 glass) on which a thin film of ITO (indium tin oxide) was coated to a thickness of 1000 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol. The resultant product was dried.

On the ITO electrode, hexanitrile hexaazatriphenylene (500 Å), 4,4′-bis[N-(1-naphthyl)-N-phenyl amino]biphenyl (NPB) (400 Å), $Alq_3$ (300 Å) and the compound (200 Å) of the following Formula 5-1 prepared in Preparative Example 14 were sequentially coated by thermal vacuum deposition to form a hole injecting layer, a hole transporting layer, a light emitting layer, and an electron transporting layer, respectively.

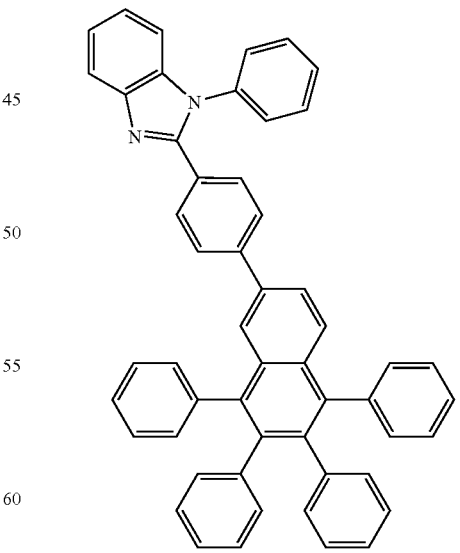

[Formula 5-1]

Lithium fluoride (LiF) and aluminum were sequentially deposited on the electron transporting layer to thicknesses of 12 Å and 2000 Å respectively, to form a cathode, thereby obtaining an organic light emitting device.

In the above process, the deposition rate of the organic material was maintained at 0.4 to 0.7 Å/sec and the deposition rate of lithium fluoride on the cathode was maintained at 0.3 Å/sec and the deposition rate of aluminum was maintained at 2 Å/sec The degree of vacuum upon deposition was maintained at $2\times10^{-7}$ to $5\times10^{-8}$ torr.

When a forward electric field of 6.8 V was applied to the organic light emitting device as prepared above, blue light emission of 3400 nit was observed.

Experimental Example 2

On the ITO electrode prepared in the same manner as in Experimental Example 1, the compound (800 Å) of the following Formula A, 4,4'-bis[N-(1-naphthyl)-N-phenylamino] biphenyl (NPB) (400 Å), the compound (300 Å) of the following Formula 6-1 prepared in Preparative Example 16, and the compound (200 Å) of the following Formula B were sequentially coated by thermal vacuum deposition to form a hole injecting layer, a hole transporting layer, a light emitting layer, and an electron transporting layer, respectively.

[Formula A]

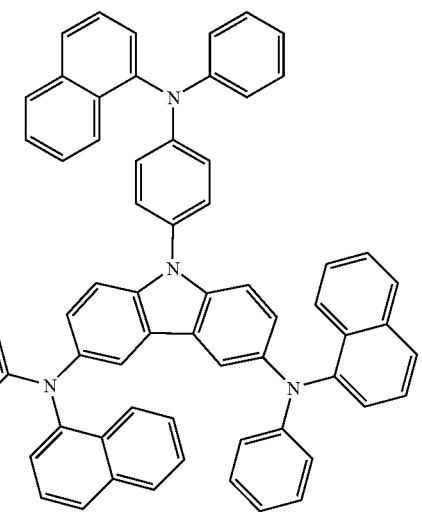

[Formula B]

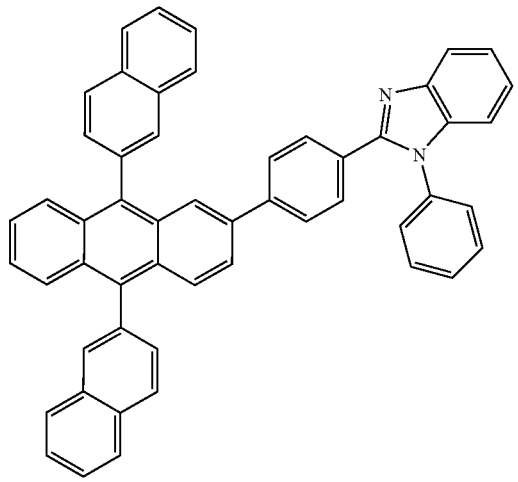

Lithium fluoride (LiF) and aluminum were sequentially deposited on the electron transporting layer (the compound of Formula B) to thicknesses of 12 Å and 2000 Å respectively, to form a cathode, thereby obtaining an organic light emitting device.

In the above process, the deposition rate of the organic material was maintained at 0.4 to 0.7 Å/sec and the deposition rate of lithium fluoride on the cathode was maintained at 0.3 Å/sec and the deposition rate of aluminum was maintained at 2 Å/sec. The degree of vacuum upon deposition was maintained at $2\times10^{-7}$ to $5\times10^{-8}$ torr.

When a forward electric field of 7.9 V was applied to the organic light emitting device as prepared above, blue light emission of 2000 nit was observed.

Experimental Example 3

An organic light emitting device was prepared in the same manner as in Experimental Example 2, except that the compound of Formula 6-2 prepared in Preparative Example 17 was used instead of the compound of Formula 6-1. When a forward electric field of 8.1 V was applied to the organic light emitting device as prepared above, blue light emission of 1700 nit was observed.

Experimental Example 4

An organic light emitting device was prepared in the same manner as in Experimental Example 2, except that 2% by weight of the compound of following Formula C was added to the compound of Formula 6-1 upon forming a light emitting layer. When a forward electric field of 8.1 V was applied to the organic light emitting device as prepared above, blue light emission of 3700 nit was observed.

[Formula C]

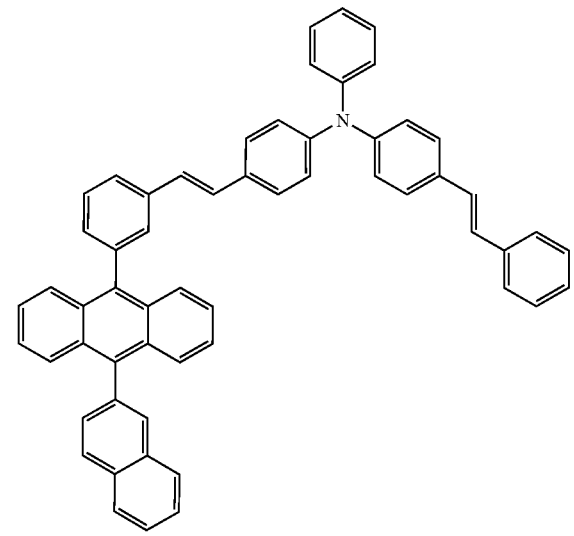

The invention claimed is:
1. A compound of following Formula 1:

[Formula 1]

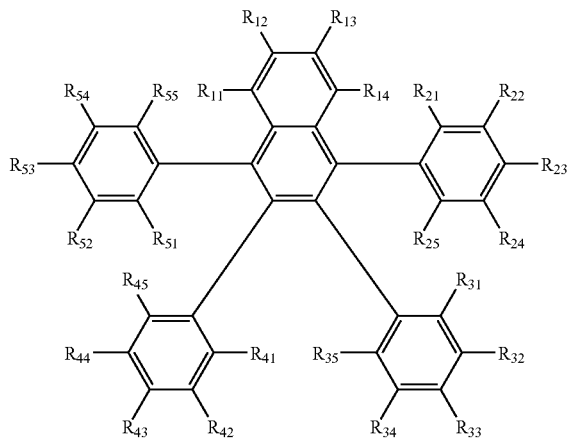

wherein at least one of $R_{11}$ to $R_{14}$ are selected from the group consisting of carbazolyl group, an arylamine group, an arylamine group substituted with an arylamine group, an arylamine group substituted with an arylalkenyl group, an arylalkenyl group substituted with an arylamine group, a bithienyl group substituted with an aryl group, a thienyl group substituted with an aryl group, an imidazolyl group substituted with an aryl group, an aryl group substituted with an imidazolyl group, a benzimidazolyl group substituted with an aryl group, an aryl group substituted with a benzimidazolyl group, a boron group substituted with an alkylaryl group;
the remainder of $R_{11}$ to $R_{14}$ are hydrogen;
$R_{21}$ to $R_{25}$, $R_{31}$ to $R_{35}$, $R_{41}$ to $R_{45}$, and $R_{51}$ to $R_{55}$ are the same or different from each other, and independently selected from the group consisting of a hydrogen atom, a substituted or unsubstituted aliphatic cyclic group, an aromatic cyclic group substituted with hetero aromatic cyclic group, a substituted or unsubstituted thienyl group, a substituted or unsubstituted bithienyl group, a substituted or unsubstituted imidazolyl group, a substituted or unsubstituted heterocyclic group containing Si, a substituted or unsubstituted carbazolyl group, a substituted or unsubstituted carbazolyl group, a substituted or unsubstituted benzimidazolyl group, a condensed ring group formed by two or more rings selected from the above rings, —BR'R", —NR'R", —OR', —PR'R", —SR' and SiR'R"R'", wherein R', R" and R'" are each independently selected from the group consisting of a substituted or unsubstituted arylalkyl group, a substituted or unsubstituted arylalkenyl group, a substituted or unsubstituted arylalkynyl group, a substituted or unsubstituted aliphatic cyclic group, a substituted or unsubstituted heterocyclic group, a substituted or unsubstituted aromatic cyclic group, a substituted or unsubstituted heteroaromatic cyclic group and a condensed ring group formed by two or more rings selected from the above rings, provided that $R_{11}$ to $R_{14}$, $R_{21}$ to $R_{25}$, $R_{31}$ to $R_{35}$, $R_{45}$ to $R_{41}$, and $R_{51}$ to $R_{55}$ are not hydrogen at the same time.
2. The compound according to claim 1, wherein, as a substituent of the compound of the Formula 1, an aliphatic hydrocarbon group, an arylalkyl group, an arylalkenyl group, an arylalkynyl group, an aliphatic cyclic group, a heterocyclic group, an aromatic cyclic group, a heteroaromatic cyclic group, —BR'R", —NR'R", —OR', —PR'R", —SR' and SiR'R"R'" comprise 1 to 10 of at least one atom selected from B, N, 0, P, S and Si.

3. The compound according to claim 1, wherein at least one of $R_{21}$ to $R_{25}$, $R_{31}$ to $R_{35}$, $R_{41}$ to $R_{45}$, and $R_{51}$ to $R_{55}$ of Formula 1 is selected from the group consisting of a carbazolyl group, an arylamine group, an arylamine group substituted with an arylamine group, an arylamine group substituted with an arylalkenyl group, an arylalkenyl group substituted with an arylamine group, a bithienyl group substituted with an aryl group, a thienyl group substituted with an aryl group, an imidazolyl group substituted with an aryl group, an aryl group substituted with an imidazolyl group, a benzimidazolyl group substituted with an aryl group, an aryl group substituted with a benzimidazolyl group, a silane group substituted with an aryl group, a boron group substituted with an alkylaryl group and a heterocyclic group containing Si substituted with an aryl group or an alkyl group.

4. The compound according to claim 1, wherein the compound of Formula 1 is selected from the following compounds of Formulae 14 to 17:

Formula 14

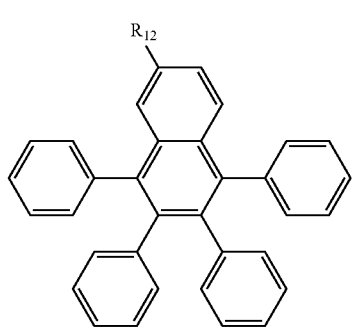

Formula 15

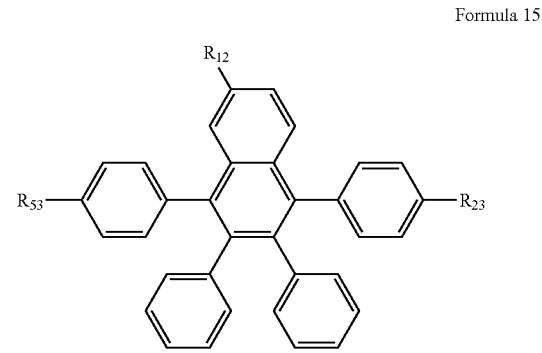

[Formula 16]
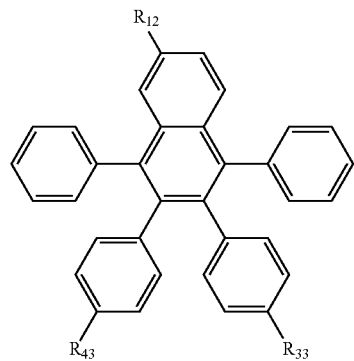
[Formula 17]
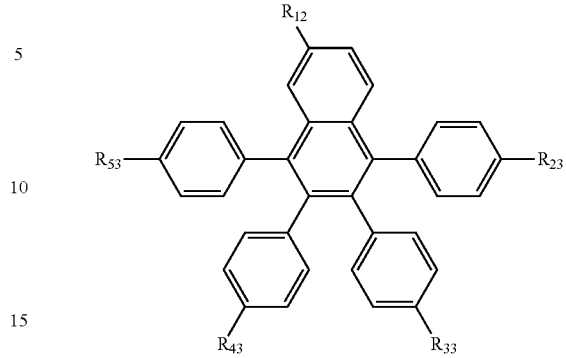
wherein $R_{12}$, $R_{23}$, $R_{33}$, $R_{43}$ and $R_{53}$ are the same as defined in Formula 1, provided that $R^{12}$, $R^{23}$, $R^{33}$, $R^{43}$ and $R^{53}$ are not hydrogen.
5. The compound according to claim 1, wherein the compound of Formula 1 is selected from compounds represented by following Formula:
[Formula 1-4]
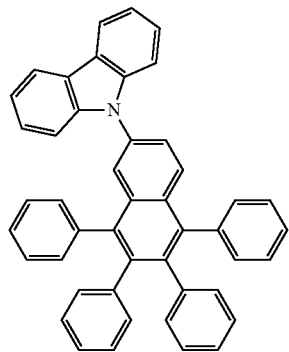
[Formula 1-5]
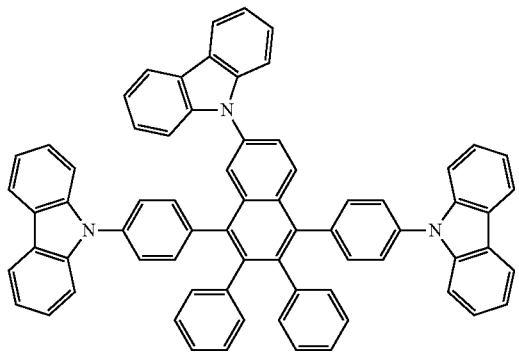
[Formula 1-6]
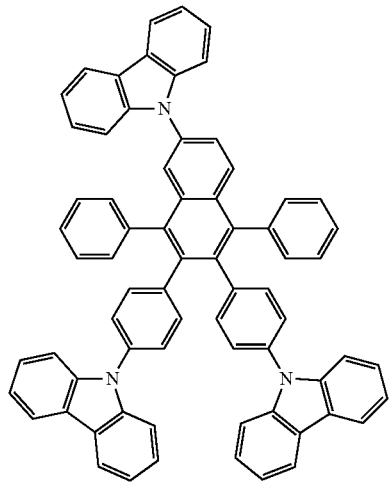
[Formula 2-9]
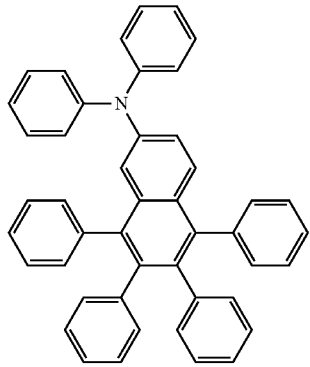

[Formula 2-10]
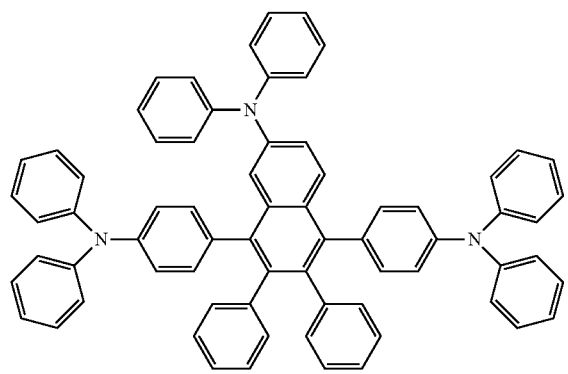
[Formula 2-11]
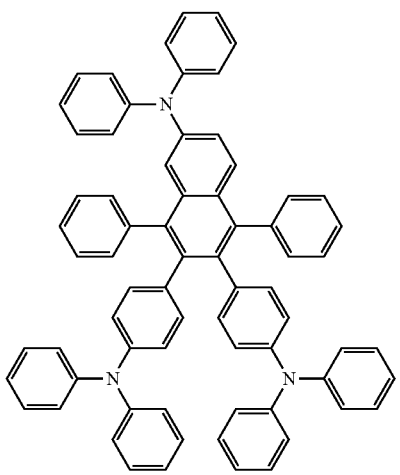
[Formula 2-12]
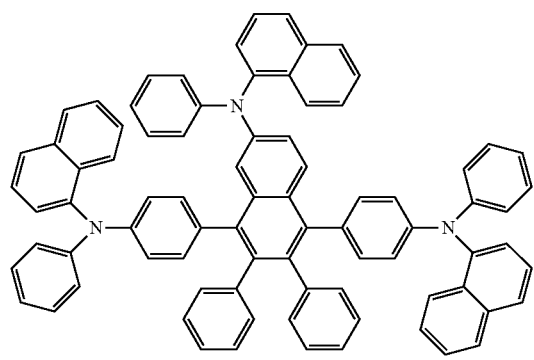
[Formula 2-13]
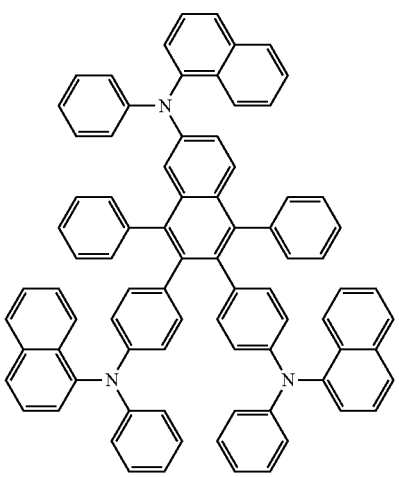
[Formula 2-15]
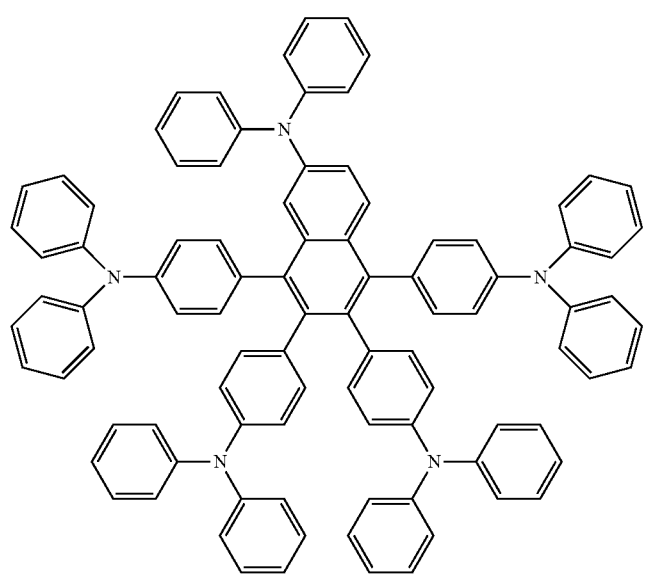

[Formula 2-24]
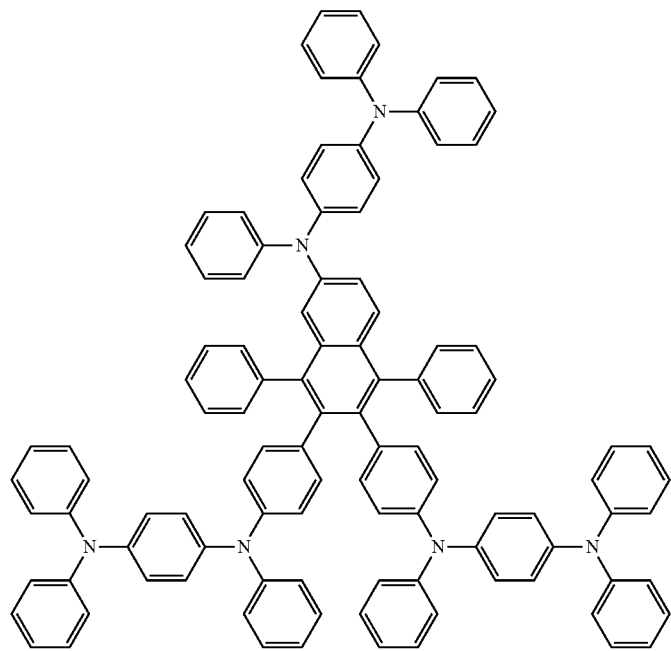
[Formula 3-7]
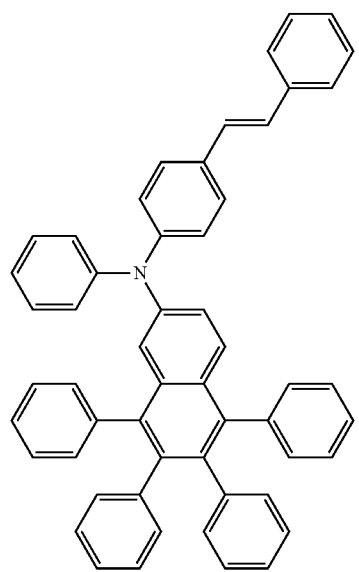

-continued
[Formula 3-8]
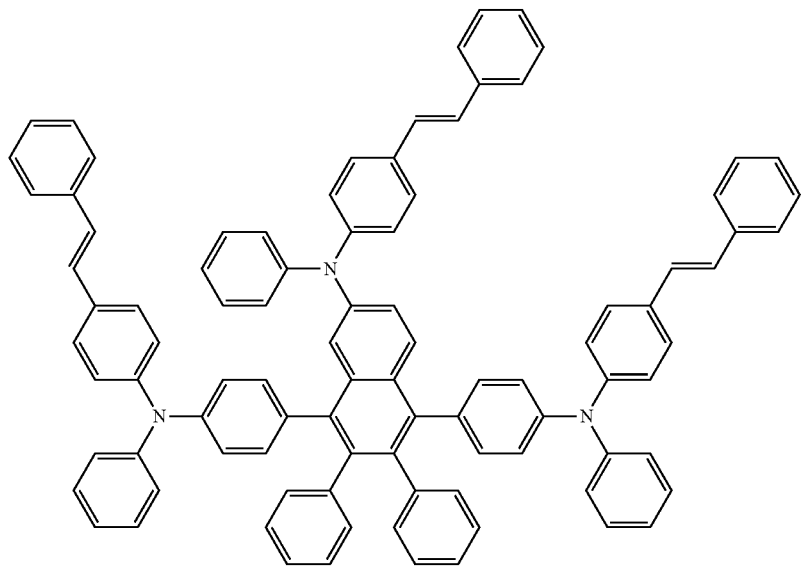
[Formula 3-9]
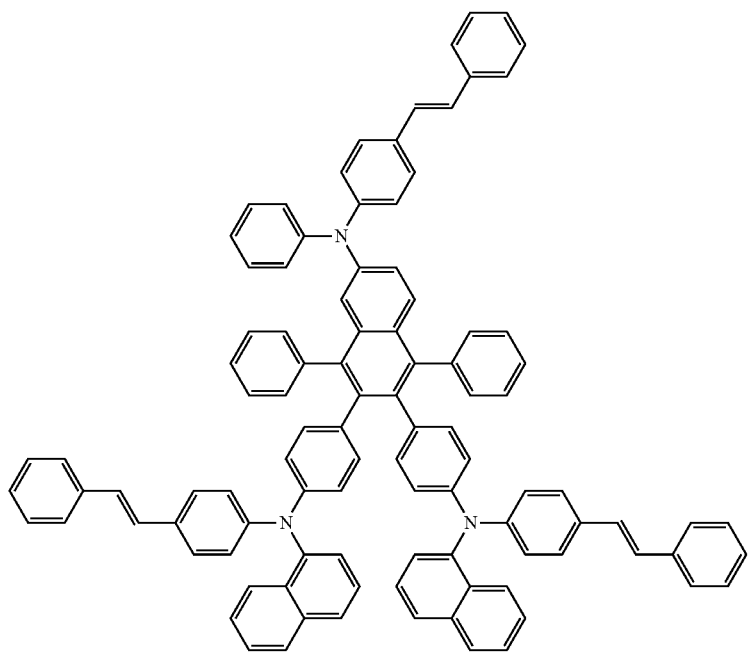
[Formula 4-7]
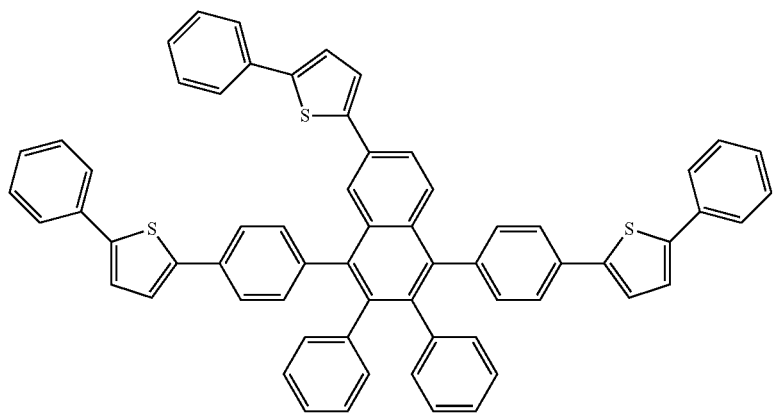

[Formula 4-8]
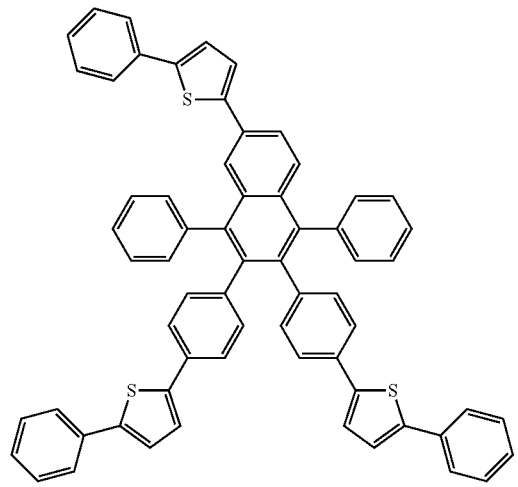
[Formula 4-9]
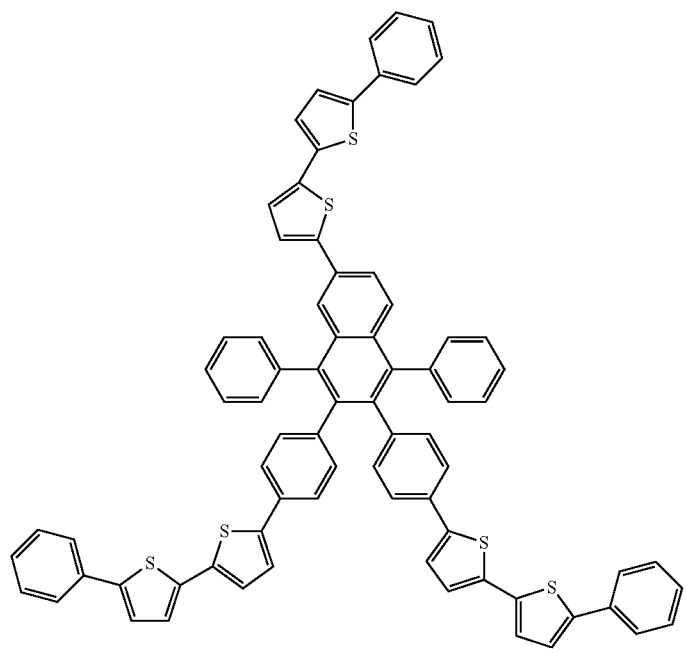

[Formula 5-1]
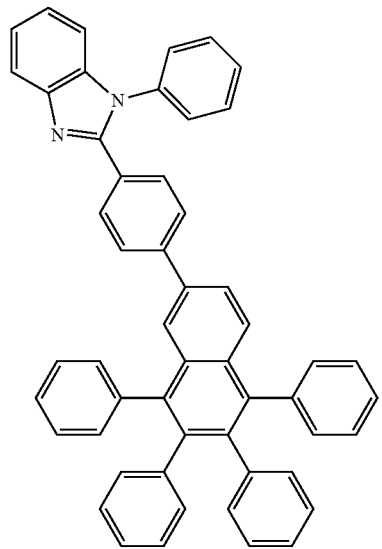
[Formula 5-2]
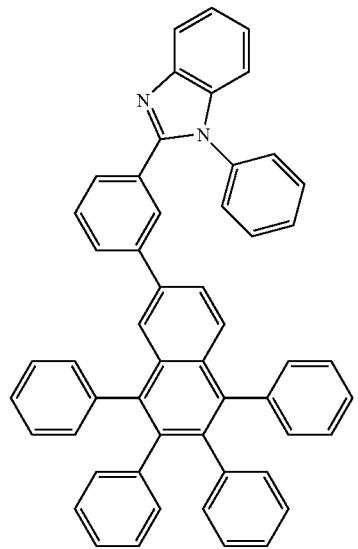
[Formula 5-5]
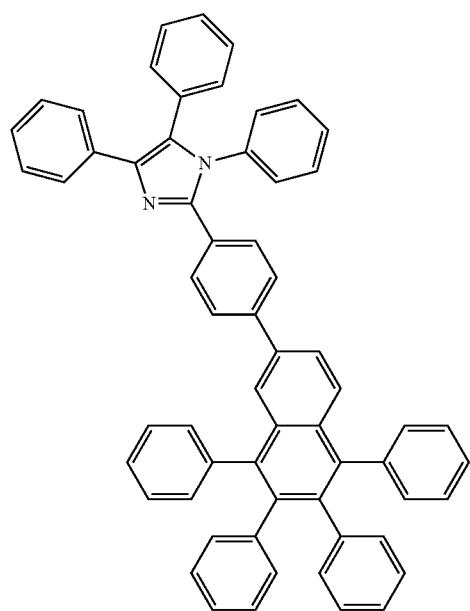
[Formula 5-6]
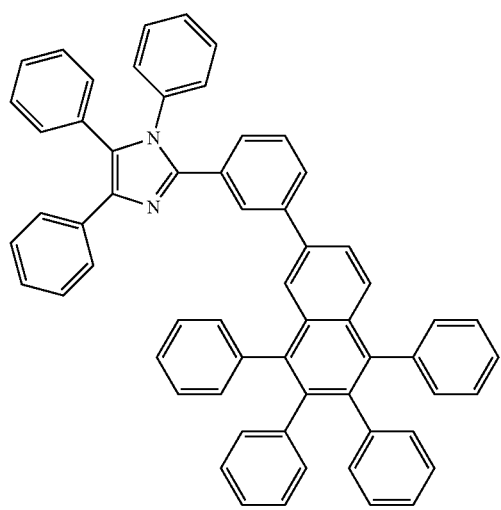

[formula 5-7]
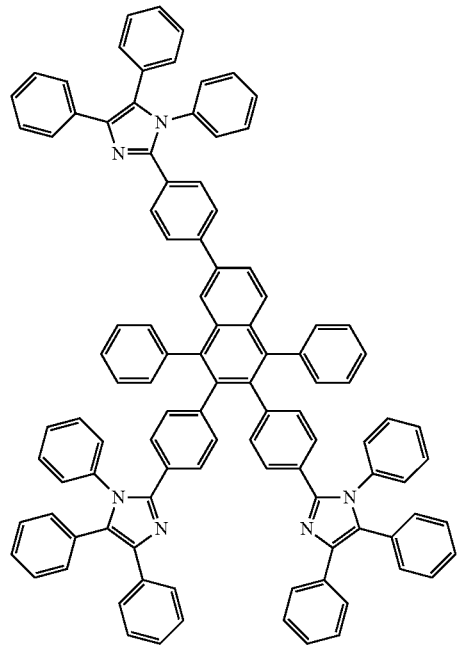
[Formula 5-8]
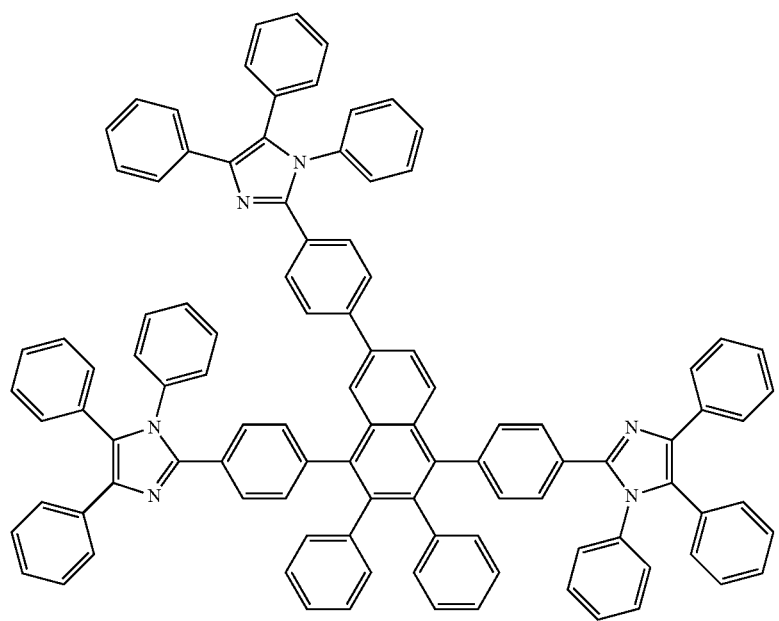

-continued

[Formula 5-13]

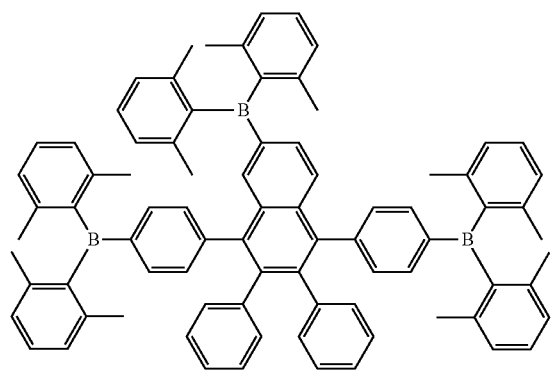

[Formula 5-14]

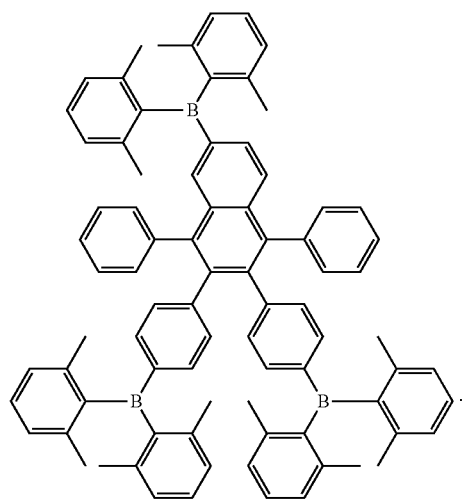

6. An organic light emitting device comprising a first electrode, at least one organic material layer, and a second electrode sequentially stacked, wherein at least one organic material layer comprises the compound according to claim 1.

7. The organic light emitting device according to claim 6, wherein the organic material layer comprises at least one layer selected from the groups consisting of a hole injecting layer, a hole transporting layer, a light emitting layer, an electron transporting layer, and an electron injecting layer.

* * * * *